United States Patent
Kassiou et al.

(10) Patent No.: US 11,491,165 B2
(45) Date of Patent: Nov. 8, 2022

(54) NON-PEPTIDE OXYTOCIN RECEPTOR AGONISTS

(71) Applicant: Kinoxis Therapeutics Pty Ltd, Camberwell (AU)

(72) Inventors: Michael Kassiou, The University of Sydney (AU); William Jorgensen, The University of Sydney (AU); Eryn Werry, The University of Sydney (AU); Tristan Reekie, The University of Sydney (AU); Michael Bowen, The University of Sydney (AU); Iain McGregor, The University of Sydney (AU)

(73) Assignee: Kinoxis Therapeutics Pty Ltd, Camberwell (AU)

( * ) Notice: Subject to any disclaimer, the term of this patent is extended or adjusted under 35 U.S.C. 154(b) by 97 days.

(21) Appl. No.: 16/439,570

(22) Filed: Jun. 12, 2019

(65) Prior Publication Data

US 2020/0000823 A1  Jan. 2, 2020

Related U.S. Application Data

(63) Continuation of application No. PCT/AU2017/051731, filed on Dec. 12, 2017.

(30) Foreign Application Priority Data

Dec. 12, 2016  (AU) .............................. 2016905126

(51) Int. Cl.
*A61K 31/5517* (2006.01)
*A61P 25/00* (2006.01)

(52) U.S. Cl.
CPC .......... *A61K 31/5517* (2013.01); *A61P 25/00* (2018.01)

(58) Field of Classification Search
CPC ............................ A61K 31/5517; A61P 25/00
See application file for complete search history.

(56) References Cited

FOREIGN PATENT DOCUMENTS

| WO | WO 96/022282 A1 | 7/1996 |
|---|---|---|
| WO | WO 03/000692 A2 | 1/2003 |
| WO | WO 03/016316 A1 | 2/2003 |
| WO | WO 2004/072083 A1 | 8/2004 |
| WO | 2005023812 A2 | 3/2005 |
| WO | 2006021213 A2 | 3/2006 |
| WO | WO 2007/050353 A2 | 5/2007 |
| WO | WO 2010/097576 A1 | 9/2010 |

OTHER PUBLICATIONS

CAS Registry No. 877927-94-1, STN Entry date: Mar. 23, 2006, Compound Name: [4-(aminomethyl)cyclohexyl](4,10-dihydro-1-methylpyrazolo[3,4-b][1,5]benzodiazepin-5(1H)-yl)-methanone.
Jorgensen et al : "Flexible Analogues of WAY-267,464: Synthesis and pharmacology at the human oxytocin and vasopressin 1a receptors", European Journal of Medicinal Chemistry 2016, 108, pp. 730-740.
Frantz et al: "Subtlety of the Structure-Affinity and Structure-Efficacy Relationships around a Nonpeptide Oxytocin Receptor Agonist", Journal of Medicinal Chemistry 2010, 53(4), pp. 1546-1562.
Karpenko et al: "Selective Nonpeptidic Fluorescent Ligands for Oxytocin Receptor: Design, Synthesis, and Application to Time-Resolved FRET Binding Assay", Journal of Medicinal Chemistry 2015, 58(5), 2547-2552.
International Search Report dated Apr. 5, 2018 for PCT Application No. PCT/AU2017/051371.
Written Opinion dated Apr. 5, 2018 for PCT Application No. PCT/AU2017/051371.
CAS Registry No. 1780762-56-2, STN Entry Date Jun. 15, 2015, 1 page.
Reekie, T. A. et al., "Synthesis of Biologically Active Seven-Membered-Ring Heterocycles," Synthesis, 45:3211-3227 (2013).
Reekie, T. A. et al., "Pyrazolo[1,4]diazepines as non-peptidic probes of the oxytocin and vasopressin receptors," Tetrahedron Letters, 55:4568-4571 (2014).

*Primary Examiner* — James D. Anderson
*Assistant Examiner* — William Y Lee
(74) *Attorney, Agent, or Firm* — Cooley LLP; Matthew Pavao; Christine E. Dunne

(57) ABSTRACT

Disclosed herein are compounds according to Formula I; a pharmaceutical composition including, consisting essentially of, or consisting of: a pharmaceutically acceptable compound of Formula I and a pharmaceutically acceptable carrier, diluent, or excipient; the use of compounds of Formula I in the preparation of a medicament; and a method including administering a pharmaceutical compositions comprising the compound of Formula I to a patient. The compounds, compositions, use, and methods are directed to the treatment of neurological, psychiatric disorders which are characterised by a fundamental disruption of social behaviour, and substance use disorders.

16 Claims, 1 Drawing Sheet

NON-PEPTIDE OXYTOCIN RECEPTOR AGONISTS

CROSS-REFERENCE TO RELATED APPLICATIONS

This application is a continuation of International Application No. PCT/AU2017/051371, filed Dec. 12, 2017, which claims priority to Australian Application No. 2016905126, filed Dec. 12, 2016, under 35 U.S.C. § 119(a). Each of the above-referenced patent applications is incorporated by reference in its entirety.

FIELD OF THE INVENTION

The present disclosure relates to compounds, compositions and methods for the treatment of neurological, psychiatric disorders which are characterised by a fundamental disruption of social behaviour, and substance use disorders

BACKGROUND OF THE INVENTION

Many psychiatric disorders are characterised by a fundamental disruption of social behaviour. Common examples include autism spectrum disorder (ASD) and social anxiety disorder (SAD). Additionally, several disorders have social withdrawal as a secondary symptom; examples include schizophrenia, major depressive disorder (MDD) and substance use disorders. At present there are no approved medications that directly target social deficits, and drug-treatments for these disorders, where available, have at best limited efficacy.

Millions of people worldwide suffer from some form of mental, neurological or behavioural disorder. An extrapolation study by the National Institute of Mental Health (NIMH) suggests that 10 million people a year suffer from social phobia which amounts to the diagnosis of 1150 people every hour. Social dysfunction can manifest as a primary or secondary feature of a variety of disorders, such as ASD, SAD, MDD, schizophrenia and substance use disorders.

Anxiety disorders are common throughout the world, and are of the most common mental disorders in Australia. Social anxiety disorder (SAD), also known as social phobia, is the most common anxiety disorder and is understood to affect 1 in 10 Australians at some time in their lives, and approximately 5% of the population at any one time. Social anxiety is frequently co-morbid with, and frequently precedes the onset of, other psychiatric problems such as depression, schizophrenia and substance use disorders. Social withdrawal is also a very prominent feature of childhood neurodevelopmental disorders such as autism.

There are currently limited approved therapeutics that target mental illness associated with anti-social behaviour including autism spectrum disorder (ASD), generalised anxiety disorder (GAD) and social anxiety disorder (SAD). Additionally, several disorders have social withdrawal as a secondary symptom. Examples here include schizophrenia, major depressive disorder (MDD) and substance use disorders. Currently prescribed therapeutics (Selective serotonin reuptake inhibitors (SSRIs), serotonin and noradrenaline reuptake inhibitors (SNRIs), stimulants and antipsychotics) have at best limited efficacy, slow onset of action, poor compliance and vast side effect profiles. These pharmaceuticals lack modification of the core social deficits encountered in these disease states. Thus, the current available treatments for people suffering from social dysfunction are extremely limited.

New research suggests that a promising target for treating these diseases is the neuropeptide oxytocin (OT). Animal studies show that OT positively modulates a wide variety of social interactions, including maternal behaviour, courtship, sexual behaviour and peer-to-peer interaction. Results of human studies, in which OT is usually administered intranasally, show that OT can increase trust and co-operation, improve social memory and decrease social fear. Moreover, recent clinical trials indicated that administration of OT to a person with autism and social anxiety can restore some aspects of social functioning. The OT receptor therefore has immense potential for drug discovery aimed at alleviating serious psychiatric disorders. However, it is unlikely that intranasal OT will be an optimal therapeutic modality. OT is a cyclic peptide that does not survive primary metabolism, has a short physiological half-life and does not readily penetrate the blood brain barrier.

In view of the above, targeting the OT receptor has great potential for the treatment of multiple social dysfunctions. While a number of compounds have been identified which target the OT receptor these have a number of shortcomings. For example, many compounds cannot selectively target the OT receptor as the OT receptor has a high degree of homology with the vasopressin 1a receptor (V1aR), meaning that selectivity can be extremely challenging. Furthermore, as with OT, many of these compounds do not readily penetrate the blood brain barrier; and many are metabolically broken down into smaller fragments which can have a deleterious effect.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The present invention concerns compounds of Formula I:

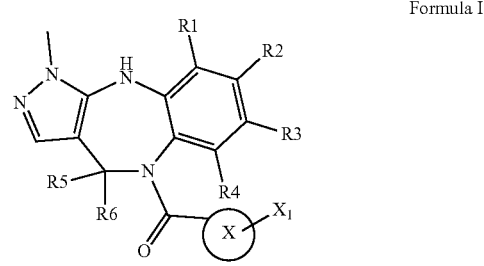

Formula I wherein R1, R3, R4, R5, or R6 are each independently selected from the group consisting of: H, F, Cl, Br, I, $NH_2$, $NO_2$, OH, ON=O, substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted $OC_1$-$C_4$ alkyl, substituted or unsubstituted $OC_2$-$C_4$ alkenyl, substituted or unsubstituted $OC_2$-$C_4$ alkynyl, substituted or unsubstituted $NHC_1$-$C_4$ alkyl, substituted or unsubstituted $NHC_2$-$C_4$ alkenyl, substituted or unsubstituted $NHC_2$-$C_4$ alkynyl, a substituted or unsubstituted aryl (such as a substituted or unsubstituted phenyl), or a substituted or unsubstituted heterocyclyl (such as a substituted or unsubstituted pyridyl, pyranyl, or thiopiranyl);

wherein R2 is independently selected from the group consisting of: H, F, Br, I, $NH_2$, $NO_2$, OH, ON=O, substituted methyl, substituted or unsubstituted $C_2$-$C_4$ alkyl, substituted or unsubstituted $C_2$-$C_4$ alkenyl, substituted or unsubstituted $C_2$-$C_4$ alkynyl, substituted or unsubstituted $OC_1$-$C_4$ alkyl, substituted or unsubstituted $OC_2$-$C_4$ alkenyl, substituted or unsubstituted $OC_2$-$C_4$ alkynyl, substituted or unsubstituted $NHC_1$-$C_4$ alkyl, substituted or unsubstituted $NHC_2$-$C_4$ alkenyl, substituted or unsubstituted $NHC_2$-$C_4$ alkynyl, a substituted or unsubstituted aryl (such as a substituted or unsubstituted phenyl), or a substituted or unsubstituted heterocyclyl (such as a substituted or unsubstituted pyridyl, pyranyl, or thiopiranyl);

wherein each R1, R2, R3, R4, R5, or R6 that is a substituted aryl or a substituted heterocyclyl includes one or more substituents selected from the group consisting of F, Cl, Br, I, $NH_2$, N=O, $NO_2$, $NHCH_3$, OH, $OCH_3$, OC≡N, ON=O, SH, $SCH_3$, $S(=O)_nOH$, $S(=O)_nCH_3$, SC≡N, COOH, $CH_3$, $CH_mF_{(3-m)}$, $CH_mCl_{(3-m)}$, $CH_mBr_{(3-m)}$, $OCH_3$, $OCH_mF_{(3-m)}$, $OCH_mCl_{(3-m)}$, or $OCH_mBr_{(3-m)}$;

wherein X is a cyclic structure selected from the group consisting of: a substituted or unsubstituted, fused or unfused aryl; a substituted or unsubstituted, fused or unfused heterocyclyl; or a substituted or unsubstituted, fused or unfused cycloalkyl; and wherein X1 represents one or more atoms or moieties independently selected from the group consisting of: F, Cl, Br, I, $NH_2$, $NO_2$, OH, ON=O, substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted $OC_1$-$C_4$ alkyl, substituted or unsubstituted $OC_2$-$C_4$ alkenyl, substituted or unsubstituted $OC_2$-$C_4$ alkynyl, substituted or unsubstituted $NHC_1$-$C_4$ alkyl, substituted or unsubstituted $NHC_2$-$C_4$ alkenyl, substituted or unsubstituted $NHC_2$-$C_4$ alkynyl, COOH, $C_1$ alkyl-COOH, $COOC_1$-$C_2$ alkyl, $COOC_1$-$C_2$ alkaryl, $C_1$ alkyl-$COOC_1$-$C_2$ alkyl, $C_1$-$C_2$ alkaryl, $OC_1$-$C_2$ alkaryl, $NC_1$-$C_2$ alkaryl, $C_1$-$C_2$ alkyl-heterocyclyl, $OC_1$-$C_2$ alkyl-heterocyclyl, $NC_1$-$C_2$ alkyl-heterocyclyl;

wherein each alkyl, alkenyl, alkynyl, alkaryl, alkyl-heterocyclyl that is substituted includes one or more substituents selected from the group consisting of: F, Cl, Br, I, ≡N, =NH, $NH_2$, N=O, $NO_2$, $NHCH_3$, N=C=O, N=C=S, =O, OH, $OCH_3$, OC≡N, ON=O, =S, SH, $SCH_3$, $S(=O)_nOH$, $S(=O)_nCH_3$, SC≡N, phenyl, pyridyl, pyranyl, or thiopiranyl (preferably said phenyl, pyridyl, pyranyl, or thiopiranyl are unsubstituted);

wherein each m is an integer selected from 0, 1, or 2; and each n is an integer selected from 0, 1, or 2.

It is preferred that when X1 is any one of a substituted or unsubstituted $C_1$-$C_4$ alkyl, or a substituted or unsubstituted $C_2$-$C_4$ alkenyl, the substituents are selected such that both =O and OH are not substituted on a terminal carbon atom in the alkyl or the alkenyl.

In an embodiment, R5 and R6 are each independently selected from H, F, Cl, Br, I, OH, $CH_3$, $CH_mF_{(3-m)}$, $CH_mCl_{(3-m)}$, $CH_mBr_{(3-m)}$, $OCH_3$, $OCH_mF_{(3-m)}$, $OCH_mCl_{(3-m)}$, or $OCH_mBr_{(3-m)}$; wherein each m is an integer selected from 0, 1, or 2. Preferably, at least one of R5 or R6 is H. More preferably. R5 and R6 are H.

In one form, the compound is of Formula IA:

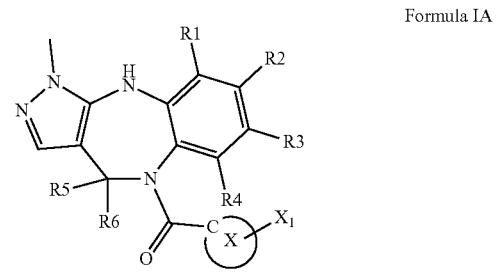

Formula IA

As used herein, the term "$C_1$-$C_4$ alkyl" either used alone or in compound terms refers to straight chain or branched saturated hydrocarbon groups, having 1 to 4 carbon atoms. Suitable alkyl groups include, but are not limited to: methyl, ethyl, propyl, isopropyl, n-butyl, sec-butyl, tert-butyl. The "$C_1$-$C_4$ alkyl" may be optionally substituted with one or more substituents. The substituents may replace one or more hydrogen atoms on any carbon atom or carbon atoms in the "$C_1$-$C_4$ alkyl" carbon atom chain.

As used herein, the term "$C_2$-$C_4$ alkenyl" either used alone or in compound terms refers to straight chain or branched unsaturated hydrocarbon groups, having 2 to 4 carbon atoms and including at least one carbon to carbon double bond. Suitable alkenyl groups include, but are not limited to: ethenyl, propenyl, or butenyl. The carbon to carbon double bond may be between any two adjacent carbon atoms. The "$C_2$-$C_4$ alkenyl" may be optionally substituted with one or more substituents. The substituents may replace one or more hydrogen atoms on any carbon atom or carbon atoms in the "$C_2$-$C_4$ alkenyl" carbon atom chain.

As used herein, the term "$C_2$-$C_4$ alkynyl" either used alone or in compound terms refers to straight chain or branched unsaturated hydrocarbon groups, having 2 to 4 carbon atoms and including at least one carbon to carbon triple bond. Suitable alkynyl groups include, but are not limited to: ethynyl, propynyl, or butynyl. The carbon to carbon triple bond may be between any two adjacent carbon atoms. The "$C_2$-$C_4$ alkynyl" may be optionally substituted with one or more substituents. The substituents may replace one or more hydrogen atoms on any carbon atom or carbon atoms in the "$C_2$-$C_4$ alkynyl" carbon atom chain.

In one form the cyclic structure 'X' is selected from the group consisting of: fused or unfused aryl groups; fused or unfused 5, 6, 7-membered heterocyclic groups having one or more hetero ring atoms selected from N, O, or S (preferably N); or a 5, 6, 7, 8, 9, 10, 11-, 12, 13, 14, 15-, or 16-membered (preferably 8, 9, 10, 11-, or 12-membered) mono-, bridged bi-, or bridged tri-cycloalkyl groups (preferably a bridged tri-cycloalkyl group). Bridged cycloalkyl groups are intended to cover prismanes and asteranes, such as prismane, cubane, basketane, etc. In forms of the invention where 'X' is a fused aryl group or a fused heterocyclic group, it is preferred that the fused group comprises 4 fused rings or less (preferably 3 fused rings or less, and more preferably 2 fused rings or less). The fused rings may be a mixture of one or more aryl, heterocyclyl, and/or cycloalkyl ring groups. In an alternate form of the invention, the aryl group and/or the heterocyclic group are unfused. It is preferred that the heterocyclic group is an unfused 5- or 6-membered heterocyclic group. More preferably the heterocyclic group has only a single hetero ring atom. Most preferably, the heterocyclic group is a pyridyl group. It is preferred that the cycloalkyl is a bridged bi- or bridged tri-cycloalkyl. It is preferred that the cycloalkyl group does not include a hetero ring atom. More preferably, the cycloalkyl is a bridged tri-cycloalkyl, and the most preferably the bridged tri-cycloalkyl is adamantyl. It is most preferred that the cyclic structure is selected from the group consisting of: phenyl, pyridyl, and adamantyl.

It is preferred that the compound is not selected from the group consisting of:

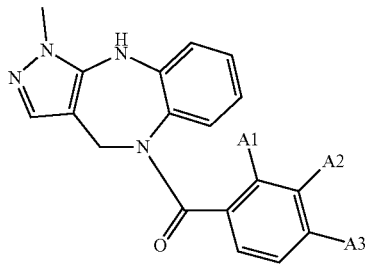

when A1 is H; A2 is $CH_3$; and A3 is any one of $CH_2CH_2COOH$, $CH=CHCOOH$, $OCH_2CH_2CH_2COOH$, $CH_2NH_2$, $CH_2CH_2C(=O)NHCH_3$, $C\equiv N$, $NH_2$, or $NO_2$; or when A1 is H; A2 is H; and A3 is OH; or when A1 is F, A2 is H, and A3 is $CH_2NH_2$.

It is preferred that the substituted or unsubstituted cycloalkyl is not a substituted cyclohexane group.

It is preferred that R1 and R4 are each independently selected from the group consisting of: H, F, Cl, Br, I, OH, $CH_3$, $CH_mF_{(3-m)}$, $CH_mCl_{(3-m)}$, $CH_mBr_{(3-m)}$, $OCH_3$, $OCH_mF_{(3-m)}$, $OCH_mCl_{(3-m)}$, or $OCH_mBr_{(3-m)}$. Alternatively, or additionally, it is preferred that R1 and R4 are the same. Most preferably, R1 and R4 are both H.

It is preferred that R2 is independently selected from the group consisting of: H, F, Br, I, OH, $CH_mF_{(3-m)}$, $CH_mCl_{(3-m)}$, $CH_mBr_{(3-m)}$, $OCH_3$, $OCH_mF_{(3-m)}$, $OCH_mCl_{(3-m)}$, or $OCH_mBr_{(3-m)}$. More preferably, R2 is H.

It is preferred that R3 is independently selected from the group consisting of: H, F, Cl, Br, I, OH, $CH_3$, $CH_mF_{(3-m)}$, $CH_mCl_{(3-m)}$, $CH_mBr_{(3-m)}$, $OCH_3$, $OCH_mF_{(3-m)}$, $OCH_mCl_{(3-m)}$, or $OCH_mBr_{(3-m)}$. More preferably, R3 is selected from the group consisting of: H, $CH_3$, or $OCH_3$.

It is preferred that at least two of R1, R2, R3, or R4 are H. More preferably, at least three of R1, R2, R3, or R4 are H.

In an embodiment, the substituted or unsubstituted aryl is a substituted or unsubstituted phenyl of the form:

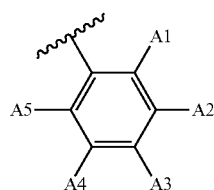

wherein each A1, A2, A3, A4, or A5 is independently selected from the group consisting of: H, F, Cl, Br, I, $NH_2$, $NO_2$, OH, ON=O, substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted $OC_1$-$C_4$ alkyl, substituted or unsubstituted $OC_2$-$C_4$ alkenyl, substituted or unsubstituted $OC_2$-$C_4$ alkynyl, substituted or unsubstituted $NHC_1$-$C_4$ alkyl, substituted or unsubstituted $NHC_2$-$C_4$ alkenyl, substituted or unsubstituted $NHC_2$-$C_4$ alkynyl; and wherein optionally one or more of A1 and A2, and/or A2 and A3, and/or A3 and A4, and/or A4 and A5 together form a fused ring structure. The fused ring structure may be a substituted or unsubstituted aryl, heterocyclyl, or cycloalkyl. In situations where this ring structure is substituted, it is preferred that the substituents are selected from the group consisting of: H, F, Cl, Br, I, $NH_2$, $NO_2$, OH, ON=O, substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted $OC_1$-$C_4$ alkyl, substituted or unsubstituted $OC_2$-$C_4$ alkenyl, substituted or unsubstituted $OC_2$-$C_4$ alkynyl, substituted or unsubstituted $NHC_1$-$C_4$ alkyl, substituted or unsubstituted $NHC_2$-$C_4$ alkenyl, substituted or unsubstituted $NHC_2$-$C_4$ alkynyl.

In a preferred form (i) A2 is not $CH_3$ when R1, R2, R3, R4, A1, A4, and A5 are each H; and A3 is any one of $CH_2CH_2COOH$, $CH=CHCOOH$, $OCH_2CH_2CH_2COOH$, $CH_2NH_2$, $CH_2CH_2C(=O)NHCH_3$, $C\equiv N$, $NH_2$, or $NO_2$; (ii) A4 is not $CH_3$ when R1, R2, R3, R4, A1, A2, and A5 are each H and A3 is any one of $CH_2CH_2COOH$, $CH=CHCOOH$, $OCH_2CH_2CH_2COOH$, $CH_2NH_2$, $CH_2CH_2C(=O)NHCH_3$, $C\equiv N$, $NH_2$, or $NO_2$; (iii) A3 is not OH when R1, R2, R3, R4, A1, A2, A4, and A5 are H; and (iv) A3 is not $CH_2NH_2$ when A1 is F, and R1, R2, R3, R4, A2, A4, and A5 are each H.

It is preferred that each A1, A2, A3, A4, or A5 is independently selected from the group consisting of: H, F, Cl, Br, I, $NH_2$, $NO_2$, OH, ON=O, substituted or unsubstituted $C_1$-$C_2$ alkyl, substituted or unsubstituted $C_2$ alkenyl, substituted or unsubstituted $C_2$ alkynyl, substituted or unsubstituted $OC_1$-$C_2$ alkyl, substituted or unsubstituted $OC_2$ alkenyl, substituted or unsubstituted $OC_2$ alkynyl, substituted or unsubstituted $NHC_1$-$C_2$ alkyl, substituted or unsubstituted $NHC_2$ alkenyl, substituted or unsubstituted $NHC_2$ alkynyl. More preferably each A1, A2, A3, A4, or A5 is independently selected from the group consisting of: H, F, Cl, Br, I, OH, $CH_3$, $CH_mF_{(3-m)}$, $CH_mCl_{(3-m)}$, $CH_mBr_{(3-m)}$, $OCH_3$, $OCH_mF_{(3-m)}$, $OCH_mCl_{(3-m)}$, or $OCH_mBr_{(3-m)}$.

It is preferred that at least two of A1, A2, A3, A4, or A5 is H. More preferably, at least three of A1, A2, A3, A4, or A5 is H.

In an embodiment, the substituted or unsubstituted heterocyclyl is a substituted or unsubstituted pyridyl selected from the group consisting of:

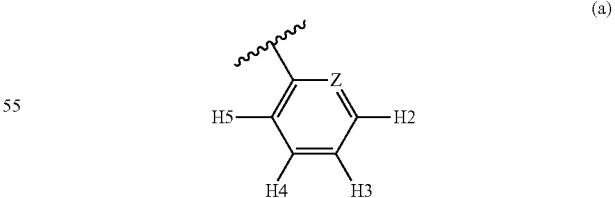

(a)

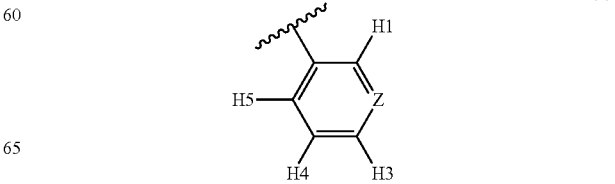

(b)

(c)

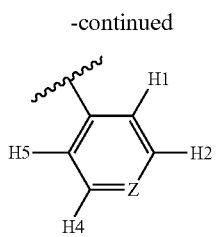

wherein Z is the hetero ring atom, and is selected from the group consisting of N, S, or O; and each H1, H2, H3, H4, or H5 that is present is independently selected from the group consisting of: H, F, Cl, Br, I, $NH_2$, $NO_2$, OH, ON=O, substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted $OC_1$-$C_4$ alkyl, substituted or unsubstituted $OC_2$-$C_4$ alkenyl, substituted or unsubstituted $OC_2$-$C_4$ alkynyl, substituted or unsubstituted $NHC_1$-$C_4$ alkyl, substituted or unsubstituted $NHC_2$-$C_4$ alkenyl, substituted or unsubstituted $NHC_2$-$C_4$ alkynyl; and wherein optionally one or more of H1 and H2, and/or H2 and H3, and/or H3 and H4, and/or H4 and H5 together form a fused ring structure. The fused ring structure may be a substituted or unsubstituted aryl, heterocyclyl, or cycloalkyl. In situations where this ring structure is substituted, it is preferred that the substituents are selected from the group consisting of: H, F, Cl, Br, I, $NH_2$, $NO_2$, OH, ON=O, substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted $OC_1$-$C_4$ alkyl, substituted or unsubstituted $OC_2$-$C_4$ alkenyl, substituted or unsubstituted $OC_2$-$C_4$ alkynyl, substituted or unsubstituted $NHC_1$-$C_4$ alkyl, substituted or unsubstituted $NHC_2$-$C_4$ alkenyl, substituted or unsubstituted $NHC_2$-$C_4$ alkynyl.

It is preferred that Z is selected from the group consisting of N or O. Most preferably, Z is N.

It is preferred that each H1, H2, H3, H4, or H5 that is present is independently selected from the group consisting of: H, F, Cl, Br, I, $NH_2$, $NO_2$, OH, ON=O, substituted or unsubstituted $C_1$-$C_2$ alkyl, substituted or unsubstituted $C_2$ alkenyl, substituted or unsubstituted $C_2$ alkynyl, substituted or unsubstituted $OC_1$-$C_2$ alkyl, substituted or unsubstituted $OC_2$ alkenyl, substituted or unsubstituted $OC_2$ alkynyl, substituted or unsubstituted $NHC_1$-$C_2$ alkyl, substituted or unsubstituted $NHC_2$ alkenyl, substituted or unsubstituted $NHC_2$ alkynyl. More preferably each H1, H2, H3, H4, or H5 that is present is independently selected from the group consisting of: H, F, Cl, Br, I, OH, $CH_3$, $CH_mF_{(3-m)}$, $CH_mCl_{(3-m)}$, $CH_mBr_{(3-m)}$, $OCH_3$, $OCH_mF_{(3-m)}$, $OCH_mCl_{(3-m)}$, or $OCH_mBr_{(3-m)}$.

It is preferred that at least two of each H1, H2, H3, H4, or H5 that is present is H. More preferably, at least three of each H1, H2, H3, H4, or H5 that is present is H. Most preferably, each H1, H2. H3, H4, or H5 that is present is H.

In an embodiment, the substituted or unsubstituted cycloalkyl is an adamantyl ring of the form:

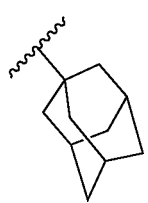 [SMILES: *C12CC3CC(CC(C3)C1)C2]

wherein each carbon atom in the adamantyl ring is unsubstituted (i.e. includes covalent bonds to only adjacent carbon ring atoms and hydrogen) or each carbon atom in the adamantyl ring that can be substituted may be substituted with one or more substituents selected from the group consisting of: H, F, Cl, Br, I, $NH_2$, $NO_2$, OH, ON=O, substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted $OC_1$-$C_4$ alkyl, substituted or unsubstituted $OC_2$-$C_4$ alkenyl, substituted or unsubstituted $OC_2$-$C_4$ alkynyl, substituted or unsubstituted $NH_4C_1$-$C_4$ alkyl, substituted or unsubstituted $NHC_2$-$C_4$ alkenyl, substituted or unsubstituted $NHC_2$-$C_4$ alkynyl.

It is preferred that each carbon atom in the adamantyl ring that can be substituted may be independently substituted with one or more substituents selected from the group consisting of: H, F, Cl, Br, I, $NH_2$, $NO_2$, OH, ON=O, substituted or unsubstituted $C_1$-$C_2$ alkyl, substituted or unsubstituted $C_2$ alkenyl, substituted or unsubstituted $C_2$ alkynyl, substituted or unsubstituted $OC_1$-$C_2$ alkyl, substituted or unsubstituted $OC_2$ alkenyl, substituted or unsubstituted $OC_2$ alkynyl, substituted or unsubstituted $NHC_1$-$C_2$ alkyl, substituted or unsubstituted $NHC_2$ alkenyl, substituted or unsubstituted $NHC_2$ alkynyl. More preferably each carbon atom in the adamantyl ring that can be substituted may be independently substituted with one or more substituents selected from the group consisting of: H, F, Cl, Br, I, OH, $CH_3$, $CH_mF_{(3-m)}$, $CH_mCl_{(3-m)}$, $CH_mBr_{(3-m)}$, $OCH_3$, $OCH_mF_{(3-m)}$ $OCH_mCl_{(3-m)}$, or $OCH_mBr_{(3-m)}$.

In an embodiment, the substituted or unsubstituted cycloalkyl is an adamantyl ring of the form:

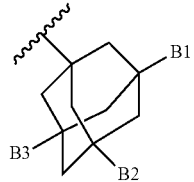

wherein each B1, B2, and B3 is independently selected from the group consisting of: H, F, Cl, Br, I, $NH_2$, $NO_2$, OH, ON=O, substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted $OC_1$-$C_4$ alkyl, substituted or unsubstituted $OC_2$-$C_4$ alkenyl, substituted or unsubstituted $OC_2$-$C_4$ alkynyl, substituted or unsubstituted $NHC_1$-$C_4$ alkyl, substituted or unsubstituted $NHC_2$-$C_4$ alkenyl, substituted or unsubstituted $NHC_2$-$C_4$ alkynyl; and wherein each other carbon atom in the adamantyl ring includes covalent bonds to only adjacent carbon ring atoms and hydrogen.

It is preferred that each B1, B2, and B3 is independently selected from the group consisting of: H, F, Cl, Br, I, $NH_2$, $NO_2$. OH, ON=O, substituted or unsubstituted $C_1$-$C_2$ alkyl, substituted or unsubstituted $C_2$ alkenyl, substituted or unsubstituted $C_2$ alkynyl, substituted or unsubstituted $OC_1$-$C_2$ alkyl, substituted or unsubstituted $OC_2$ alkenyl, substituted or unsubstituted $OC_2$ alkynyl, substituted or unsubstituted $NHC_1$-$C_2$ alkyl, substituted or unsubstituted $NHC_2$ alkenyl, substituted or unsubstituted $NHC_2$ alkynyl. More preferably each B1, B2, and B3 is independently selected from the group consisting of: H, F, Cl, Br, I, OH, $CH_3$, $CH_mF_{(3-m)}$, $CH_mCl_{(3-m)}$, $CH_mBr_{(3-m)}$, $OCH_3$, $OCH_mF_{(3-m)}$, $OCH_mCl_{(3-m)}$, or $OCH_mBr_{(3-m)}$.

It is preferred that at most two of B1, B2, or B3 is substituted.

In one form, the cyclic structure is the substituted or unsubstituted aryl group. In another form, the cyclic structure is the substituted or unsubstituted heterocyclyl. In yet another form, the cyclic structure is the substituted or unsubstituted cycloalkyl.

In view of the above, in a first aspect of the invention, there is provided a pharmaceutical composition, the pharmaceutical composition including, consisting essentially of, or consisting of: a pharmaceutically acceptable compound of Formula I (as defined above); and a pharmaceutically acceptable carrier, diluent, or excipient.

In a second aspect of the invention, there is provided a method including: administering a pharmaceutical composition including a compound of Formula I to a subject. It is preferred that the pharmaceutical composition further includes a pharmaceutically acceptable carrier, diluent, or excipient.

In an embodiment, the method includes administering the pharmaceutical composition to the subject in an amount effective to treat or prevent a condition in a subject. The condition may be a social dysfunction, such as social withdrawal, aggressiveness, an anti-social disorder, or an addiction to a substance. The condition may be a psychiatric disorder, such as an autistic spectrum disorder, a social anxiety disorder, a depressive disorder including major depressive disorder, or schizophrenia. The substance may be, for example, alcohol, cocaine, opiates, amphetamines, heroin, and nicotine.

In an embodiment, the method includes administering the pharmaceutical composition to a subject that suffers from, or is recovering from a substance abuse disorder; or a subject that is recovering from the substance abuse disorder and seeks to maintain ongoing abstinence from the substance.

In a third aspect, there is provided the use of a pharmaceutical composition including the compound of Formula 1 for treating or preventing a condition in a subject, and/or maintaining ongoing abstinence from a substance in the subject.

In a fourth aspect, there is provided the use of the compound of Formula I for the manufacture of a medicament for the treatment of a condition, wherein the condition is selected from the group consisting of: a social dysfunction including: social withdrawal, aggressiveness, an anti-social disorder, or an addiction to a substance; or a psychiatric disorder including: a social anxiety disorder, a depressive disorder including major depressive disorder, or schizophrenia; or a developmental disorder such as an autistic spectrum disorder.

In a fifth aspect of the invention, there is provided the compound of Formula I, wherein the compound is not selected from the group consisting of:

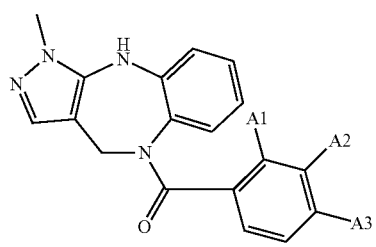

when A1 is H; A2 is $CH_3$; and A3 is any one of $CH_2CH_2COOH$, $CH=CHCOOH$, $OCH_2CH_2CH_2COOH$, $CH_2NH_2$, $CH_2CH_2C(=O)NHCH_3$, $C\equiv N$, $NH_2$, or $NO_2$; or when A1 is H; A2 is H; and A3 is OH; or when A1 is F, A2 is H, and A3 is $CH_2NH_2$; or a compound wherein the substituted or unsubstituted cycloalkyl is a substituted cyclohexane group.

Further aspects of the present invention and further embodiments of the aspects described in the preceding paragraphs will become apparent from the following description.

DETAILED DESCRIPTION OF THE EMBODIMENTS

Figure 1:
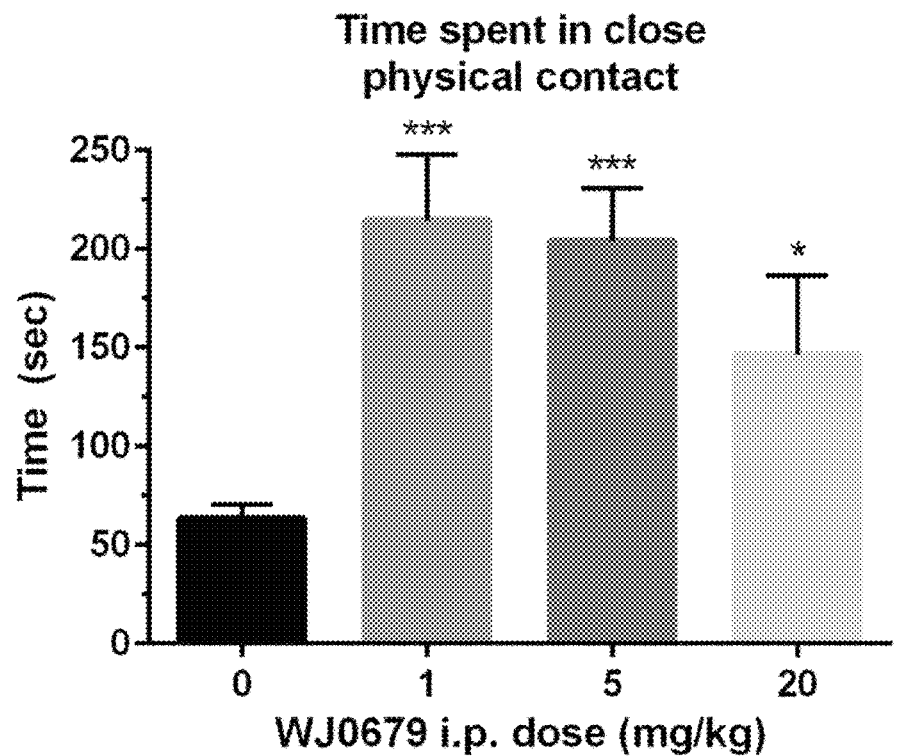
FIG. 1: Graph showing results of huddling time for mice treated with 0, 1, 5, and 20 mg/kg of a pharmaceutical composition including compound WJ0679.

The present invention is based on the discovery of compounds of Formula I and their use in treating a range of mental, neurological, and behavioural disorders. In particular, the compounds of Formula I have been found to act as selective agonists for the oxytocin receptor (OXTR).

Compounds exhibiting a head group that is structurally similar to compounds of Formula I are known, for example the WAY 267464 compound (see image below) is a non-peptide agonist for the oxytocin receptor.

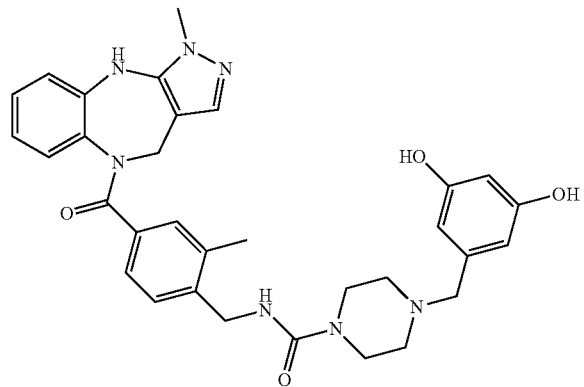

WAY 267,464

Furthermore, patent publications WO 2006/021213 and WO 03/000692 disclose vasopressin V1A antagonists and an oxytocin agonist respectively which exhibit similar architecture to the WAY 267,464 compound in that a number of the compounds disclosed therein include pyrazolo[1,4] diazepine head groups with long pendant chains extending from the nitrogen atom in the 4 position of the diazepine ring. However, these large compounds exhibit a number of draw backs in comparison with compounds of Formula I. For example, while these compounds can act as an OXTR agonist, these compounds also bind with the vasopressin V1a receptor (V1aR), generally as an antagonist. Other issues include poor bioavailability of these compounds, due to difficulties with these compounds crossing the blood brain barrier, or the metabolism of these compounds into smaller fragments which then have no effect or a deleterious effect.

Frantz et al. conducted a study in 2010 to systematically evaluate the structural determinants of the affinity and efficacy of representative ligands of the V1a, V2, and OT receptor subtypes (see Frantz et al. "*Subtlety of the Structure—Affinity and Structure—Efficacy Relationships around a Nonpeptide Oxytocin Receptor Agonist*", J. Med. Chem., 2010, 53, 1546-1562).

One of the compounds assessed by Frantz et al. was the compound below:

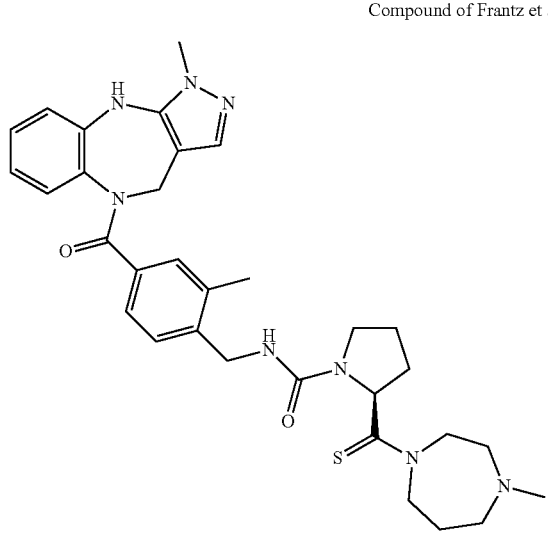

Compound of Frantz et al.

Frantz et al. divided this compound into a "western part" which covered only the pyrazolo[1,4] diazepine head group, and an "eastern part" which covered the tail group extending from the nitrogen atom in the 4 position of the diazepine ring. Frantz et al. then studied the effects of varying the head group of the "western part" and truncating the "eastern part" of the compound. Interestingly, Frantz et al. demonstrated that truncation of the "eastern part" of the overall molecule resulted in the molecule acting as an antagonist for the OXTR, or in some cases being inactive in respect of OXTR. Based on this, Frantz et al. concluded that a long tail including at least the urea linkage is necessary for the OXTR activation.

Surprisingly, the inventors have found that compounds of Formula I not only act as OXTR agonists, but in many instances are highly selective for the OXTR, having minimal or no affinity for V1aR. The compounds of Formula I, being comparatively small molecules, are also less susceptible to issues of bioavailability and metabolic breakdown that plague some of these larger molecules.

The compounds of Formula I act at the OXTR while avoiding a number of pitfalls associated with the native ligand (i.e. oxytocin) or the compounds discussed in WO 2006/021213, WO 03/000692, and Frantz et al. As such, the compounds avoid or reduce the problems mentioned above for OT and have widespread and valuable applications for a range of conditions or disorders that may be treated by an OXTR agonist. In addition to treating disease states, selective small molecules allow for molecular probes for the OT receptor.

In view of the above, the invention also relates to a pharmaceutical composition including the compound of Formula I. The compound of Formula I is included in a pharmaceutically effective amount, sufficient to produce a desired effect upon a process or condition of a disease.

An appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. The amount of a compound of the present invention in the composition will also depend upon the particular compound in the composition.

The pharmaceutical composition may further comprise other therapeutically active compounds which are usually applied in the treatment of the disclosed disorders or conditions. Selection of the appropriate agents for use in combination therapy may be made by one of ordinary skill in the art, according to conventional pharmaceutical principles. The combination of therapeutic agents may act synergistically to effect the treatment or prevention of the various disorders or conditions disclosed herein. Using this approach, one may be able to achieve therapeutic efficacy with lower dosages of each agent, thus reducing the potential for adverse side effects.

Compounds and compositions of the invention may be formulated for any appropriate route of administration including, for example, topical (for example, transdermal or ocular), oral, buccal, nasal, vaginal, rectal or parenteral administration. The term parenteral as used herein includes subcutaneous, intradermal, intravascular (for example, intravenous), intramuscular, spinal, intracranial, intrathecal, intraocular, periocular, intraorbital, intrasynovial and intraperitoneal injection, as well as any similar injection or infusion technique. In certain embodiments, compositions in a form suitable for oral use or parenteral use are preferred. Suitable oral forms include, for example, tablets, troches, lozenges, aqueous or oily suspensions, dispersible powders or granules, emulsions, hard or soft capsules, or syrups or elixirs. Within yet other embodiments, compositions provided herein may be formulated as a lyophilizate.

The various dosage units are each preferably provided as a discrete dosage tablet, capsules, lozenge, dragee, gum, or other type of solid formulation. Capsules may encapsulate a powder, liquid, or gel. The solid formulation may be swallowed, or may be of a suckable or chewable type (either frangible or gum-like). The present invention contemplates dosage unit retaining devices other than blister packs; for example, packages such as bottles, tubes, canisters, packets.

The dosage units may further include conventional excipients well-known in pharmaceutical formulation practice, such as binding agents, gellants, fillers, tableting lubricants, disintegrants, surfactants, and colorants; and for suckable or chewable formulations.

Compositions intended for oral use may further comprise one or more components such as sweetening agents, flavouring agents, colouring agents and/or preserving agents in order to provide appealing and palatable preparations. Tablets contain the active ingredient in admixture with physiologically acceptable excipients that are suitable for the manufacture of tablets. Such excipients include, for example, inert diluents such as calcium carbonate, sodium carbonate, lactose, calcium phosphate or sodium phosphate, granulating and disintegrating agents such as corn starch or alginic acid, binding agents such as starch, gelatine or acacia, and lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatine capsules wherein the active ingredient is mixed with an inert solid diluent such as calcium carbonate, calcium phosphate or kaolin, or as soft gelatine capsules wherein the active ingredient is mixed with water or an oil medium such as peanut oil, liquid paraffin or olive oil.

Aqueous suspensions contain the active ingredient(s) in admixture with excipients suitable for the manufacture of aqueous suspensions. Such excipients include suspending agents such as sodium carboxymethylcellulose, methylcellulose, hydroxypropylmethylcellulose, sodium alginate, polyvinylpyrrolidone, gum tragacanth and gum acacia, and dispersing or wetting agents such as naturally-occurring phosphatides (for example, lecithin), condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol mono-oleate, or condensation products of ethylene oxide with partial esters derived from fatty acids and hexitol anhydrides such as polyethylene sorbitan monooleate. Aqueous suspensions may also comprise one or more preservatives, for example ethyl, or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil such as arachis oil, olive oil, sesame oil or coconut oil, or in a mineral oil such as liquid paraffin. The oily suspensions may contain a thickening agent such as beeswax, hard paraffin or cetyl alcohol. Sweetening agents such as those set forth above, and/or flavouring agents may be added to provide palatable oral preparations. Such suspensions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavouring and colouring agents, may also be present.

Pharmaceutical compositions may also be in the form of oil-in-water emulsions. The oily phase may be a vegetable oil such as olive oil or arachis oil, a mineral oil such as liquid paraffin, or a mixture thereof. Suitable emulsifying agents include naturally-occurring gums such as gum acacia or gum tragacanth, naturally-occurring phosphatides such as soy bean lecithin, and esters or partial esters derived from fatty acids and hexitol, anhydrides such as sorbitan monoleate, and condensation products of partial esters derived from fatty acids and hexitol with ethylene oxide such as polyoxyethylene sorbitan monoleate. An emulsion may also comprise one or more sweetening and/or flavouring agents.

Syrups and elixirs may be formulated with sweetening agents, such as glycerol, propylene glycol, sorbitol or sucrose. Such formulations may also comprise one or more demulcents, preservatives, flavouring agents and/or colouring agents.

Compositions of the invention may be formulated for local or topical administration, such as for topical application to the skin. Formulations for topical administration typically comprise a topical vehicle combined with active agent(s), with or without additional optional components.

Suitable topical vehicles and additional components are well known in the art, and it will be apparent that the choice of a vehicle will depend on the particular physical form and mode of delivery. Topical vehicles include organic solvents such as alcohols (for example, ethanol, iso-propyl alcohol or glycerine), glycols such as butylene, isoprene or propylene glycol, aliphatic alcohols such as lanolin, mixtures of water and organic solvents and mixtures of organic solvents such as alcohol and glycerine, lipid-based materials such as fatty acids, acylglycerols including oils such as mineral oil, and fats of natural or synthetic origin, phosphoglycerides, sphingolipids and waxes, protein-based materials such as collagen and gelatine, silicone-based materials (both nonvolatile and volatile), and hydrocarbon-based materials such as microsponges and polymer matrices.

A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and Martin (ed.), Remington's Pharmaceutical Sciences. Formulations may comprise microcapsules, such as hydroxymethylcellulose or gelatine-microcapsules, liposomes, albumin microspheres, microemulsions, nanoparticles or nanocapsules.

A topical formulation may be prepared in a variety of physical forms including, for example, solids, pastes, creams, foams, lotions, gels, powders, aqueous liquids, emulsions, sprays and skin patches. The physical appearance and viscosity of such forms can be governed by the presence and amount of emulsifier(s) and viscosity adjuster(s) present in the formulation. Solids are generally firm and non-pourable and commonly are formulated as bars or sticks, or in particulate form. Solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity. Both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product. Gels can be prepared with a range of viscosities, from thick or high viscosity to thin or low viscosity. These formulations, like those of lotions and creams, may also contain solvents, emulsifiers, moisturizers, emollients, fragrances, dyes/colorants, preservatives and other active ingredients that increase or enhance the efficacy of the final product. Liquids are thinner than creams, lotions, or gels, and often do not contain emulsifiers. Liquid topical products often contain solvents, emulsifiers, moisturizers, emollients, fragrances, dyes/colorants, preservatives and other active ingredients that increase or enhance the efficacy of the final product.

Emulsifiers for use in topical formulations include, but are not limited to, ionic emulsifiers, cetearyl alcohol, non-ionic emulsifiers like polyoxyethylene oleyl ether, PEG-40 stearate, ceteareth-12, ceteareth-20, ceteareth-30, ceteareth alcohol, PEG-100 stearate and glyceryl stearate. Suitable viscosity adjusting agents include, but are not limited to, protective colloids or nonionic gums such as hydroxyethylcellulose, xanthan gum, magnesium aluminum silicate, silica, microcrystalline wax, beeswax, paraffin, and cetyl palmitate. A gel composition may be formed by the addition of a gelling agent such as chitosan, methyl cellulose, ethyl cellulose, polyvinyl alcohol, polyquaterniums, hydroxyethylcellulose, hydroxypropylcellulose, hydroxypropylmethylcellulose, carbomer or ammoniated glycyrrhizinate. Suitable surfactants include, but are not limited to, nonionic, amphoteric, ionic and anionic surfactants. For example, one or more of dimethicone copolyol, polysorbate 20, polysorbate 40, polysorbate 60, polysorbate 80, lauramide DEA, cocamide DEA, and cocamide MEA, oleyl betaine, cocamidopropyl phosphatidyl PG-diimonium chloride, and ammonium laureth sulfate may be used within topical formulations.

Preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerine, propylene glycol, and butylene glycol. Suitable emollients include lanolin alcohol, lanolin, lanolin derivatives, cholesterol, petrolatum, isostearyl neopentanoate and mineral oils. Suitable fragrances and colours include, but are not limited to, FD&C Red No. 40 and FD&C Yellow No. 5. Other suitable additional ingredients that may be included in a topical formulation include, but are not limited to, abrasives, absorbents, anticaking agents, antifoaming agents, antistatic agents, astringents (such as witch hazel), alcohol and herbal extracts such as chamomile extract, binders/excipients, buffering agents, chelating agents, film forming agents, conditioning agents, propellants, opacifying agents, pH adjusters and protectants.

Typical modes of delivery for topical compositions include application using the fingers, application using a physical applicator such as a cloth, tissue, swab, stick or brush, spraying including mist, aerosol or foam spraying, dropper application, sprinkling, soaking, and rinsing. Controlled release vehicles can also be used, and compositions may be formulated for transdermal administration (for example, as a transdermal patch).

Pharmaceutical compositions may be formulated as sustained release formulations such as a capsule that creates a slow release of modulator following administration. Such formulations may generally be prepared using well-known technology and administered by, for example, oral, rectal or subcutaneous implantation, or by implantation at the desired target site. Carriers for use within such formulations are biocompatible, and may also be biodegradable. Preferably, the formulation provides a relatively constant level of modulator release. The amount of modulator contained within a sustained release formulation depends upon, for example, the site of implantation, the rate and expected duration of release and the nature of the disorder to be treated or prevented.

In another form, the invention relates to a method of treating a subject, the method including administering a pharmaceutically effective amount of a compound of Formula I, in a pharmaceutically acceptable form, to the subject.

As used herein, a "subject" refers to an animal, such as a mammalian or an avian species, including a human, an ape, a horse, a cow, a sheep, a goat, a dog, a cat, a guinea pig, a rat, a mouse, a chicken etc.

The inventors have found that compounds of Formula I are particularly useful for the treatment of a range of neurological conditions or disorders. The condition or disorder may be a social dysfunction, such as social withdrawal, aggressiveness, an anti-social disorder, or an addiction to a substance (for example, alcohol, cocaine, opiates, amphetamines, heroin, and nicotine.). The condition or disorder may be a psychiatric disorder, a social anxiety disorder, a depressive disorder including major depressive disorder, memory loss, or schizophrenia, or a developmental disorder such as an autistic spectrum disorder. The condition or disorder may be a stress disorders including post-traumatic stress disorder.

As used herein, the terms "treating" and "treatment" may include one or more of, ameliorating a symptom of a disorder in a subject, blocking or ameliorating a recurrence of a symptom of a condition or disorder in a subject, and decreasing in severity and/or frequency a symptom of a condition or disorder in a subject.

In another aspect the present invention provides a kit or article of manufacture including a compound of Formula I or pharmaceutical composition including a compound of Formula I as described herein.

In other embodiments there is provided a kit for use in a therapeutic or prophylactic application mentioned herein, the kit including: a container holding a compound of Formula I or pharmaceutical composition including a compound of Formula I; and a label or package insert with instructions for use.

The kit or "article of manufacture" may comprise a container and a label or package insert on or associated with the container. Suitable containers include, for example, bottles, vials, syringes, blister pack, etc. The containers may be formed from a variety of materials such as glass or plastic. The container holds a compound of Formula I or composition which is effective for treating the condition and may have a sterile access port (for example the container may be an intravenous solution bag or a vial having a stopper pierceable by a hypodermic injection needle). The label or package insert indicates that the dendrimer or composition is used for treating a disorder. In one embodiment, the label or package insert includes instructions for use and indicates that the therapeutic or prophylactic composition can be used to treat a disorder described herein.

The kit may comprise (a) a therapeutic or prophylactic composition; and (b) a second container with a second active principle or ingredient contained therein. The kit in this embodiment of the invention may further comprise a package insert indicating the composition and other active principle can be used to treat a disorder or prevent a complication stemming from a disorder described herein. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain embodiments the therapeutic composition may be provided in the form of a device, disposable or reusable, including a receptacle for holding the compound of Formula I or therapeutic or prophylactic pharmaceutical composition including a compound of Formula I. In one embodiment, the device is a syringe. The therapeutic or prophylactic composition may be provided in the device in a state that is ready for use or in a state requiring mixing or addition of further components.

It will be understood that the invention disclosed and defined in this specification extends to all alternative combinations of two or more of the individual features mentioned or evident from the text. All of these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

All of the publications referred to herein are incorporated by reference in their entirety.

EXAMPLES

SYNTHETIC EXAMPLES

Example 1: General Procedure for the Amidation of Tricyclic 1 with Benzoic Acids of General Structure 2

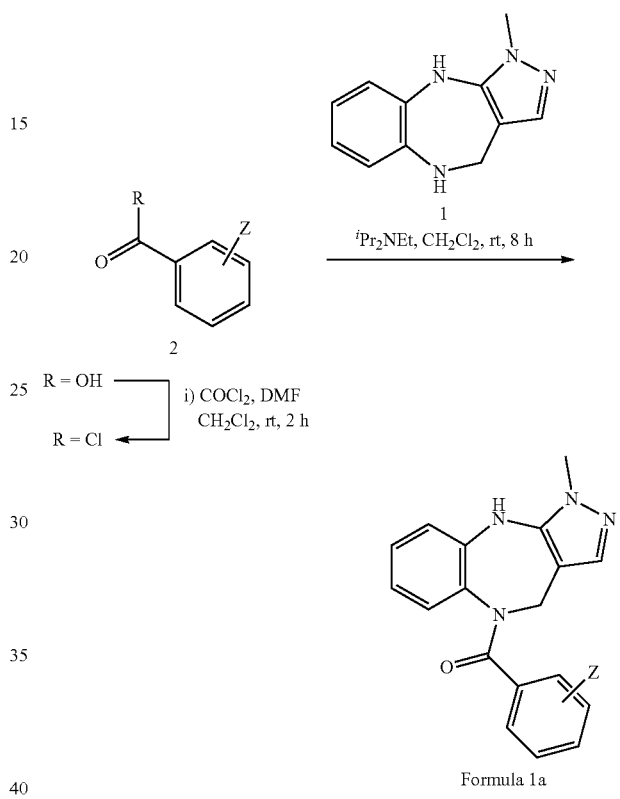

Method A:

Step i:

Acid chlorides were prepared by treating the parent acids (1.1 mmol) in CH$_2$Cl$_2$ (10 mL) at 0° C. with oxalyl chloride (1.0 mL, 11 mmol) followed by DMF (1 drop) and stirred at room temperature for 2 h followed by concentrating under a stream of nitrogen to afford acyl chlorides of general structure (2).

Step ii:

A magnetically stirred suspension of 1 (200 mg, 1 mmol) and NEt$_3$ (229 µL, 2 mmol) in CH$_2$Cl$_2$ (10 mL) was treated with a solution of the appropriate benzoyl chlorides (1.1 mmol) in CH$_2$Cl$_2$ (10 mL) dropwise at 0° C. The reaction mixture was then warmed to room temperature and stirring continued for 4 h. The resultant solution was diluted with CH$_2$Cl$_2$ (25 mL) and NaHCO$_3$ (25 mL of a sat. aq. solution), the separated organic phase was subsequently washed with NaHCO$_3$ (25 mL of a sat. aq. solution) and brine (50 mL) before being dried (MgSO$_4$), filtered and concentrated under reduced pressure to give crude oils (of compounds of the Formula 1a). Purification by either trituration (EtOAc) followed by recrystallisation (MeOH/CH$_2$Cl$_2$) or via flash chromatography afforded the required amides.

Method B:

An ice cold magnetically stirred solution of the required benzoic acid (1.1 mmol), amine 1 (200 mg, 1 mmol) and $^i$Pr$_2$NEt (348 µL, 2 mmol) in CH$_2$Cl$_2$ (20 mL) was treated with PyBOP® (500 mg, 1 mmol) in portions, allowed to warm to room temperature and stirring continued for 4 h. The reaction mass was diluted with CH$_2$Cl$_2$ (50 mL) and water (50 mL), the separated organic phase was subsequently washed with NaHCO$_3$ (25 mL of a sat. aq. solution) and brine (100 mL) before being dried (MgSO$_4$), filtered and purified via flash column chromatography (silica, 1:1 to 1:0 v/v EtOAc/hexanes gradient elution) produced the required amides as crystalline solids.

Method C:

Step i:

Acid chlorides were prepared by treating the parent acids (1.1 mmol) in CH$_2$Cl$_2$ (10 mL) at 0° C. with oxalyl chloride (1.0 mL, 11 mmol) followed by DMF (1 drop) and stirred at room temperature for 2 h followed by concentrating under a stream of nitrogen to afford acyl chlorides of general structure (2).

Step ii:

A magnetically stirred suspension of the dihydrochloride salt of 1 (272 mg, 1 mmol) and base (3.3 mmol) in CH$_2$Cl$_2$ (10 mL) was treated with a solution of the appropriate benzoyl chlorides (1.1 mmol) in CH$_2$Cl$_2$ (10 mL) dropwise at 0° C. The base may be NEt$_3$, diisopropylethylamine or pyridine. The reaction mixture was then warmed to room temperature and stirring continued for 4 h. The resultant solution was diluted with CH$_2$Cl$_2$ (25 mL) and NaHCO$_3$ (25 mL of a sat. aq. solution), the separated organic phase was subsequently washed with NaHCO$_3$ (25 mL of a sat. aq. solution) and brine (50 mL) before being dried (MgSO$_4$), filtered and concentrated under reduced pressure to give crude oils (of compounds of the Formula 1a). Purification by either trituration (EtOAc) followed by recrystallisation (MeOH/CH$_2$Cl$_2$) or via flash chromatography afforded the required amides.

Example 2: (1-Methyl-4,10-dihydrobenzo[b]pyrazolo[3,4-e][1,4]diazepin-5 (1H)-yl)(phenyl)methanone [WJ0685]

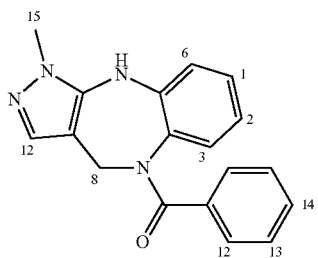

Treating diazepine 1 (150 mg, 0.75 mmol) with benzoyl chloride (174 µL, 1.5 mmol) according to the above general procedure A followed by purification via flash column chromatography (silica, 0.25:2.25:97.5 to 0.5:4.5:95 v/v/v 28% aq. ammonia/MeOH/CH$_2$Cl$_2$ gradient elution) produced WJ0685 (124 mg, 54%) as a white powder (R$_f$=0.23 in a 1:9:90 v/v/v 28% aq. ammonia/MeOH/CH$_2$Cl$_2$ solution).

$^1$H NMR (500 MHz, DMSO-d$_6$): δ 8.62 (br s, 1H, NH), 7.27 (dd, J=8.1, 1.4 Hz, 1H, 3-CH), 7.24-7.20 (m, 1H, 6-CH), 7.18 (s, 1H, 12-CH), 7.19-7.14 (m, 4H, 12/13-4× CH), 7.12-7.06 (m, 1H, 2-CH), 6.71 (dd, J=7.9, 1.5 Hz, 1H, 1-CH), 6.61 (t, J=7.8 Hz, 1H, 14-CH), 5.68 (d, J=14.5 Hz, 1H, 8-CH$_2$), 3.91 (d, J=14.4 Hz, 1H, 8-CH$_2$), 3.77 (s, 3H, 15-CH$_3$). $^{13}$C NMR (126 MHz, DMSO-d$_6$): δ 168.3, 139.8, 138.9, 136.4, 135.6, 132.3, 130.4, 129.4, 128.2, 127.7, 127.2, 121.1, 119.5, 100.3, 43.1, 35.4. IR (diamond cell, neat) ν$_{max}$: 3041, 1619, 1562, 1504, 1450, 1397, 1320, 1141, 990, 827, 797, 759, 727, 697, 648, 598, 446 cm$^{-1}$. LRMS (+ESI) m/z: 327 [(M+Na)$^+$, 100%], 631 [(2M+Na)$^+$, 45%]. HRMS (+ESI) Found: (M+Na)$^+$, 327.1214. C$_{18}$H$_{16}$N$_4$O requires (M+Na)$^+$, 327.1216. MP>300° C. HPLC purity: 98.33%, RT: 18.01 min.

Example 3: (3,5-Difluorophenyl)(1-methyl-4,10-dihydrobenzo[b]pyrazolo[3,4-e][1,4]diazepin-5 (1H)-yl)methanone [WJ0681]

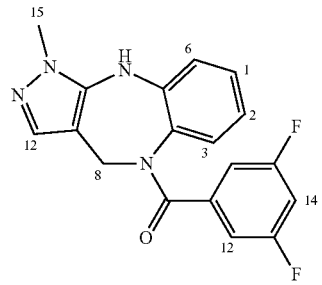 [SMILES: Cn1ncc2c1Nc1ccccc1N(C(=O)c1cc(F)cc(F)c1)C2]

Treating diazepine 1 (200 mg, 1 mmol) with the acid chloride derived from 3,5-difluorobenzoic acid (237 ing, 1.5 mmol) according to the above general procedure A followed by purification via trituration (EtOAc) and recrystallisation (MeOH/CH$_2$Cl$_2$) produced WJ0681 (141 mg, 41%) as a pale yellow needles (R$_f$=0.24 in a 1:9:90 v/v/v 28% aq. ammonia/MeOH/CH$_2$Cl$_2$ solution).

$^1$H NMR (400 MHz, DMSO-d$_6$): δ 8.66 (br s, 1H, NH), 7.28 (dd, J=8.2, 1.4 Hz, 1H, 3-CH), 7.19 (s, 1H, 12-CH), 7.18-7.09 (m, 2H, 2/6-2×CH), 6.90-6.78 (m, 3H, 12/14-3× CH), 6.69 (td, J=7.6, 1.4 Hz, 1H, 1-CH), 5.63 (d, J=14.5 Hz, 1H, 8-CH$_2$), 3.97 (d, J=14.5 Hz, 1H, 8-CH$_2$), 3.78 (s, 3H, 15-CH$_3$). $^{13}$C NMR (101 MHz, DMSO-d$_6$): δ 165.8, 161.6 (dd, J=12.7 Hz), 139.9 (t, J=8.9 Hz), 139.6, 139.1, 135.6, 131.5, 130.3, 128.8, 121.3, 119.6, 110.4 (d, J=26.5 Hz), 104.8 (t, J=25.8 Hz), 99.9, 43.2, 35.4. $^{19}$F NMR (376 MHz, DMSO-d$_6$): δ −109.50. IR (diamond cell, neat) ν$_{max}$: 3325, 1626, 1595, 1564, 1505, 1444, 1405, 1329, 1245, 1178, 1131, 991, 951, 862, 845, 801, 757, 726, 697, 665, 630, 564, 495, 448 cm$^{-1}$. LRMS (+ESI) m/z: 363 [(M+Na)$^+$, 100%], 703 [(2M+Na)$^+$, 26%]. HRMS (+ESI) Found: (M+Na)$^+$, 363.1024. C$_{18}$H$_{14}$F$_2$N$_4$O requires (M+Na)$^+$, 363.1028. MP 290-292° C. (decomp). HPLC purity: 96.65%, RT: 19.92 min.

Example 4: (3-Fluoro-4-methylphenyl)(1-methyl-4,10-dihydrobenzo[b]pyrazolo[3,4-e][1,4]diazepin-5(1H)-yl)methanone [WJ0683])

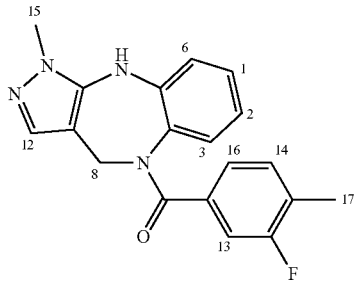 [SMILES: Cc1ccc(C(=O)N2Cc3cnn(C)c3Nc3ccccc32)cc1F]

Treating diazepine 1 (200 mg, 1 mmol) with the acid chloride derived from 3-fluoro-4-methylbenzoic acid (231 mg, 1.5 mmol) according to the above general procedure A followed by purification via flash column chromatography (silica. 0.25:2.25:97.5 to 0.5:4.5:95 v/v/v 28% aq. ammonia/MeOH/CH$_2$Cl$_2$ gradient elution) produced WJ0683 (137 mg, 41%) as colourless cubes (R$_f$=0.21 in a 1:9:90 v/v/v 28% aq. ammonia/MeOH/CH$_2$Cl$_2$ solution).

$^1$H NMR (500 MHz, DMSO-d$_6$): δ 8.64 (br s, 1H, NH), 7.29 (dd, J=8.1, 1.4 Hz, 1H, 3-CH), 7.17 (s, 1H, 12-CH), 7.13 (td, J=7.7, 1.6 Hz, 1H, 2-CH), 7.07 (t, J=7.7 Hz, 1H, 14-CH), 6.88-6.86 (m, 2H, 13/16-2×CH), 6.76 (dd, J=7.9, 1.6 Hz, 1H, 6-CH), 6.66 (td, J=7.6, 1.4 Hz, 1H, 1-CH), 5.66 (d, J=14.5 Hz, 1H, 8-CH$_2$), 3.92 (d, J=14.5 Hz, 1H, 8-CH$_2$), 3.77 (s, 3H, 15-CH$_3$), 2.12 (d, J=1.8 Hz, 3H, 17-CHs). $^{13}$C NMR (126 MHz, DMSO-d$_6$): δ 166.8, 159.6 (d, J=243.3 Hz), 139.8, 138.9, 135.9 (d, J=7.1 Hz), 135.6, 132.1, 130.9 (d, J=5.2 Hz), 130.3, 128.5, 125.8 (d, J=17.0 Hz), 123.3, 121.3, 119.6, 113.9 (d, J=23.8 Hz), 100.2, 43.2, 35.4, 14.0, $^{19}$F NMR (471 MHz, DMSO-d$_6$): δ –117.72. IR (diamond cell, neat) ν$_{max}$: 3294, 1623, 1557, 1501, 1392, 1302, 1252, 989, 822, 768, 730, 699, 628, 568, 495, 446 cm$^{-1}$. LRMS (+ESI) m/z: 359 [(M+Na)$^+$, 100%], 695 [(2M+Na)$^+$, 21%]. HRMS (+ESI) Found: (M+Na)$^+$, 359.1277. C$_{19}$H$_{17}$FN$_4$O requires (M+Na)$^+$, 359.1279. MP 235-237° C. HPLC purity: 97.99%, RT: 19.94 min.

Example 5: (1-Methyl-4,10-dihydrobenzo[b]pyrazolo[3,4-e][1,4]diazepin-5(1H)-yl)(p-tolyl)methanone [WJ0653]

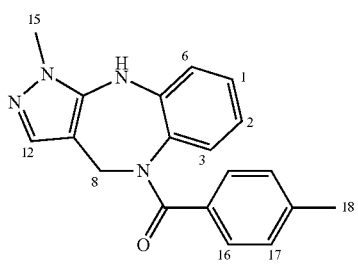 [SMILES: Cc1ccc(C(=O)N2Cc3cnn(C)c3Nc3ccccc32)cc1]

Treating diazepine 1 (200 mg, 1 mmol) with the acid chloride derived from 4-toluic acid (240 mg, 1.5 mmol) according to the above general procedure A followed by purification via trituration (EtOAc) and recrystallisation (MeOH) produced WJ0653 (95 mg, 30%) as a white solid (R$_f$=0.21 in a 1:9:90 v/v/v 28% aq. ammonia/MeOH/CH$_2$Cl$_2$ solution).

$^1$H NMR (400 MHz, DMSO-d$_6$): δ 8.59 (br s, 1H, NH), 7.39-7.22 (m, 1H, 3-CH), 7.16 (s, 1H, 12-CH), 7.10 (t, J=7.4 Hz, 1H, 2-CH), 7.04 (d, J=7.8 Hz, 2H, 16-2×CH), 6.96 (d, J=7.9 Hz, 2H, 17-2×CH), 6.69 (d, J=7.7 Hz, 1H, 6-CH), 6.63 (t, J=7.5 Hz, 1H, 1-CH), 5.68 (d, J=14.5 Hz, 1H, 8-CH$_2$), 3.89 (d, J=14.5 Hz, 1H, 8-CH$_2$). 3.77 (s, 3H, 15-CH$_3$), 2.19 (s, 3H, 18-CH$_3$). $^{13}$C NMR (101 MHz, DMSO-d$_6$): δ 168.1, 139.8, 139.1, 138.8, 135.6, 133.4, 132.5, 130.4, 128.2, 128.1, 127.5, 121.2, 119.5, 100.4, 43.1, 35.3, 20.8. IR (diamond cell, neat) ν$_{max}$: 3313, 1617, 1557, 1501, 1389, 1293, 1251, 1140, 1023, 989, 832, 767, 753, 730, 707, 627, 597, 490, 441 cm$^{-1}$. LRMS (+ESI) m/z: 319 [(M+H)$^+$, 10%] 341 [(M+Na)$^+$, 100%], 659 [(2M+Na)$^+$, 36%]. HRMS (+ESI) Found: (M+Na)$^+$, 341.1370. C$_{19}$H$_{18}$N$_4$O requires (M+Na)$^+$, 341.1373. MP 265° C. (decomp). HPLC purity: 96.48%, RT: 19.04 min.

Example 6: (4-Chlorophenyl)(1-methyl-4,10-dihydrobenzo[b]pyrazolo[3,4-e][1,4]diazepin-5(1H)-yl)methanone [WJ0755]

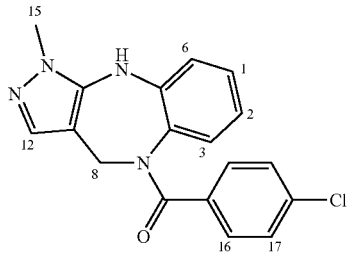

Treating diazepine 1 (200 mg, 1 mmol) with the acid chloride derived from 4-chlorobenzoic acid (172 mg, 1.1 mmol) according to the above general procedure A followed by purification via flash column chromatography (silica, 0.25:2.25:97.5 to 0.5:4.5:95 v/v/v 28% aq. ammonia/MeOH/CH$_2$Cl$_2$ gradient elution) produced WJ0755 (187 mg, 55%) as yellow cubics (R$_f$=0.31 in a 1:9:90 v/v/v 28% aq. ammonia/MeOH/CH$_2$Cl$_2$ solution).

$^1$H NMR (500 MHz, DMSO-d$_6$): δ 8.62 (br s, 1H, NH), 7.28 (dd, J=8.2, 1.4 Hz, 1H, 3-CH), 7.26-7.20 (m, 2H, 2/12-2×CH), 7.20-7.05 (m, 4H, 16/17-4×CH), 6.75 (dd, J=7.9, 1.5 Hz, 1H, 6-CH, 6.68-6.58 (m, 1H, 1-CH), 5.66 (d, J=14.5 Hz, 1H, 8-CH$_2$), 3.93 (d, J=14.5 Hz, 1H, 8-CH$_2$), 3.77 (s, 3H, 15-CH$_3$). $^{13}$C NMR (126 MHz, DMSO-d$_6$): δ 167.2, 139.7, 138.9, 135.7, 135.3, 134.0, 131.9, 130.4, 129.1, 128.5, 127.8, 121.2, 119.6, 100.3, 43.2, 35.4. IR (diamond cell, neat) ν$_{max}$: 3319, 1623, 1560, 1504, 1453, 1408, 1296, 1245, 1137, 1088, 1015, 989, 843, 827, 764, 753, 700, 628, 595, 553, 489 cm$^{-1}$. LRMS (+ESI) m/z: 339 [(M+H)$^+$, 50%]361 [(M+Na)$^+$, 100%]. HRMS (+ESI) Found: (M+H)$^+$, 339.1008. C$_{18}$H$_{15}$ClN$_4$O requires (M+H)$^+$, 339.1007. MP 243-246° C. HPLC purity: 96.01%, RT: 19.95 min.

Example 7: (1-Methyl-4,10-dihydrobenzo[b]pyrazolo[3,4-e][1,4]diazepin-5 (1H)-yl)(4-(trifluoromethyl)phenyl)methanone [WJ0677]

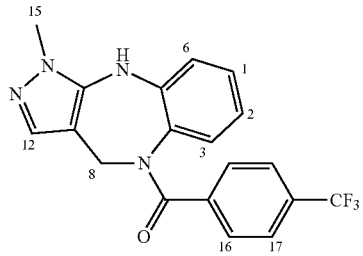

Treating diazepine 1 (200 mg, 1 mmol) with the acid chloride derived from 4-trifluoromethylbenzoic acid (285 mg, 1.5 mmol) according to the above general procedure A followed by purification via flash column chromatography (silica, 0.25:2.25:97.5 to 0.5:4.5:95 v/v/v 28% aq. ammonia/MeOH/$CH_2Cl_2$ gradient elution) produced WJ0677 (221 mg, 59%) as an off-white powder ($R_f$=0.27 in a 1:9:90 v/v/v 28% aq. ammonia/MeOH/$CH_2Cl_2$ solution).

$^1$H NMR (500 MHz, DMSO-$d_6$): δ 8.64 (br s, 1H, NH), 7.54 (d, J=8.2 Hz, 2H, 16-2×CH), 7.35 (d, J=8.0 Hz, 2H, 17-2×CH), 7.28 (dd, J=8.2, 1.4 Hz, 1H, 3-CH), 7.20 (s, 1H, 12-CH), 7.11 (ddd, J=8.3, 7.2, 1.5 Hz, 1H, 2-CH), 6.79 (dd, J=7.8, 1.5 Hz, 1H, 6-CH), 6.62 (td, J=7.6, 1.4 Hz, 1H, 1-CH), 5.67 (d, J=14.5 Hz, 1H, 8-$CH_2$), 3.97 (d, J=14.4 Hz, 1H, 8-$CH_2$), 3.78 (s, 3H, 15-$CH_3$). $^{13}$C NMR (126 MHz, DMSO-$d_6$): δ 167.1, 140.6, 139.7, 139.0, 135.7, 131.4, 130.5, 129.3 (q, J=31.9 Hz), 128.6, 127.9, 124.7 (q, J=3.9 Hz), 123.4 (q, J=273.3 Hz). 121.1, 119.5, 100.2, 43.2, 35.4. $^{19}$F NMR (471 MHz, DMSO-$d_6$): δ −61.33. IR (diamond cell, neat) $v_{max}$: 3319, 1641, 1557, 1503, 1387, 1321, 1252, 1167, 1111, 1066, 1020, 992, 845, 757, 732, 681, 630, 610, 496, 418 cm$^{-1}$. LRMS (+ESI) m/z: 395 [(M+Na)$^+$, 100%], 767 [(2M+Na)$^+$, 24%]. HRMS (+ESI) Found: (M+Na)$^+$, 395.1086. $C_{19}H_{15}F_3N_4O$ requires (M+Na)$^+$, 395.1090. MP 204-206° C. HPLC purity: 96.68%, RT: 21.21 min.

Example 8: 3,5-Bis(benzyloxy)benzoic acid

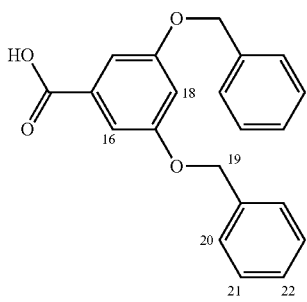 [SMILES: O=C(O)c1cc(OCc2ccccc2)cc(OCc2ccccc2)c1]

Step i:

A magnetically stirred suspension of resorcylic acid (616 mg, 4.0 mmol) and $K_2CO_3$ (2.76 g, 20 mmol) in DMF (15 mL) was treated with benzyl bromide (0.96 mL, 16 mmol) and stirring continued for 3 h. The reaction volume was diluted with EtOAc (75 mL), washed with water (3×50 mL), brine (100 mL) and the organic phase dried ($MgSO_4$), filtered and concentrated under reduced pressure. The resultant ester was used immediately in step ii.

Step ii:

A magnetically stirred solution of the benzyl ester (1.27 g, 3.0 mmol) in MeOH (10 mL) was treated with NaOH (10 mL of a 2 M aq. solution) and brought to reflux for 1 h. The resultant reaction volume was concentrated under reduced pressure and washed with ether (50 mL). The aq. phase was acidified to pH 2 (HCl, 4M aq. solution) and extracted with $CH_2Cl_2$ (2×25 mL). The combined chlorinated layers were washed with brine (100 mL), dried ($MgSO_4$), filtered and concentrated under reduced pressure to give 3,5-Bis(benzyloxy)benzoic acid (1 g, quant.) as colourless crystals. The spectral data for this compound, is identical in all aspects with those previously reported in Fuse S. Otake Y, Mifune Y, Tanaka H: A Facile Preparation of alpha-Aryl Carboxylic Acid via One-Flow Arndt-Eistert Synthesis. Aust J Chem 2015, 68(11):1657-1661 (a copy of which is hereby incorporated by reference).

Example 9: (3,5-Bis(benzyloxy)phenyl)(1-methyl-4,10-dihydrobenzo[b]pyrazolo[3,4-e][1,4]diazepin-5 (1H)-yl)methanone

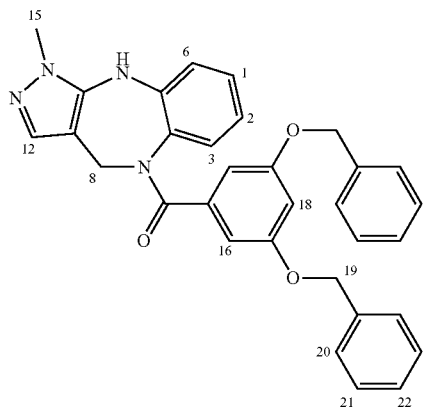 [SMILES: Cn1ncc2c1Nc1ccccc1N(C(=O)c1cc(OCc3ccccc3)cc(OCc3ccccc3)c1)C2]

Treating diazepine 1 (400 mg, 2 mmol) with the acid chloride derived from 3,5-dibenzyloxybenzoic acid (670 mg, 2 mmol) according to the above general procedure A followed by purification via flash column chromatography (silica, 0.25:2.25:97.5 to 0.5:4.5:95 v/v/v 28% aq. ammonia/MeOH/$CH_2Cl_2$ gradient elution) produced (3,5-Bis(benzyloxy)phenyl)(1-methyl-4,10-dihydrobenzo[b]pyrazolo[3,4-e][1,4]diazepin-5 (1H)-yl)methanone (480 mg, 47%) as a white powder ($R_f$=0.37 in a 1:9:90 v/v/v 28% aq. ammonia/MeOH/$CH_2Cl_2$ solution).

$^1$H NMR (300 MHz, DMSO-$d_6$) δ 8.63 (br s, 1H, NH), 7.55-7.25 (m, 11H, Ar—H), 7.22-7.06 (m. 2H, 1/3-2×CH), 6.82-6.60 (m, 2H, 2/6-2×CH), 6.51 (t, J=2.3 Hz, 1H, 18-CH), 6.39 (d, J=2.3 Hz, 2H, 16-2×CH), 5.64 (d, J=14.6 Hz, 1H, 8-$CH_2$), 4.91 (q, J=12.0 Hz, 4H, 19-2×$CH_2$), 3.91 (d, J=14.5 Hz, 1H, 8-$CH_2$), 3.77 (s, 3H, 15-$CH_3$). $^{13}$C NMR (75 MHz, DMSO-$d_6$): δ 167.6, 158.6, 139.7, 139.0, 138.1, 136.7, 135.6, 132.4, 130.1, 128.4, 128.3, 127.9, 127.6, 121.4, 119.4, 106.4, 103.0, 100.1, 69.3, 43.0, 35.4. IR (diamond cell, neat) $v_{max}$: 3317, 1642, 1638, 1543, 1513, 1387, 1322, 1251, 1166, 1119, 1061, 1020, 992, 848, 753, 731, 677, 628, 496, 428 cm$^{-1}$. LRMS (+ESI) m/z: 517 [(M+H)$^+$, 100%], 1033 [(2M+H)$^+$, 28%]. HRMS (+ESI)

Found: (M+Na)$^+$, 539.2053. C$_{32}$H$_{28}$N$_4$O$_3$ requires (M+Na)$^+$, 539.2054. MP 221-224° C.

Example 10: (3,5-Dihydroxyphenyl)(1-methyl-4,10-dihydrobenzo[b]pyrazolo[3,4-e][1,4]diazepin-5(1H)-yl)methanone [WJ0623]

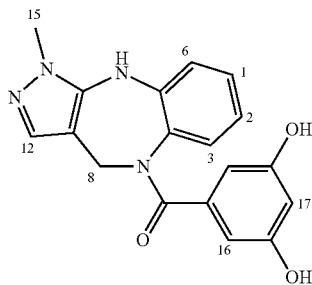 [SMILES: Cn1ncc2c1Nc1ccccc1N(C(=O)c1cc(O)cc(O)c1)C2]

A magnetically stirred suspension of the product from Example 9 (270 mg, 0.5 mmol) and Pd/C (27 mg of a 10% w/w) in MeOH (10 mL) was placed under an atmosphere of hydrogen (1 atm) for 16 h. The resulting mixture was filtered through Celite® and the solids thus retained were washed with MeOH (3×20 mL). The combined filtrates were concentrated under reduced pressure and purified by flash column chromatography (silica, 9:1 v/v CH$_2$Cl$_2$/MeOH) and concentration of the relevant fractions (R$_f$=0.11 in a 1:9 v/v MeOH/CH$_2$Cl$_2$ solution) produced WJ0623 (116 mg, 69%) as a white powder.

$^1$H NMR (300 MHz, DMSO-d$_6$): δ 9.26 (br s, 2H, 2×OH), 8.55 (br s, 1H, NH), 7.27 (d, J=8.1 Hz, 1H, 3-CH), 7.22-7.03 (m. 2H, 2/12-2×CH), 6.71-6.66 (m, 2H, 1/6-2×CH), 6.07 (s, 1H, 17-CH), 6.05-5.90 (m, 2H, 16-2×CH), 5.61 (d, J=14.5 Hz, 1H, 8-CH$_2$), 3.84 (d, J=14.5 Hz, 1H, 8-CH$_2$). 3.77 (s, 3H, 15-CH$_3$). $^{13}$C NMR (75 MHz, DMSO-d$_6$): δ 168.4, 157.6, 139.9, 138.6, 138.2, 135.7, 132.3, 130.1, 128.1, 121.1, 119.5, 105.7, 103.6, 100.5, 43.1, 35.4. IR (diamond cell, neat) ν$_{max}$: 3293, 1626, 1567, 1503, 1446, 1396, 1295, 1250, 1169, 1145, 1004, 940, 833, 803, 754, 723, 696, 570, 497, 447 cm$^{-1}$. LRMS (+ESI) m/z: 337 [(M+H)$^+$, 100%]. HRMS (+ESI) Found: (M+H)$^+$, 337.1296. C$_{18}$H$_{16}$N$_4$O$_3$ requires (M+H)$^+$, 337.1295. MP>300° C. HPLC purity: 96.31%, RT: 19.48 min.

Example 11: (3,5-Dimethoxyphenyl)(1-methyl-4,10-dihydrobenzo[b]pyrazolo[3,4-e][1,4]diazepin-5(1H)-yl)methanone [WJ0629]

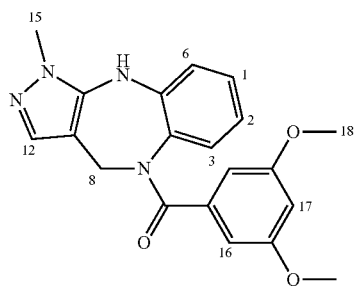 [SMILES: COc1cc(OC)cc(C(=O)N2Cc3cnn(C)c3Nc3ccccc32)c1]

Treating diazepine 1 (200 mg, 1 mmol) with the acid chloride derived from 3,5-dimethoxybenzoic acid (273 mg, 1.5 mmol) according to the above general procedure A followed by purification via flash column chromatography (silica. 0.25:2.25:97.5 to 0.5:4.5:95 v/v/v 28% aq. ammonia/MeOH/CH$_2$Cl$_2$ gradient elution) produced WJ0629 (247 mg, 68%) as a white powder (R$_f$=0.32 in a 1:9:90 v/v/v 28% aq. ammonia/MeOH/CH$_2$Cl$_2$ solution).

$^1$H NMR (300 MHz, DMSO-d$_6$): δ 8.64 (br s, 1H, NH), 7.28 (d, J=8.1 Hz, 1H, 3-CH), 7.23-6.99 (m, 2H, 2/12-2×CH), 6.75-6.65 (m, 2H, 1/17-2×CH), 6.30-6.24 (m, 3H, 16/6-3×CH), 5.65 (d, J=14.5 Hz, 1H, 8-CH$_2$), 3.91 (d, J=14.5 Hz, 1H, 8-CH$_2$), 3.77 (s. 3H, 15-CH$_3$), 3.59 (s, 6H, 18-2×CH3). $^{13}$C NMR (75 MHz, DMSO-d$_6$): δ 167.8, 159.6, 139.9, 139.1, 138.1, 135.7, 132.6, 130.1, 128.3, 121.4, 119.5, 105.4, 101.4, 100.2, 55.1, 43.1, 35.4. IR (diamond cell, neat) ν$_{max}$: 3322, 1594, 1558, 1505, 1451, 1426, 1394, 1290, 1247, 1206, 1155, 1052, 986, 928, 834, 765, 722, 696, 630, 540, 494, 441 cm$^{-1}$. LRMS (+ESI) m/z: 365 [(M+H)$^+$, 100%]. HRMS (+ESI) Found: (M+H)$^+$, 365.1609. C$_{20}$H$_{20}$N$_4$O$_3$ requires (M+H)$^+$, 365.1608. MP 279-281° C. (decomp). HPLC purity: 96.37%, RT: 18.99 min.

Example 12: (3-Methoxyphenyl)(1-methyl-4,10-dihydrobenzo[b]pyrazolo[3,4-e][1,4]diazepin-5(1H)-yl)methanone [WJ0657]

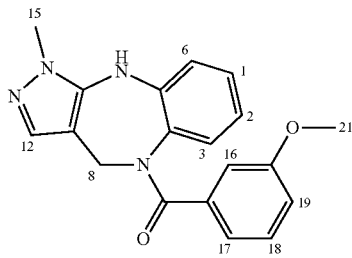 [SMILES: COc1cccc(C(=O)N2Cc3cnn(C)c3Nc3ccccc32)c1]

Treating diazepine 1 (200 mg, 1 mmol) with the acid chloride derived from 3-methoxybenzoic acid (228 mg, 1.5 mmol) according to the above general procedure A followed by purification via trituration (EtOAc) and recrystallisation (MeOH) produced WJ0657 (112 mg, 33%) as a white fluffy powder (R$_f$=0.28 in a 1:9:90 v/v/v 28% aq. ammonia/MeOH/CH$_2$Cl$_2$ solution).

$^1$H NMR (500 MHz, DMSO-d$_6$): δ 8.63 (br s, 1H, NH), 7.28 (dd, J=8.2, 1.4 Hz, 1H, 3-CH), 7.18 (s, 1H, 12-CH), 7.15-7.03 (m, 2H, 2/19-2×CH), 6.78 (dd, J=8.2, 2.6 Hz, 1H, 6-CH), 6.77-6.71 (m, 2H, 17/18-2×CH), 6.71-6.67 (m, 1H, 16-CH), 6.64 (td, J=7.5, 1.4 Hz, 1H, 1-CH), 5.67 (d, J=14.5 Hz, 1H, 8-CH$_2$), 3.91 (d, J=14.5 Hz, 1H, 8-CH$_2$), 3.78 (s, 3H, 15-CHs), 3.60 (s, 3H, 21-CH$_3$). $^{13}$C NMR (126 MHz, DMSO-d$_6$): δ 167.9, 158.3, 139.8, 139.0, 137.6, 135.6, 132.4, 130.3, 128.8, 128.3, 121.3, 119.6, 119.5, 115.2, 112.6, 100.3, 54.9, 43.1, 35.4. IR (diamond cell, neat) ν$_{max}$: 3292, 1621, 1563, 1504, 1450, 1391, 1318, 1294, 1238, 1173, 1121, 1049, 984, 877, 833, 800, 757, 731, 694, 648, 567, 498, 447 cm$^{-1}$. LRMS (+ESI) m/z: 357 [(M+Na)$^+$, 100%], 691 [(2M+Na)$^+$, 44%]. HRMS (+ESI) Found: (M+Na)$^+$, 357.1319. C$_{19}$H$_{18}$N$_4$O$_2$ requires (M+Na)$^+$, 357.1322. MP 267-269° C. (decomp). HPLC purity: 98.82%, RT: 18.51 min.

Example 13: (2-Methoxyphenyl)(1-methyl-4,10-dihydrobenzo[b]pyrazolo[3,4-e][1,4]diazepin-5 (1H)-yl)methanone [WJ0659]

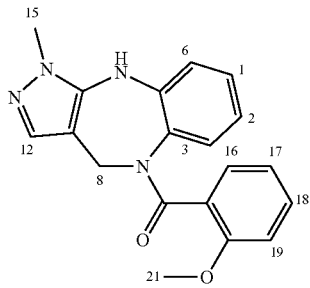 [SMILES: COc1ccccc1C(=O)N1Cc2cnn(C)c2Nc2ccccc21]

Treating diazepine 1 (200 mg, 1 mmol) with the acid chloride derived from 2-methoxybenzoic acid (228 mg, 1.5 mmol) according to the above general procedure A followed by purification via trituration (EtOAc) and recrystallisation (MeOH) produced WJ0659 (144 mg, 43%) as a white powder ($R_f$=0.22 in a 1:9:90 v/v/v 28% aq. ammonia/MeOH/CH$_2$Cl$_2$ solution).

$^1$H NMR (400 MHz, DMSO-d$_6$): δ 8.54 (br s, 1H, NH), 7.26-7.08 (m, 4H, 2/3/4/12-3×CH), 6.99 (t, J=8.0 Hz, 1H, 1-CH), 6.74 (br s, 3H, 16/18/19-3×CH), 6.60-6.38 (m, 1H, 17-CH), 5.57 (d, J=14.4 Hz, 1H, 8-CH$_2$), 3.88 (d, J=14.4 Hz, 1H, 8-CH$_2$), 3.77 (s, 3H, 15-CH), 3.57 (s, 3H, 21-CH). $^{13}$C NMR (101 MHz, DMSO-d$_6$): δ 166.9, 154.8, 139.9, 138.8, 135.6, 130.7, 129.9, 129.5, 127.9, 126.5, 120.3, 119.7, 119.0, 111.4, 110.7, 100.6, 55.0, 42.5, 35.3. IR (diamond cell, neat) $v_{max}$: 3287, 1626, 1561, 1506, 1495, 1459, 1400, 1321, 1247, 1110, 1022, 828, 754, 739, 733, 642, 600 cm$^{-1}$. LRMS (+ESI) m/z: 357 [(M+Na)$^+$, 100%], 691 [(2M+Na)$^+$, 24%]. HRMS (+ESI) Found: (M+Na)$^+$, 357.1318. C$_{19}$H$_{18}$N$_4$O$_2$ requires (M+Na)$^+$, 357.1322. MP 281-282° C. (decomp). HPLC purity: 98.53%, RT: 17.68 min.

Example 14: (4-Methoxyphenyl)(1-methyl-4,10-dihydrobenzo[b]pyrazolo[3,4-e][1,4]diazepin-5 (1H)-yl)methanone [WJ0661]

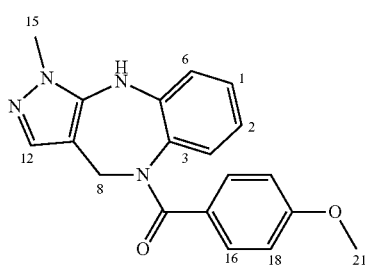 [SMILES: COc1ccc(C(=O)N2Cc3cnn(C)c3Nc3ccccc32)cc1]

Treating diazepine 1 (200 mg, 1 mmol) with the acid chloride derived from 4-methoxybenzoic acid (228 mg, 1.5 mmol) according to the above general procedure A followed by purification via trituration (EtOAc) and recrystallisation (MeOH) produced WJ0661 (212 mg. 63%) as white needles ($R_f$=0.19 in a 1:9:90 v/v/v 28% aq. ammonia/MeOH/CH$_2$Cl$_2$ solution).

$^1$H NMR (500 MHz, DMSO-d$_6$): δ 8.58 (br s, 1H, NH), 7.29 (dd, J=8.2, 1.3 Hz, 1H, 3-CH), 7.23-7.00 (m, 4H, 1/2/6/12-4×CH), 6.85-6.53 (m, 4H, 16/18-4×CH), 5.68 (d, J=14.6 Hz, 1H, 8-CH$_2$), 3.88 (d, J=14.6 Hz, 1H, 8-CH$_2$). 3.76 (s, 3H, 15-CH$_3$), 3.68 (s, 3H, 21-CH$_3$). $^{13}$C NMR (126 MHz, DMSO-d$_6$): δ 167.7, 160.0, 139.9, 138.7, 135.6, 132.7, 130.3, 129.5, 128.2, 128.1, 121.3, 119.6, 112.9, 100.5, 55.1, 43.2, 35.3. IR (diamond cell, neat) $v_{max}$: 3285, 1619, 1561, 1503, 1444, 1390, 1299, 1254, 1178, 1143, 1117, 1022, 987, 850, 828, 792, 756, 731, 643, 607, 494, 441 cm$^{-1}$. LRMS (+ESI) m/z: 357 [(M+Na)$^+$, 100%], 691 [(2M+Na)$^+$], 27% ]. HRMS (+ESI) Found: (M+Na)$^+$, 357.1319. C$_{19}$H$_{18}$N$_4$O$_2$ requires (M+Na)$^+$, 357.1322. MP 296-298° C. (decomp). HPLC purity: 97.47%, RT: 18.89 min.

Example 15: (3-Fluorophenyl)(1-methyl-4,10-dihydrobenzo[b]pyrazolo[3,4-e][1,4]diazepin-5 (1H)-yl)methanone [WJ0679]

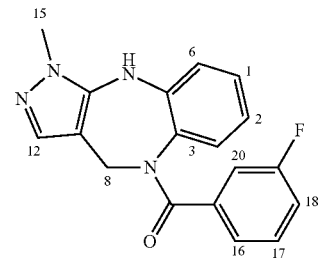

Treating diazepine 1 (200 mg, 1 mmol) with the acid chloride derived from 3-fluorobenzoic acid (210 mg, 1.5 mmol) according to the above general procedure A followed by purification via flash column chromatography (silica, 0.25:2.25:97.5 to 0.5:4.5:95 v/v/v 28% aq. ammonia/MeOH/CH$_2$Cl$_2$ gradient elution) produced WJ0679 (221 mg, 69%) as a white powder ($R_f$=0.25 in a 1:9:90 v/v/v 28% aq. ammonia/MeOH/CH$_2$Cl$_2$ solution).

$^1$H NMR (500 MHz, DMSO-d$_6$): 8.64 (br s, 1H, NH), 7.27 (dd, J=8.2, 1.4 Hz, 1H, 3-CH), 7.25-7.20 (m, 1H, 20-CH), 7.19 (s, 1H, 12-CH), 7.12 (ddd, J=8.2, 7.3, 1.6 Hz, 1H, 16-CH), 7.07 (td, J=8.4, 2.3 Hz, 1H, 2-CH), 6.97 (dt, J=7.7, 1.2 Hz, 1H, 17-CH), 6.93 (ddd, J=9.5, 2.7, 1.4 Hz, 1H, 18-CH), 6.79 (dd, J=7.8, 1.5 Hz, 1H, 6-CH), 6.65 (td, J=7.6, 1.4 Hz, 1H, 1-CH), 5.65 (d, J=14.5 Hz, 1H, 8-CH$_2$), 3.94 (d, J=14.4 Hz, 1H, 8-CH$_2$). 3.77 (s, 3H, 15-CH$_3$). $^{13}$C NMR (126 MHz, DMSO-d$_6$): δ 166.9, 161.2 (d, J=244.4 Hz), 139.8, 139.0, 138.7 (d, J=7.4 Hz), 135.7, 131.9, 130.4, 129.9 (d, J=7.9 Hz), 128.5, 123.3, 121.3, 119.6, 116.3 (d, J=20.7 Hz). 114.1 (d, J=22.9 Hz), 100.1, 43.2, 35.4. $^{19}$F NMR (471 MHz, DMSO-d$_6$): δ −113.2. IR (diamond cell, neat) $v_{max}$: 3319, 1624, 1564, 1504, 1453, 1404, 1300, 1246, 1177, 992, 873, 837, 818, 796, 758, 730, 691, 630, 562, 498, 451, 419 cm 1. LRMS (+ESI) m/z: 345 [(M+Na)$^+$, 100%], 667 [(2M+Na)$^+$, 46%]. HRMS (+ESI) Found: (M+Na)$^+$, 345.1119. C$_{18}$H$_{14}$FN$_4$O requires (M+Na)$^+$, 345.1122. MP 286-288° C. (decomp). HPLC purity: 98.21%, RT: 18.94 min.

Example 16: (1-Methyl-4,10-dihydrobenzo[b]pyrazolo[3,4-e][1,4]diazepin-5 (1H)-yl)(m-tolyl)methanone [WJ0823]

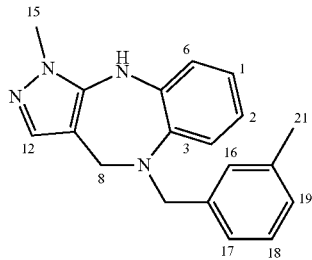 [SMILES: Cn1ncc2c1Nc1ccccc1N(C(=O)c1cccc(F)c1)C2]

Treating diazepine 1 (100 mg, 0.5 mmol) with the acid chloride derived from 3-toluic acid (82 mg, 0.6 mmol) according to the above general procedure A followed by purification via trituration (EtOAc) and column chromatography (silica, 0.25:2.25:97.5 to 0.5:4.5:95 v/v/v 28% aq. ammonia/MeOH/CH$_2$Cl$_2$ gradient elution) produced WJ0823 (87 mg, 55%) as a white crystalline solid ($R_f$=0.22 in a 1:9:90 v/v/v 28% aq. ammonia/MeOH/CH$_2$Cl$_2$ solution).

$^1$H NMR (400 MHz, DMSO-d$_6$): δ 8.61 (br s, 1H, NH), 7.34-7.21 (m, 1H, 3-CH), 7.17 (s, 1H, 12-CH), 7.10 (t, J=7.6 Hz, 1H, 2-CH), 7.01-6.91 (m, 3H, 16/18/19-3×CH), 6.87 (d, J=7.3 Hz, 1H, 17-CH), 6.70 (d, J=7.3 Hz, 1H, 6-CH), 6.62 (t, J=7.5 Hz, 1H, 1-CH), 5.67 (d, J=14.5 Hz, 1H, 8-CH$_2$), 3.90 (d, J=14.5 Hz, 1H, 8-CH$_2$), 3.77 (s, 3H, 15-CH$_3$), 2.16 (s, 3H, 21-CH$_3$). $^{13}$C NMR (101 MHz, DMSO-d$_6$): δ 168.3, 139.8, 138.9, 136.9, 136.3, 135.6, 132.4, 130.3, 130.0, 128.2, 128.0, 127.4, 124.3, 121.1, 119.4, 100.3, 43.0, 35.3, 20.8. IR (diamond cell, neat) $v_{max}$: 3325, 1621, 1561, 1558, 1506, 1444, 1408, 1321, 1247, 1178, 1131, 985, 951, 862, 845, 801, 808, 756, 649, 607, 492, 441 cm$^{-1}$. LRMS (+ESI) m/z: 341 [(M+Na)$^+$, 100%] HRMS (+ESI) Found: (M+H)$^+$, 319.1555. C$_{19}$H$_{18}$N$_4$O requires (M+H)$^+$, 319.1553. MP 254-256° C. HPLC purity: 96.31%, RT: 19.48 min.

Example 17: (3,4-Dimethylphenyl)(1-methyl-4,10-dihydrobenzo[b]pyrazolo[3,4-e][1,4]diazepin-5 (1H)-yl)methanone [WJ05103]

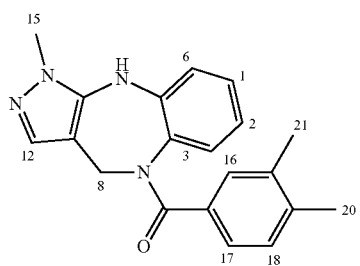 [SMILES: Cc1ccc(C(=O)N2Cc3cnn(C)c3Nc3ccccc32)cc1C]

Treating diazepine 1 (150 mg, 0.75 mmol) with the acid chloride derived from 3,4-dimethylbenzoic acid (125 mg, 0.82 mmol) according to the above general procedure A followed by purification via flash column chromatography (silica, 0.25:2.25:97.5 to 0.5:4.5:95 v/v/v 28% aq. ammonia/MeOH/CH$_2$Cl$_2$ gradient elution) produced WJ05103 (121 mg, 49%) as a white powder ($R_f$=0.21 in a 1:9:90 v/v/v 28% aq. ammonia/MeOH/CH$_2$Cl$_2$ solution).

$^1$H NMR (500 MHz, DMSO-d$_6$): 8.60 (s, 1H, NH), 7.31-7.24 (m, 1H, 3-CH), 7.16 (s, 1H, 12-CH), 7.10 (t, J=7.3 Hz, 1H, 2-CH), 7.03 (s, 1H, 16-CH), 6.86 (d, J=7.8 Hz, 1H, 6-CH), 6.77 (d, J=7.7 Hz, 1H, 17-CH), 6.69 (d, J=7.7 Hz, 1H, 18-CH), 6.63 (t, J=7.5 Hz, 1H, 1-CH), 5.67 (d, J=14.5 Hz, 1H, 8-CH$_2$), 3.88 (d, J=14.5 Hz, 1H, 8-CH$_2$), 3.77 (s, 3H, 15-CH$_3$), 2.10 (s, 3H, 20-CH$_3$), 2.07 (s, 3H, 21-CH$_3$). $^{13}$C NMR (126 MHz, DMSO-d$_6$): δ 168.2, 139.9, 138.9, 137.9, 135.6, 135.6, 133.7, 132.7, 130.3, 128.9, 128.5, 128.1, 124.9, 121.3, 119.5, 100.4, 43.1, 35.4, 19.2, 19.2. IR (diamond cell, neat) $v_{max}$: 3281, 1618, 1557, 1499, 1440, 1413, 1378, 1314, 1253, 1172, 990, 834, 811, 768, 754, 727, 696, 629, 610, 563, 489, 445 cm$^{-1}$. LRMS (+ESI) m/z: 333 [(M+H)$^+$, 51%], 665 [(2M+H)$^+$, 100%]. HRMS (+ESI) Found: (M+Na)$^+$, 333.1707. C$_{20}$H$_{20}$N$_4$O requires (M+H)$^+$, 333.1710. MP 254-256° C. (decomp). HPLC purity: 97.86%, RT: 19.89 min.

Example 18: (3,4-Dichlorophenyl)(1-methyl-4,10-dihydrobenzo[b]pyrazolo[3,4-e][1,4]diazepin-5 (1H)-yl)methanone [WJ0824]

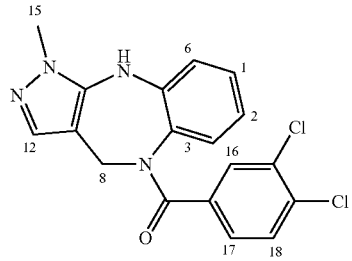

Treating diazepine 1 (100 mg, 0.5 mmol) with the acid chloride derived from 3,4-dichlorobenzoic acid (100 mg, 0.52 mmol) according to the above general procedure A followed by purification via flash column chromatography (silica, 0.25:2.25:97.5 to 0.5:4.5:95 v/v/v 28% aq. ammonia/ MeOH/CH$_2$Cl$_2$ gradient elution) produced WJ0824 (139 mg, 75%) as a yellow powder ($R_f$=0.20 in a 1:9:90 v/v/v 28% aq. ammonia/MeOH/CH$_2$Cl$_2$ solution).

$^1$H NMR (500 MHz, DMSO-d$_6$): 8.67 (s, 1H, NH), 7.45 (d, J=8.4 Hz, 1H, 18-CH), 7.35 (d, J=2.0 Hz, 1H, 16-CH), 7.30 (dd, J=8.2, 1.4 Hz, 1H, 3-CH), 7.19 (s, 1H, 12-CH), 7.15 (td, J=8.3, 7.8, 1.6 Hz, 1H, 2-CH), 7.08 (dd, J=8.3, 2.0 Hz, 1H, 17-CH), 6.83 (dd, J=7.9, 1.5 Hz, 1H, 6-CH), 6.69 (ddd, J=8.2, 7.3, 1.3 Hz, 1H, 1-CH), 5.64 (d, J=14.5 Hz, 1H, 8-CH$_2$), 3.95 (d, J=14.4 Hz, 1H, 8-CH$_2$), 3.77 (s, 3H, 15-CH$_3$). $^{13}$C NMR (126 MHz, DMSO-d$_6$): δ 165.9, 139.7, 139.0, 136.9, 135.7, 132.0, 131.5, 130.6, 130.4, 130.0, 129.3, 128.7, 127.4, 121.3, 119.6, 100.0, 43.3, 35.4. IR (diamond cell, neat) vax: 3260, 1637, 1557, 1504, 1387, 1367, 1296, 1242, 1122, 1031, 999, 835, 751, 719, 612, 552, 526, 435 cm$^{-1}$. LRMS (−ESI) m/z: 371/373 [(M−H)$^−$, 100/68%]. HRMS (+ESI) Found: (M+H)$^+$, 373.0620/ 375.0589. C$_{18}$H$_{14}$C$_{12}$N$_4$O requires (M+H)$^+$, 373.0617/ 375.0588. MP 263 264° C. (decomp). HPLC purity: 99.84%. RT: 22.87 min.

Example 19: ((3r,5r,7r)-Adamantan-1-yl)(1-methyl-4,10-dihydrobenzo[b]pyrazolo[3,4-e][1,4]diazepin-5(1H)-yl)methanone [WJ0687]

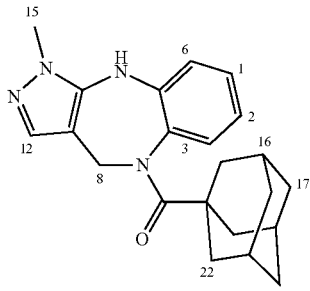 [SMILES: Cn1ncc2c1Nc1ccccc1N(C(=O)C13CC4CC(CC(C4)C1)C3)C2]

Treating diazepine 1 (150 mg, 0.75 mmol) with the acid chloride derived from adamantane carboxylic acid (270 mg, 1.5 mmol) according to the above general procedure B followed by purification via trituration (EtOAc) followed by recrystallisation from MeOH produced WJ0687 (201 mg, 78%) as white needles ($R_f$=0.28 in a 1:9:90 v/v/v 28% aq. ammonia/MeOH/CH$_2$Cl$_2$ solution).

$^1$H NMR (400 MHz, DMSO-d$_6$): 8.42 (s, 1H, NH), 7.36-7.27 (m, 2H, 3/2-2×CH), 7.26-7.19 (m, 1H, 6-CH), 7.05 (s, 1H, 12-CH), 7.03-6.95 (m, 1H, 1-CH), 5.44 (d, J=14.3 Hz, 1H, 8-CH$_2$), 3.69 (s, 31, 15-CH$_3$), 3.60 (d, J=14.3 Hz, 1H, 8-CH$_2$), 1.83-1.66 (m, 6H, 22-3×CH$_2$), 1.58-1.43 (m, 6H, 17-3×CH$_2$), 1.52-1.37 (m, 3H, 16-3×CH). $^{13}$C NMR (101 MHz, DMSO-d$_6$): δ 175.1, 140.5, 139.2, 135.8, 133.2, 130.9, 128.9, 121.4, 120.2, 100.6, 46.3, 43.0, 39.3, 35.9, 35.2, 27.8. IR (diamond cell, neat) $v_{max}$: 3276, 2901, 1614, 1555, 1499, 1435, 1376, 1276, 1248, 1175, 988, 837, 759, 725, 646, 590, 500, 445 cm 1. LRMS (+ESI) m/z: 363 [(M+H)$^+$, 11%], 385 [(M+Na)$^+$, 100%]. HRMS (+ESI) Found: (M+Na)$^+$, 385.1995. C$_{22}$H$_{26}$N$_4$O requires (M+Na)$^+$, 385.1999. MP 283-285° C. HPLC purity: 99.47%, RT: 21.90 min.

Example 20: ((1r,3s,5R,7S)-3-Fluoroadamantan-1-yl)(1-methyl-4,10-dihydrobenzo[b]pyrazolo[3,4-e][1,4]diazepin-5 (1H)-yl)methanone [W10807F]

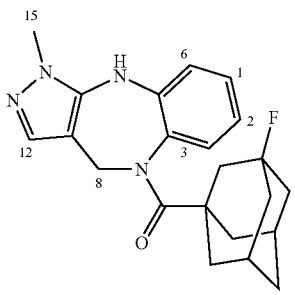 [SMILES: Cn1ncc2c1Nc1ccccc1N(C(=O)C13CC4CC(CC(F)(C4)C1)C3)C2]

Treating diazepine 1 (150 mg, 0.75 mmol) with the acid chloride derived from 3-fluoroadamantane carboxylic acid (149 mg, 0.75 mmol) according to the above general procedure A followed by purification via flash column chromatography (silica, 0.25:2.25:97.5 to 0.5:4.5:95 v/v/v 28% aq. ammonia/MeOH/CH$_2$Cl$_2$ gradient elution) produced WJ0807F (148 mg, 52%) as a white crystalline powder ($R_f$=0.41 in a 1:9:90 v/v/v 28% aq. ammonia/MeOH/CH$_2$Cl$_2$ solution).

$^1$H NMR (500 MHz, DMSO-d$_6$): 8.46 (br s, 1H, NH), 7.40-7.29 (m, 2H, 3/2-2×CH), 7.28-7.21 (m, 1H, 6-CH), 7.06 (s, 1H, 12-CH), 7.02 (ddd, J=7.7, 6.3, 2.4 Hz, 1H, 1-CH), 5.44 (d, J=14.3 Hz, 1H, 8-CH$_2$), 3.70 (s, 3H, 15-CH$_3$), 3.64 (d, J=14.3 Hz, 1H, 8-CH$_2$), 2.05 (d, J=12.3 Hz, 2H), 1.80 (dd, J=11.6, 6.0 Hz, 1H), 1.71 (d, J=12.9 Hz, 1H), 1.61 (d, J=14.1 Hz, 3H), 1.53 (d, J=10.7 Hz, 2H), 1.40 (dd, J=28.7, 12.8 Hz, 4H), 1.23 (d, J=12.6 Hz, 1H). $^{13}$C NMR (126 MHz, DMSO-d$_6$): δ 173.3, 140.5, 139.1, 135.9, 132.7, 130.8, 129.2, 121.5, 120.2, 100.5, 92.4 (d, J=182.2 Hz), 47.2 (d, J=9.7 Hz), 46.4, 44.0 (d, J=19.3 Hz, 2CH$_2$), 41.2 (d, J=17.2 Hz, 2CH$_2$), 37.7, 37.1, 35.2, 34.1, 30.4 (d, J=10.0 Hz). $^{19}$F NMR (471 MHz, DMSO-d$_6$): δ −113.2. IR (diamond cell, neat) $v_{max}$: 3276, 2912, 1613, 1593, 1555, 1450, 1389, 1278, 1249, 1156, 1020, 987, 929, 836, 763, 724, 695, 645, 591, 536, 444 cm$^{-1}$. LRMS (+ESI) m/z: 381 [(M+H)$^+$, 100%], 403 [(M+Na)$^+$, 50%]. HRMS (+ESI) Found: (M+H)$^+$, 381.2086. C$_{22}$H$_{25}$FN$_4$O requires (M+H)$^+$, 381.2085. MP 266-268° C. (decomp). HPLC purity: 95.38%, RT: 20.52 min.

Example 21: ((1r,3R,5S,7r)-3,5-Difluoroadamantan-1-yl)(1-methyl-4,10-dihydrobenzo[b]pyrazolo[3,4-e][1,4]diazepin-5 (1H)-yl)methanone [WJ0807diF]

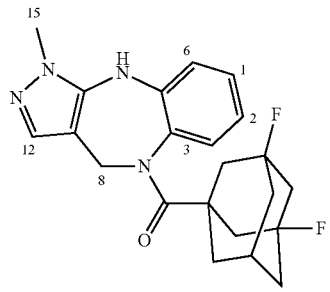 [SMILES: Cn1ncc2c1Nc1ccccc1N(C(=O)C13CC4CC(F)(CC(F)(C4)C1)C3)C2]

Treating diazepine 1 (150 mg, 0.75 mmol) with the acid chloride derived from difluoroadamantane carboxylic acid (162 mg, 0.75 mmol) according to the above general procedure A followed by purification via flash column chromatography (silica, 0.25:2.25:97.5 to 0.5:4.5:95 v/v/v 28% aq. ammonia/MeOH/CH$_2$Cl$_2$ gradient elution) produced WJ0807diF (207 mg, 69%) as white needles ($R_f$=0.39 in a 1:9:90 v/v/v 28% aq. ammonia/MeOH/CH$_2$Cl$_2$ solution).

$^1$H NMR (500 MHz, DMSO-d$_6$): 8.51 (br s, 1H, NH), 7.41-7.31 (m, 2H, 3/2-2×CH), 7.29 (dd, J=7.9, 1.4 Hz, 1H, 6-CH), 7.07 (s, 1H, 12-CH), 7.04 (ddd, J=7.8, 6.6, 2.1 Hz, 1H, 1-CH), 5.45 (d, J=14.3 Hz, 1H, 8-CH$_2$), 3.80-3.59 (m, 4H, 15-CH$_3$/8-CH$_2$), 2.00-1.71 (m, 5H), 1.60 (d, J=25.0 Hz, 4H), 1.48 (s, 3H), 1.33 (d, J=13.1 Hz, 1H). $^{13}$C NMR (126 MHz, DMSO-d$_6$): δ 171.6, 140.6, 139.0, 135.9, 132.2, 130.8, 129.4, 121.7, 121.7, 120.3, 100.3, 93.1 (dd, J=186.1, 13.8 Hz), 47.9 (d, J=10.1 Hz), 46.6 (t, J=9.4 Hz), 42.9 (d, J=17.1 Hz, 2CH$_2$). 42.6-42.2 (m, 2CH$_2$), 36.9, 36.1, 35.3, 29.9 (t, J=10.7 Hz). $^{19}$F NMR (471 MHz, DMSO-d$_6$): −104.46 (dd, J=1790.7, 230.2 Hz, 2F). IR (diamond cell, neat) $v_{max}$: 3301, 2944, 1735, 1611, 1554, 1498, 1444, 1375, 1328, 1308, 1277, 1245, 1175, 1122, 1042, 1018, 987, 951, 867, 831, 804, 755, 723, 693, 639, 544, 460, 417 cm$^{-1}$. LRMS (+ESI) m/z: 399 [(M+H)$^+$, 20%], 421 [(M+Na)$^+$, 100%]. HRMS (+ESI) Found: (M+H)⁺, 399.1991. C₂₂H₂₄F₂N₄O requires (M+H)⁺, 399.1991. MP 262-264° C. (decomp). HPLC purity: 96.14%, RT: 19.24 min.

Example 22: (1-Methyl-4,10-dihydrobenzo[b]pyrazolo[3,4-e][1,4]diazepin-5 (1H)-yl)(pyridin-2-yl)methanone [WJ0759]

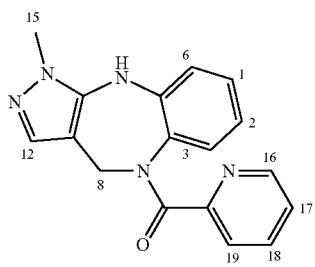

Treating diazepine 1 (100 mg, 0.5 mmol) with the acid chloride derived from picolinic acid (74 mg, 0.6 mmol) according to the above general procedure A followed by purification via trituration (EtOAc) and recrystallisation (MeOH) produced WJ0759 (90 mg. 59%) as a brown crystalline solid (R$_f$=0.58 in a 1:9:90 v/v/v 28% aq. ammonia/MeOH/CH₂Cl₂ solution).

¹H NMR (500 MHz, DMSO-d₆): δ 8.58 (br s, 1H, NH), 8.25 (dt, J=4.8, 1.4 Hz, 1H, 16-CH), 7.67 (td, J=7.7, 1.7 Hz, 1H, 2-CH), 7.33 (dd, J=7.9, 1.1 Hz, 1H, 3-CH), 7.25-7.15 (m, 3H, 12/17/16-3×CH), 7.04 (ddd, J=8.4, 7.3, 1.6 Hz, 1H, 18-CH), 6.69 (dd, J=7.9, 1.6 Hz, 1H, 6-CH), 6.54 (td, J=7.6, 1.4 Hz, 1H, 1-CH), 5.65 (d, J=14.4 Hz, 1H, 8-CH₂), 3.95 (d, J=14.4 Hz, 1H, 8-CH₂), 3.76 (s. 3H, 15-CH₃). ¹³C NMR (126 MHz, DMSO-d₆): δ 166.8, 154.4, 148.2, 139.8, 138.7, 136.3, 135.6, 131.3, 130.1, 127.9, 123.8, 122.4, 120.4, 119.4, 100.0, 42.9, 35.3. IR (diamond cell, neat) ν$_{max}$: 3275, 1620, 1561, 1504, 1441, 1397, 1320, 1244, 1152, 1050, 989, 848, 826, 811, 752, 741, 691, 658, 631, 614, 595, 488, 446 cm⁻¹. LRMS (+ESI) m/z: 328 [(M+Na)⁺, 100%], 633 [(2M+Na)⁺, 60%]. HRMS (+ESI) Found: (M+H)⁺, 306.1351. C₁₇H₁₅N₅O requires (M+H)⁺, 306.1349. MP 269-271° C. (decomp). HPLC purity: 96.78%, RT: 15.07 min.

Example 23: (1-Methyl-4,10-dihydrobenzo[b]pyrazolo[3,4-e][1,4]diazepin-5 (1H)-yl)(pyridin-3-yl)methanone [WJ07531]

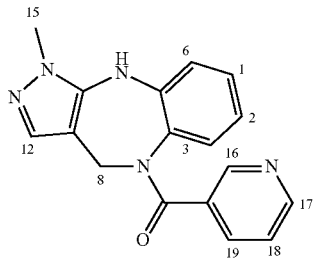

Treating diazepine 1 (200 mg, 1 mmol) with the acid chloride derived from nicotinic acid (148 mg, 1.2 mmol) according to the above general procedure A followed by purification via trituration (EtOAc) and recrystallisation (MeOH) produced WJ0753 (140 mg, 46%) as a white powder (R$_f$=0.60 in a 1:9:90 v/v/v 28% aq. ammonia/MeOH/CH₂Cl₂ solution).

¹H NMR (500 MHz, DMSO-d₆): δ 8.65 (br s, 1H, NH), 8.40 (dd, J=4.9, 1.7 Hz, 1H, 17-CH), 8.27 (dd, J=2.3, 0.9 Hz, 1H, 6-CH), 7.54 (dt, J=7.9, 1.9 Hz, 1H, 19-CH), 7.29 (dd, J=8.2, 1.4 Hz, 1H, 3-CH), 7.23 (ddd, J=7.9, 4.9, 0.9 Hz, 1H, 18-CH), 7.19 (s, 1H, 12-CH), 7.13 (ddd, J=8.3, 7.2, 1.6 Hz, 1H, 2-CH), 6.82 (dd, J=7.9, 1.6 Hz, 1H, 6-CH), 6.71-6.56 (m, 1H, 1-CH), 5.67 (d, J=14.5 Hz, 1H, 8-CH₂), 3.97 (d, J=14.4 Hz, 1H, 8-CH₂), 3.78 (s, 3H, 15-CH). ¹³C NMR (126 MHz, DMSO-d₆): δ 166.2, 150.0, 147.6, 139.7, 139.2, 135.6, 134.8, 132.3, 131.6, 130.6, 128.6, 122.9, 121.2, 119.6, 100.1, 43.2, 35.4. IR (diamond cell, neat) ν$_{max}$: 3315, 1623, 1563, 1503, 1449, 1408, 1300, 1246, 1148, 1024, 993, 946, 827, 756, 742, 707, 691, 630, 557, 494, 448 cm⁻¹. LRMS (+ESI) m/z: 301 [(M+H)⁺, 60%], 328 [(M+Na)⁺, 100%]. HRMS (+ESI) Found: (M+H)⁺, 306.1350. C₁₇H₁₅N₅O requires (M+H)⁺, 306.1349. MP 247-249° C. (decomp). HPLC purity: 98.10%, RT: 14.09 min.

Example 24: (1-Methyl-4,10-dihydrobenzo[b]pyrazolo[3,4-e][1,4]diazepin-5 (1H)-yl)(pyridin-4-yl)methanone [WJ0757]

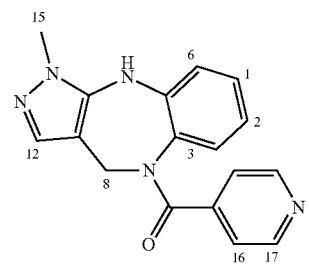

Treating diazepine 1 (100 mg, 0.5 mmol) with the acid chloride derived from isonicotinic acid (74 mg, 0.6 mmol) according to the above general procedure A followed by purification via trituration (EtOAc) and recrystallisation (MeOH) produced WJ0757 (80 mg, 52%) as a yellow crystalline solid (R$_f$=0.51 in a 1:9:90 v/v/v 28% aq. ammonia/MeOH/CH₂Cl₂ solution).

¹H NMR (500 MHz, DMSO-d₆): δ 8.65 (br s, 1H, NH), 8.46-8.33 (m, 2H, 17-2×CH), 7.27 (dd, J=8.2, 1.4 Hz, 1H, 3-CH), 7.20 (s, 1H, 12-CH), 7.12 (ddd, J=8.4, 7.4, 1.6 Hz, 1H, 2-CH), 7.10-7.06 (m, 2H, 16-2×CH), 6.83 (dd, J=7.9, 1.5 Hz, 1H, 6-CH), 6.64 (td, J=7.6, 1.4 Hz, 1H, 6-CH), 5.63 (d, J=14.5 Hz, 1H, 8-CH₂), 3.97 (d, J=14.4 Hz, 1H, 8-CH₂), 3.78 (s, 3H, 15-CH₃). ¹³C NMR (126 MHz, DMSO-d₆): δ 166.4, 149.3, 144.0, 139.6, 139.1, 135.7, 131.0, 130.5, 128.8, 121.1, 121.1, 119.5, 100.0, 43.1, 35.4. IR (diamond cell, neat) ν$_{max}$: 3328, 1626, 1561, 1503, 1450, 1408, 1299, 1244, 1146, 989, 948, 826, 758, 741, 685, 648, 633, 602, 544, 494, 449 cm⁻¹. LRMS (+ESI) m/z: 328 [(M+Na)⁺, 100%], 633 [(2M+Na)⁺, 60%]. HRMS (+ESI) Found: (M+H)⁺, 306.1350. C₁₇H₁₅N₅O requires (M+H)⁺, 306.1349. MP 267-269° C. (decomp). HPLC purity: 99.00%, RT: 13.40 min.

Example 25: (2-Bromophenyl)(1-methyl-4,10-dihydrobenzo[b]pyrazolo[3,4-e][1,4]diazepin-5 (1H)-yl)methanone [WJ0822]

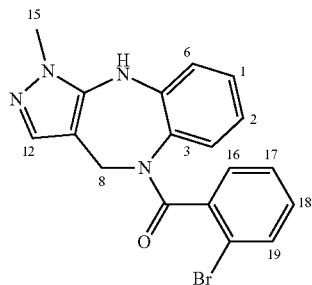 [SMILES: Cn1ncc2c1Nc1ccccc1N(C(=O)c1ccccc1Br)C2]

Treating diazepine 1 (90 mg, 0.45 mmol) with the acid chloride derived from 2-bromobenzoic acid (90 mg, 0.45 mmol) according to the above general procedure A followed by purification via trituration (EtOAc) and recrystallisation (MeOH) produced WJ0822 (97 mg, 56%) as a white crystalline solid ($R_f$=0.59 in EtOAc).

$^1$H NMR (400 MHz, DMSO-$d_6$): δ 8.59 (br s, 1H, NH), 7.50-7.44 (m, 2H, 16/17-CH), 7.23-7.17 (m, 2H, 12/3-2×CH), 7.18-7.10 (m, 2H, 18/19-2×CH), 7.05 (ddd, J=8.4, 7.3, 1.6 Hz, 1H, 2-CH), 6.94 (dd, J=7.9, 1.5 Hz, 1H, 6-CH), 6.65-6.57 (m, 1H, 1-CH), 5.57 (d, J=14.4 Hz, 1H, 8-CH$_2$), 3.98 (d, J=14.4 Hz, 1H, 8-CH$_2$), 3.76 (s, 3H, 15-CH$_3$). $^{13}$C NMR (101 MHz, DMSO-$d_6$): δ 166.6, 140.0, 139.6, 138.9, 138.3, 135.7, 132.3, 130.1, 128.6, 127.8, 126.9, 120.7, 120.1, 119.5, 119.1, 100.2, 42.9, 35.4. IR (diamond cell, neat) $v_{max}$: 3307, 1625, 1557, 1502, 1390, 1302, 1145, 1049, 1028, 982, 826, 784, 756, 739, 689, 633, 597, 492, 445 cm$^{-1}$. LRMS (−ESI) m/z: 381/383 [(M−H)$^-$, 90/100%]. HRMS (+ESI) Found: (M+H)$^+$, 383.0502/385.0481. C$_{18}$H$_{15}$BrN$_4$O requires (M+H)$^+$, 383.0502/385.0482. MP 244-246° C. HPLC purity: 97.02%, RT: 19.23 min.

Example 26: (3-Bromophenyl)(1-methyl-4,10-dihydrobenzo[b]pyrazolo[3,4-e][1,4]diazepin-5 (1H)-yl)methanone [WJ0821]

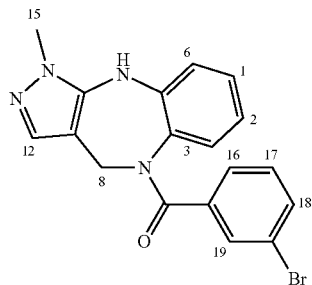 [SMILES: Cn1ncc2c1Nc1ccccc1N(C(=O)c1cccc(Br)c1)C2]

Treating diazepine 1 (90 mg, 0.45 mmol) with the acid chloride derived from 3-bromobenzoic acid (90 mg, 0.45 mmol) according to the above general procedure A followed by purification via trituration (EtOAc) and recrystallisation (MeOH) produced WJ0821 (100 mg, 58%) as a white powder ($R_f$=0.64 in EtOAc).

$^1$H NMR (400 MHz, DMSO-$d_6$): δ 8.66 (br s, 1H, NH), 7.43 (dt, J=6.7, 2.3 Hz, 1H, 16-CH), 7.36-7.25 (m, 2H, 18/19-2×CH), 7.18 (s, 1H, 12-CH), 7.17-7.06 (m, 3H, 2/3/17-3×CH), 6.79 (dd, J=7.9, 1.6 Hz, 1H, 6-CH), 6.70-6.63 (m, 1H, 1-CH), 5.65 (d, J=14.6 Hz, 1H, 8-CH$_2$), 3.94 (d, J=14.5 Hz, 1H, 8-CH$_2$), 3.77 (s, 3H, 15-CH$_3$). $^{13}$C NMR (101 MHz, DMSO-$d_6$): δ 166.6, 139.7, 139.0, 138.6, 135.7, 132.2, 131.7, 130.4, 129.9, 129.9, 128.5, 126.1, 121.3, 120.9, 119.5, 100.1, 43.2, 35.4. IR (diamond cell, neat) $v_{max}$: 3317, 1623, 1562, 1504, 1450, 1403, 1297, 1247, 1144, 990, 829, 796, 761, 716, 696, 631, 555, 496, 448 cm$^{-1}$. LRMS (−ESI) m/z: 381/383 [(M−H)$^-$, 98/100%]. HRMS (+ESI) Found: (M+H)$^+$, 383.0502/385.0482. C$_{18}$H$_{15}$BrN$_4$O requires (M+H)$^+$, 383.0502/385.0482. MP 218-220° C. HPLC purity: 96.58%, RT: 21.25 min.

Example 27: (4-Bromophenyl)(1-methyl-4,10-dihydrobenzo[b]pyrazolo[3,4-e][1,4]diazepin-5 (1H)-yl)methanone [WJ0820]

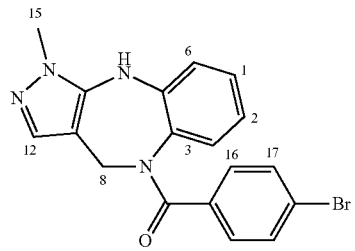 [SMILES: Cn1ncc2c1Nc1ccccc1N(C(=O)c1ccc(Br)cc1)C2]

Treating diazepine 1 (90 mg, 0.45 mmol) with the acid chloride derived from 4-bromobenzoic acid (90 mg, 0.45 mmol) according to the above general procedure A followed by purification via trituration (EtOAc) and recrystallisation (MeOH) produced WJ0820 (119 mg, 69%) as a white powder ($R_f$=0.75 in EtOAc).

$^1$H NMR (400 MHz, DMSO-$d_6$): δ 8.62 (s, 1H, NH), 7.42-7.33 (m, 2H, 16-2×CH), 7.28 (dd, J=8.1, 1.4 Hz, 1H, 3-CH), 7.18 (s, 1H, 12-CH), 7.16-7.10 (m, 1H, 2-CH), 7.10-7.02 (m, 2H, 17-2×CH), 6.75 (dd, J=7.8, 1.6 Hz, 1H, 6-CH), 6.65 (td, J=7.5, 1.4 Hz, 1H, 1-CH), 5.66 (d, J=14.5 Hz, 1H, 8-CH$_2$), 3.92 (d, J=14.5 Hz, 1H, 8-CH$_2$), 3.77 (s, 3H, 15-CH$_3$). $^{13}$C NMR (101 MHz, DMSO-$d_6$): δ 167.3, 139.7, 138.9, 135.6, 135.6, 131.8, 130.7, 130.4, 129.3, 128.4, 122.8, 121.2, 119.6, 100.2, 43.2, 35.4. IR (diamond cell, neat) $v_{max}$: 3322, 1624, 1558, 1504, 1453, 1403, 1297, 1246, 1136, 1069, 1012, 989, 828, 763, 750, 695, 629, 594, 548, 495, 449, 423 cm$^{-1}$. LRMS (−ESI) m/z: 381/383 [(M−H)$^-$, 94/100%]. HRMS (+ESI) Found: (M+H)$^+$, 383.0505/385.0482. C$_{18}$H$_{15}$BrN$_4$O requires (M+H)$^+$, 383.0502/385.0482. MP 249-251° C. HPLC purity: 96.11%, RT: 20.26 min.

Example 28: 1-Methyl-5-((4-methyl-2-nitrophenyl)amino)-1H-pyrazole-4-carbaldehyde (3)

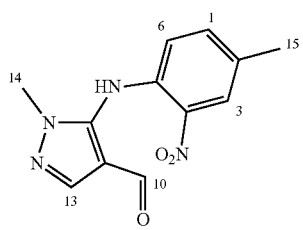

A magnetically stirred solution of 5-chloro-1-methyl-1H-pyrazole-4-carbaldehyde (250 mg, 1.7 mmol) and 2-nitro-4-methylaniline (789 g, 5.2 mmol) in DMF (20 mL) was treated with powdered KOH (194 mg, 3.5 mmol) then heated at 100° C. for 18 h. The resulting mixture was cooled and diluted with NH$_4$Cl (250 mL of a sat. aq. solution) and extracted with EtOAc (3×100 mL). The combined organic phases were washed with brine (100 mL) before being dried (MgSO$_4$), filtered and concentrated under reduced pressure to afford an orange crystalline solid. Subjection of this residue to medium pressure liquid chromatography (MPLC) using a Teledyne ISCO CombiFlash® Rf+ system (silica, 80% hexanes/EtOAc 40 min followed by 50% hexanes/EtOAc gradient elution) and concentration of the relevant fractions ($R_f$=0.41 in a 1:1 v/v EtOAc/hexanes solution) afforded 1-Methyl-5-((4-methyl-2-nitrophenyl)amino)-1H-pyrazole-4-carbaldehyde (290 mg, 66%) as an orange crystalline solid. The spectral data for this compound, is identical in all aspects with those previously reported.

$^1$H NMR (300 MHz, Chloroform-d): δ 9.62 (s, 1H, 10-CH), 9.18 (s, 1H, NH). 7.98 (d, J=1.4 Hz, 1H, 3-CH), 7.91 (s, 1H, 13-CH) 7.22 (dd, J=8.6, 1.3 Hz, 1H, 1-CH), 6.47 (d, J=8.6 Hz, 1H, 6-CH), 3.65 (s, 3H, 14-CH$_3$), 2.28 (s. 3H, 15-CH$_3$). $^{13}$C NMR (75 MHz, Chloroform-d): δ 193.3, 141.0, 140.6, 138.0, 137.2, 134.7, 130.4, 126.2, 116.4, 116.0, 35.8, 20.2.

Example 29: 1,7-Dimethyl-1,4,5,10-tetrahydrobenzo[b]pyrazolo[3,4-e][1,4]diazepine (4)

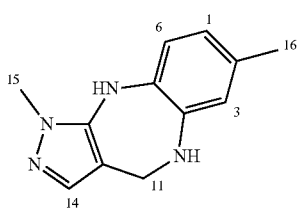

A suspension of 1-Methyl-5-((4-methyl-2-nitrophenyl)amino)-1H-pyrazole-4-carbaldehyde (260 mg, 1.0 mmol) and Pd/C (20 mg of 10% w/w) in MeOH (100 mL) was stirred magnetically at room temperature under an atmosphere of hydrogen (1 atm) for 16 h. The resulting mixture was filtered through Celite® and the solids thus retained were washed with methanol (3×20 mL). The combined filtrates were concentrated under reduced pressure and recrystallisation from CH$_2$Cl$_2$/MeOH afforded, 7-Dimethyl-1,4,5,10-tetrahydrobenzo[b]pyrazolo[3,4-e][1,4]diazepine (200 mg, 93%) as yellow needles that were used immediately in the subsequent step.

Example 30: (1,7-Dimethyl-4,10-dihydrobenzo[b]pyrazolo[3,4-e][1,4]diazepin-5 (1H)-yl)(phenyl)methanone [WJ07117Me]

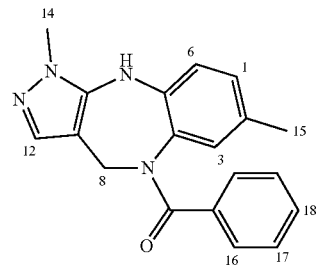

Treating 1,7-Dimethyl-1,4,5,10-tetrahydrobenzo[b]pyrazolo[3,4-e][1,4]diazepine (200 mg, 0.93 mmol) with benzoyl chloride (174 μL, 1.5 mmol) according to the above general procedure A followed by purification via flash column chromatography (silica, 0.25:2.25:97.5 to 0.5:4.5:95 v/v/v 28% aq. ammonia/MeOH/CH$_2$Cl$_2$ gradient elution) produced WJ07117Me (177 mg, 60%) as an off-white powder ($R_f$=0.21 in a 1:9:90 v/v/v 28% aq. ammonia/MeOH/CH$_2$Cl$_2$ solution).

$^1$H NMR (500 MHz, DMSO-d$_6$): 8.48 (s, 1H, NH), 7.32-7.20 (m, 1H, 6-CH), 7.20-7.10 (m, 6H, 16/17/18/12-6×CH), 6.97-6.86 (m, 1H, 1-CH), 6.54 (d, J=1.7 Hz, 1H, 3-CH), 5.66 (d, J=14.5 Hz, 1H, 8-CH$_2$), 3.89 (d, J=14.5 Hz, 1H, 8-CH$_2$), 3.75 (s, 3H, 14-CH$_3$), 1.94 (s, 3H, 15-CH$_3$). $^{13}$C NMR (126 MHz, DMSO-d$_6$): δ 168.2, 140.0, 136.5, 135.6, 132.2, 130.5, 130.1, 129.3, 128.7, 127.7, 127.6, 127.2, 119.4, 99.9, 43.1, 35.3, 19.6. IR (diamond cell, neat) $v_{max}$: 3267, 1613, 1553, 1510, 1401, 1314, 1247, 1138, 986, 823, 796, 759, 724, 703, 652, 569, 488, 462, 432 cm$^{-1}$. LRMS (+ESI) m/z: 341 [(M+Na)$^+$, 100%]. HRMS (+ESI) Found: (M+H)$^+$, 319.1554. C$_{19}$H$_{18}$N$_4$O requires (M+H)$^+$, 319.1553. MP 235-238° C. HPLC purity: 96.44%, RT: 18.85 min.

Example 31: 5-((4-Methoxy-2-nitrophenyl)amino)-1-methyl-1H-pyrazole-4-carbaldehyde

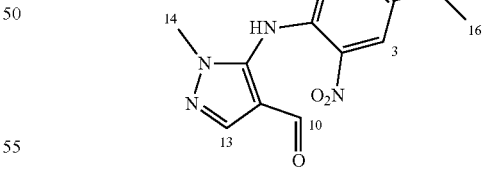

A magnetically stirred solution of 5-chloro-1-methyl-1H-pyrazole-4-carbaldehyde (250 mg, 1.7 mmol) and 2-nitro-4-methoxyaniline (872 g, 5.2 mmol) in DMF (20 mL) was treated with powdered KOH (194 mg, 3.5 mmol) then heated at 100° C. for 18 h. The resulting mixture was cooled and diluted with NH$_4$Cl (250 mL of a sat. aq. solution) and extracted with EtOAc (3×100 mL). The combined organic phases were washed with brine (100 mL) before being dried (MgSO$_4$), filtered and concentrated under reduced pressure to afford an orange crystalline solid. Subjection of this residue to medium pressure liquid chromatography (MPLC) using a Teledyne ISCO CombiFlash® Rf+ system (silica, 80% hexanes/EtOAc 40 min followed by 50% hexanes/EtOAc gradient elution) and concentration of the relevant fractions ($R_f$=0.22 in a 1:1 v/v EtOAc/hexanes solution) afforded the title pyrazole (5) (274 mg, 58%) as a brown crystalline solid. The spectral data for this compound, is identical in all aspects with those previously reported.

$^1$H NMR (300 MHz, Chloroform-d): δ 9.72 (s, 1H, 10-CH), 9.13 (s, 1H, NH). 7.94 (s, 1H, 13-CH), 7.66 (d, J=2.4 Hz, 1H, 3-CH) 7.11 (dd, J=9.2, 2.3 Hz, 1H, 1-CH), 6.57 (d, J=9.2 Hz, 1H, 6-CH), 3.82 (s, 3H, 14-CH$_3$), 3.68 (s, 3H, 15-CH$_3$). $^{13}$C NMR (75 MHz, Chloroform-d): δ 193.3, 153.0, 141.0, 140.9, 135.2, 134.2, 125.1, 118.2, 115.4, 108.0, 55.8, 35.9.

Example 32: 7-Methoxy-1-methyl-1,4,5,10-tetrahydrobenzo[b]pyrazolo[3,4-e][1,4]diazepine

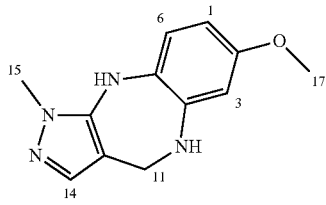

A suspension of 5-((4-Methoxy-2-nitrophenyl)amino)-1-methyl-1H-pyrazole-4-carbaldehyde (276 mg, 1.0 mmol) and Pd/C (30 mg of 10% w/w) in MeOH (100 mL) was stirred magnetically at room temperature under an atmosphere of hydrogen (1 atm) for 16 h. The resulting mixture was filtered through Celite® and the solids thus retained were washed with methanol (3×20 mL). The combined filtrates were concentrated under reduced pressure and recrystallisation from CH$_2$Cl$_2$/MeOH afforded 7-Methoxy-1-methyl-1,4,5,10-tetrahydrobenzo[b]pyrazolo[3,4-e][1,4] diazepine as a pink crystalline solid (200 mg, 87%) that was used immediately in the subsequent step.

Example 33: (7-Methoxy-1-methyl-4,10-dihydrobenzo[b]pyrazolo[3,4-e][1,4]diazepin-5 (1H)-yl)(phenyl)methanone [WJ07117MeO]

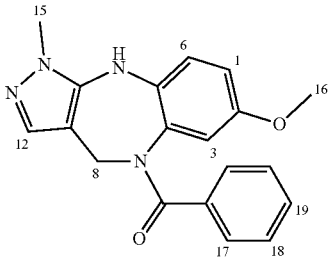

Treating 7-Methoxy-1-methyl-1,4,5,10-tetrahydrobenzo [b]pyrazolo[3,4-e][1,4]diazepine (200 mg, 0.87 mmol) with benzoyl chloride (174 µL. 1.5 mmol) according to the above general procedure A followed by purification via flash column chromatography (silica. 0.25:2.25:97.5 to 0.5:4.5:95 v/v/v 28% aq. ammonia/MeOH/CH$_2$Cl$_2$ gradient elution) produced WJ07117MeO (221 mg, 76%).

$^1$H NMR (400 MHz, DMSO-d$_6$): 8.37 (br s, 1H, NH), 7.28-7.24 (m, 1H, 6-CH), off-white powder (R; =0.24 in a 1:9:90 v/v/v 28% aq. ammonia/MeOH/CH$_2$Cl$_2$ solution). 7.20-7.17 (m, 5H, 17/18/19-5×CH), 7.16 (s, 1H, 12-CH), 6.72 (dd, J=8.9, 2.9 Hz, 11-, 1-CH), 6.37 (d, J=2.9 Hz, 1H, 3-CH), 5.67 (d, J=14.5 Hz, 1H, 8-CH$_2$), 3.92 (d, J=14.5 Hz, 1H, 8-CH$_2$), 3.75 (s, 3H, 15-CH$_3$), 3.43 (s, 3H, 16-CH$_3$). $^{13}$C NMR (101 MHz, DMSO-d$_6$): δ 168.3, 153.6, 140.2, 136.5, 135.6, 133.3, 132.5, 129.4, 127.6, 127.1, 120.5, 115.1, 114.6, 99.5, 55.2, 42.9, 35.2. IR (diamond cell, neat) vax: 3329, 1614, 1566, 1509, 1450, 1402, 1289, 1208, 1173, 1139, 1030, 986, 835, 810, 759, 726, 696, 652, 566, 475 cm 1. LRMS (+ESI) m/z: 357 [(M+Na)$^+$, 100%]. HRMS (+ESI) Found: (M+H)$^+$, 335.1504. C$_{19}$H$_{18}$N$_4$O$_2$ requires (M+H)$^+$, 335.1503. MP 248-250° C. HPLC purity: 98.29%, RT: 17.69 min.

Example 34: (4-(benzyloxy)phenyl)(1-methyl-4,10-dihydrobenzo[b]pyrazolo[3,4-e][1,4]diazepin-5 (1H)-yl)methanone (BzE)

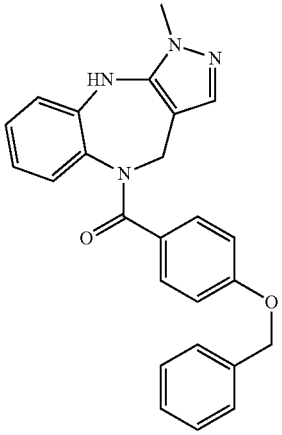 [SMILES: Cn1ncc2c1Nc1ccccc1N(C(=O)c1ccc(OCc3ccccc3)cc1)C2]

Treating diazepine 1 (1.9 g, 9.5 mmol) with the acid chloride derived from cyclohexanecarboxylic acid (2.6 g, 11.4 mmol) according to the above general procedure A followed by purification via flash column chromatography (silica, 1:99 to 1:9 v/MeOH/CH$_2$Cl$_2$ gradient elution) produced TAR-B041 (3.5 g, 90%) as a white powder ($R_f$=0.72 in EtOAc).

$^1$H NMR (300 MHz, DMSO-d$_6$): δ 8.57 (s, 1H), 7.47-7.24 (m, 6H), 7.20-6.98 (m, 4H), 6.78 (d, J=8.3 Hz, 2H), 6.68 (d, J=9.4 Hz, 2H), 5.68 (d, J=14.6 Hz, 1H), 5.02 (s, 2H), 3.88 (d, J=14.6 Hz, 1H), 3.76 (s. 3H). $^{13}$C NMR (75 MHz, DMSO-d$_6$): δ 167.63, 159.10, 139.83, 138.70, 136.55, 135.52, 132.69, 130.29, 129.44, 128.45, 128.34, 128.05, 127.87, 127.80, 121.23, 119.57, 113.70, 100.41, 69.21, 43.15, 35.28. IR (diamond cell, neat) v$_{max}$: 3323, 2939, 2878, 1620, 1561, 1504, 1451, 1397, 1297, 1225, 1170, 1038, 832, 764, 728, 695, 629 cm$^{-1}$. LRMS (+ESI) m/z: 433 [(M+Na)$^+$, 100%], m/z: 411 [(M+H)$^+$, 20%]. MP: 207-209° C. HPLC purity: 99.24%, RT: 22.82 min.

Example 35: (4-hydroxyphenyl)(1-methyl-4,10-dihydrobenzo[b]pyrazolo[3,4-e][1,4]diazepin-5 (1H)-yl)methanone (TAR-B049)

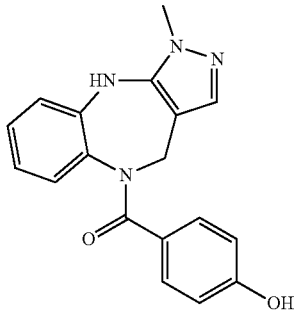 [SMILES: Cn1ncc2c1Nc1ccccc1N(C(=O)c1ccc(O)cc1)C2]

A magnetically stirred suspension of the product from TAR-B048 (1.0 g, 2.44 mmol) and Pd/C (270 mg of a 10% w/w) in MeOH/THF (100 mL of 1:1 v/v) was placed under an atmosphere of hydrogen (1 atm) for 16 h. The resulting mixture was filtered through Celite® and the solids thus retained were washed with MeOH (3×50 mL). The combined filtrates were concentrated under reduced pressure and purified by flash column chromatography (silica, 9:1 v/v CH$_2$Cl$_2$/MeOH) and concentration of the relevant fractions (R$_f$=0.42 EtOAc) produced TAR-B049 (773 mg, 99%) as a white powder.

$^1$H NMR (300 MHz, DMSO-d$_6$): δ 9.85 (s, 1H), 8.59 (s, 1H), 7.30 (d, J=8.2 Hz, 1H), 7.12 (d, J=6.4 Hz, 2H), 6.99 (d, J=8.2 Hz, 2H), 6.66 (d, J=4.6 Hz, 2H), 6.51 (d, J=8.2 Hz, 2H), 5.66 (d, J=14.8 Hz, 1H), 3.86 (d, J=14.9 Hz, 1H), 3.76 (s, 3H). $^{13}$C NMR (75 MHz, DMSO-d$_6$): δ 168.03, 158.65, 139.93, 138.69, 135.53, 132.97, 130.30, 129.63, 127.91, 126.46, 121.19, 119.58, 114.29, 100.51, 35.34, 25.48. IR (diamond cell, neat) ν$_{max}$: 3305, 2953, 1621, 1563, 1503, 1449, 1395, 1243, 1142, 1005, 825, 754, 731 cm$^{-1}$. LRMS (+ESI) m/z: 343 [(M+Na)$^+$, 100%], m/z: 321 [(M+H)$^+$, 27%]. MP: >300° C.

Example 36: cyclohexyl(1-methyl-4,10-dihydrobenzo[b]pyrazolo[3,4-e][1,4]diazepin-5 (1H)-yl)methanone (CA6)

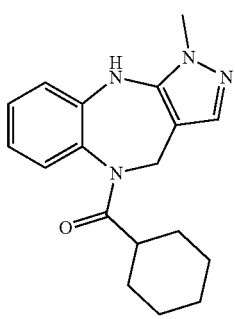 [SMILES: Cn1ncc2c1Nc1ccccc1N(C(=O)C1CCCCC1)C2]

Treating diazepine 1 dihydrochloride (150 mg, 0.75 mmol) with the acid chloride derived from cyclohexanecarboxylic acid (115 mg, 0.61 mmol) according to the above general procedure C followed by purification via flash column chromatography (silica. 1:99 to 1:9 v/MeOH/ CH$_2$Cl$_2$ gradient elution) produced TAR-B041 (214 mg, 92%) as a white powder (R$_f$=0.30 in 1:9 v/v MeOH/ CH$_2$Cl$_2$).

$^1$H NMR (300 MHz, DMSO-d$_6$): δ 8.37 (s, 1H), 7.38-7.28 (m, 2H), 7.21 (d, J=7.9 Hz, 1H), 7.07 (s, 1H), 7.00 (ddd, J=8.2, 5.7, 2.9 Hz, 1H), 5.39 (d, J=14.4 Hz, 1H), 3.73 (s, 1H), 3.68 (s, 4H), 2.18-2.03 (m, 1H), 1.66 (t, J=16.1 Hz, 2H), 1.58-1.43 (m, 1H), 1.41-1.22 (m, 2H), 1.16-0.85 (m, 3H), 0.73 (q, J=12.8 Hz, 1H). $^{13}$C NMR (75 MHz, DMSO-d$_6$): δ 173.88, 139.72, 139.25, 135.62, 131.55, 129.81, 128.68, 121.57, 120.13, 100.44, 54.82, 42.60, 40.45, 35.13, 29.05, 28.65, 25.20, 24.92. IR (diamond cell, neat) ν$_{max}$: 3297, 1650, 1555, 1501, 1409, 1355, 1287, 1245, 1170, 1118, 989, 832, 762, 696 cm$^{-1}$. LRMS (+ESI) m/z: 369 [(M+Na)$^+$, 100%]. MP: 238-240° C. HPLC purity: 95.78%. RT: 20.47 min.

Example 37: cyclopentyl(1-methyl-4,10-dihydrobenzo[b]pyrazolo[3,4-e][1,4]diazepin-5 (1H)-yl) methanone (CA5)

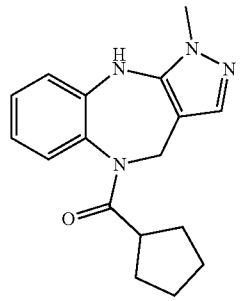

Treating diazepine 1 dihydrochloride (140 mg, 0.51 mmol) with the acid chloride derived from cyclopentanecarboxylic acid (70 mg, 0.61 mmol) according to the above general procedure C followed by purification via flash column chromatography (silica. 1:99 to 1:9 v/MeOH/ CH$_2$Cl$_2$ gradient elution) produced TAR-B091 (139 mg, 92%) as a white powder (R$_f$=0.30 in 1:9 v/v MeOH/1 C$_{12}$Cl$_2$).

$^1$H NMR (300 MHz, Chloroform-d): δ 7.37-7.30 (m, 1H), 7.25 (d, J=6.3 Hz, 2H), 7.10 (t, J=7.5 Hz, 2H), 6.34 (s, 1H), 5.72 (d, J=14.5 Hz, 1H), 3.90 (d, J=14.5 Hz, 1H), 3.79 (s, 3H), 2.65 (p, J=7.9 Hz, 1H), 2.07-1.89 (m, 2H), 1.86-1.54 (m, 4H), 1.52-1.23 (m, 2H). $^{13}$C NMR (75 MHz, Chloroform-d): δ 176.09, 139.44, 139.07, 136.56, 132.35, 130.60, 129.05, 122.66, 119.81, 101.76, 43.24, 42.06, 34.85, 30.80, 26.37, 26.32. JR (diamond cell, neat) ν$_{max}$: 3279, 2939, 2865, 1627, 1557, 1503, 1395, 1300, 1249, 1173, 988, 830, 757, 641 cm$^{-1}$. LRMS (+ESI) m/z: 319 [(M+Na)$^+$, 100%], m/z: 297 [(M+H)$^+$, 8%]. MP: >300° C. HPLC purity: 99.11%, RT: 18.69 min.

Example 38: cyclopropyl(1-methyl-4,10-dihydrobenzo[b]pyrazolo[3,4-e][1,4]diazepin-5 (1H)-yl)methanone (CA3)

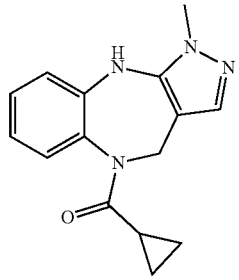 [SMILES: Cn1ncc2c1Nc1ccccc1N(C(=O)C1CC1)C2]

Treating diazepine 1 dihydrochloride (286 mg, 1.05 mmol) with the acid chloride derived from cyclopropanecarboxylic acid (108 mg, 1.25 mmol) according to the above general procedure C followed by purification via flash column chromatography (silica, 1:99 to 1:9 v/MeOH/CH$_2$Cl$_2$ gradient elution) produced TAR-B093 (239 mg, 85%) as a white powder (R$_f$=0.30 in 1:9 v/v MeOH/CH$_2$Cl$_2$).

$^1$H NMR (300 MHz, Chloroform-d): 7.34-7.22 (m, 2H), 7.19 (s, 1H), 7.10-6.91 (m. 2H), 5.97 (s, 1H), 5.69 (d, J=14.6 Hz, 1H), 3.86 (d, J=14.6 Hz, 1H), 3.73 (s. 3H), 1.32 (ddd, 0.1=9.3, 6.3, 4.0 Hz, 1H), 1.13-0.89 (m, 2H), 0.72-0.62 (m, 1H), 0.61-0.45 (m, 1H). $^{13}$C NMR (75 MHz, Chloroform-d): δ 172.95, 139.21, 139.01, 136.41, 131.95, 130.95, 128.96, 122.47, 119.82, 101.72, 43.09, 34.82, 12.50, 8.92, 8.53 cm$^{-1}$. LRMS (+ESI) m/z: 291 [(M+Na)$^+$, 100%]. MP: 207-209° C. HPLC purity: 95.25%. RT: 16.47 min.

Example 39: (1-methyl-4,10-dihydrobenzo[b]pyrazolo[3,4-e][1,4]diazepin-5 (1H)-yl)(4-methylcyclohexyl)methanone (TAR-C41)

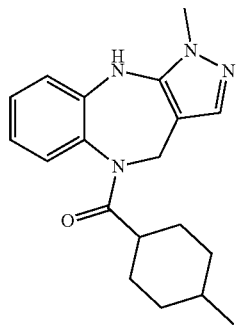 [SMILES: CC1CCC(C(=O)N2Cc3cnn(C)c3Nc3ccccc32)CC1]

Treating diazepine 1 dihydrochloride (240 mg, 0.88 mmol) with the acid chloride derived from 4-methylcyclohexane-1-carboxylic acid (125 mg, 0.88 mmol) according to the above general procedure C followed by purification via flash column chromatography (silica, 1:99 to 1:9 v/MeOH/CH$_2$Cl$_2$ gradient elution) produced TAR-C041 (263 mg, 92%) as a white powder (R$_f$=0.30 in 1:9 v/v MeOH/CH$_2$Cl$_2$).

$^1$H NMR (300 MHz, Chloroform-d): δ 7.29 (d, J=6.0 Hz, 2H), 7.19 (d, J=7.6 Hz, 1H), 7.14-7.03 (m, 2H), 6.34 (s, 1H), 5.65 (d, J=14.6 Hz, 1H), 3.84 (d, J=14.6 Hz, 1H), 3.79 (s, 3H), 2.37-2.23 (m, 1H). 1.96-1.76 (m, 1H), 1.66 (m, 1H), 1.62-1.43 (m, 3H), 1.42-1.26 (m, 2H), 1.19 (ddd, J=14.0, 9.3, 4.9 Hz, 2H), 0.92 (d, J=7.0 Hz, 3H). $^{13}$C NMR (75 MHz, Chloroform-d): δ 175.86, 139.30, 139.26, 136.42, 132.16, 130.14, 129.05, 122.57, 120.06, 101.79, 43.10, 40.16, 34.89, 30.96, 30.73, 27.87, 24.74, 24.51, 18.60. IR (diamond cell, neat) ν$_{max}$: 3280, 2922, 1634, 1556, 1500, 1449, 1406, 1306, 1246, 1173, 988, 838, 759, 692 cm$^{-1}$. LRMS (+ESI) m/z: 347 [(M+Na)$^+$, 100%]. MP: 234-239° C. HPLC purity: 97.42%, RT: 21.87 min.

Example 40: (4-(hexyloxy)phenyl)(1-methyl-4,10-dihydrobenzo[b]pyrazolo[3,4-e][1,4]diazepin-5 (1H)-yl)methanone (TAR-B085)

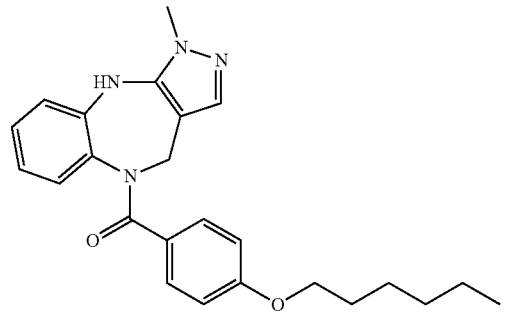 [SMILES: CCCCCCOc1ccc(C(=O)N2Cc3cnn(C)c3Nc3ccccc32)cc1]

Treating diazepine 1 dihydrochloride (132 mg, 0.49 mmol) with the acid chloride derived from 4-(hexyloxy)benzoic acid (108 mg, 0.49 mmol) according to the above general procedure C followed by purification via flash column chromatography (silica, 1:99 to 1:9 v/MeOH/CH$_2$Cl$_2$ gradient elution) produced TAR-B085 (168 mg, 85%) as a white powder (R$_f$=0.30 in 1:9 v/v MeOH/CH$_2$Cl$_2$).

$^1$H NMR (300 MHz, DMSO-d$_6$): δ 8.57 (s, 1H), 7.29 (d, J=8.1 Hz, 1H), 7.11 (dd. J=15.2, 8.3 Hz, 4H), 6.68 (d, J=7.5 Hz, 4H), 5.76-5.58 (m, 1H), 3.98-3.82 (m, 3H), 3.76 (s, 3H), 1.62 (q, J=6.8 Hz, 2H), 1.45-1.21 (m, 6H), 0.96-0.73 (m, 3H). $^{13}$C NMR (75 MHz, DMSO-d$_6$): δ 167.71, 159.46, 139.85, 138.68, 135.54, 132.71, 130.31, 129.47, 128.04, 121.20, 119.56, 113.33, 100.45, 73.51, 67.42, 43.14, 35.31, 30.94, 28.50, 25.09, 22.01, 13.87. IR (diamond cell, neat) ν$_{max}$ 3275, 2937, 2856, 1609, 1557, 1502, 1450, 1395, 1299, 1252, 1173, 1145, 1069, 1044, 988, 830, 755, 731, 641 cm$^{-1}$. LRMS (+ESI) m/z: 427 [(M+Na)$^+$, 100%]. MP: 204-206° C. HPLC purity: 98.23%, RT: 25.95 min.

Example 41: 4-(1-methyl-1,4,5,10-tetrahydrobenzo[b]pyrazolo[3,4-e][1,4]diazepine-5-carbonyl)benzoic acid (TAR-C076)

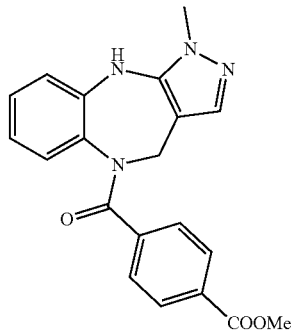 [SMILES: COC(=O)c1ccc(C(=O)N2Cc3cnn(C)c3Nc3ccccc32)cc1]

Treating diazepine 1 (2.0 g, 10.0 mmol) with the acid chloride derived from 4-(methoxycarbonyl)benzoic acid (1.98 g, 11.0 mmol) according to the above general procedure A followed by purification via flash column chromatography (silica. 1:99 to 1:9 v/MeOH/CH$_2$Cl$_2$ gradient elution) produced TAR-C076 (3.08 g, 85%) as a white powder (R$_f$=0.30 in 1:9 v/v MeOH/CH$_2$Cl$_2$).

$^1$H NMR (300 MHz, DMSO-d$_6$): δ 8.65 (s, 1H), 7.73 (d, J=8.0 Hz, 2H), 7.27 (d, J=7.9 Hz, 3H), 7.20 (s, 1H), 7.10 (t, J=7.6 Hz, 1H), 6.76 (d, J=7.8 Hz, 1H), 6.60 (t, J=7.5 Hz, 1H), 5.67 (d, J=14.6 Hz, 1H), 3.96 (d, J=14.6 Hz, 1H), 3.89 (s, 3H), 3.80 (s, 3H). LRMS (–ESI) m/z: 385 [(M+Na)$^+$, 100%]. MP: >300° C. purity: 95.80%, RT: 19.07 min.

Example 42: 4-(1-methyl-1,4,5,10-tetrahydrobenzo[b]pyrazolo[3,4-e][1,4]diazepine-5-carbonyl)benzoic acid (TAR-C077)

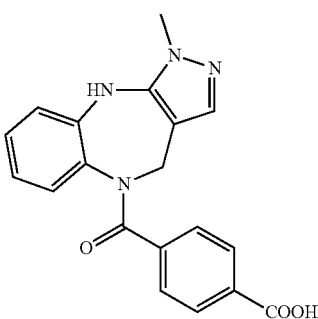 [SMILES: Cn1ncc2c1Nc1ccccc1N(C(=O)c1ccc(C(=O)O)cc1)C2]

The product from TAR-B048 (2.0 g, 5.50 mmol) and LiOH.H$_2$O (461 mg, 11.0 mmol) in MeOH/H$_2$O (55 mL of 1:1 v/v) was magnetically stirred for 16 h. The resulting mixture was concentrated to half volume and washed with CH$_2$Cl$_2$. The aqueous layer was acidified to pH 4 with 2 M HCL. The precipitate was collected by filtration to produce TAR-C077 (1.32 g, 69%) as a white powder. (R$_f$=0.05 in 1:9 v/v MeOH/CH$_2$Cl$_2$).

$^1$H NMR (300 MHz, DMSO-d$_6$): δ 8.90 (s. 1H), 7.63 (d, J=7.9 Hz, 2H), 7.41 (dd, J=8.2, 1.4 Hz, 1H), 7.16 (s, 1H), 7.06 (dd, J=8.5, 6.7 Hz, 3H), 6.69-6.64 (m, 1H), 6.58 (t, J=7.5 Hz, 1H), 5.67 (d, J=14.5 Hz, 1H), 3.90 (d, J=14.5 Hz, 1H), 3.81 (s, 3H), COOH signal not observed. $^{13}$C NMR (75 MHz, DMSO-d$_6$): δ 168.84, 168.45, 140.94, 139.97, 138.98, 136.60, 135.61, 132.26, 130.31, 128.19, 128.04, 126.27, 120.96, 119.60, 100.33, 43.05, 35.59. IR (diamond cell, neat) ν$_{max}$: 3310, 1608, 1579, 1555, 1503, 1386, 1294, 1255, 858, 742 cm$^{-1}$. LRMS (–ESI) m/z: 347 [(M–H)$^-$, 100%]. MP: >300° C. HPLC purity: 98.74%. RT: 16.55 min.

Example 43: (2-fluorophenyl)(1-methyl-4,10-dihydrobenzo[b]pyrazolo[3,4-e][1,4]diazepin-5 (1H)-yl)methanone (TAR-B075)

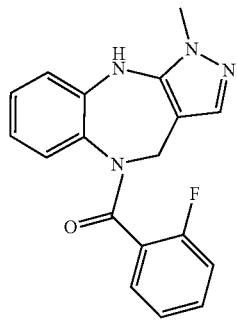

Treating diazepine 1 dihydrochloride (244 mg, 0.90 mmol) with the acid chloride derived from 2-fluorobenzoic acid (126 mg, 0.90 mmol) according to the above general procedure C followed by purification via flash column chromatography (silica, 1:99 to 1:9 v/MeOH/Cl$_2$Cl$_2$ gradient elution) produced TAR-B075 (264 mg, 91%) as a white powder (Rt=0.30 in 1:9 v/v MeOH/CH$_2$Cl$_2$).

$^1$H NMR (300 MHz, DMSO-d$_4$): δ 8.61 (s. 1H), 7.31-6.94 (m, 7H), 6.80 (dd, J=7.9, 1.5 Hz, 1H), 6.59 (td, J=7.5, 1.4 Hz, 1H), 5.61 (d, J=14.5 Hz, 1H), 3.96 (d, J=14.5 Hz, 1H), 3.76 (s, 3H). $^{13}$C NMR (75 MHz, DMSO-d$_6$): δ 164.46, 157.62 (d, J=246.4 Hz), 139.70, 139.04, 135.65, 130.94 (d, J=8.1 Hz), 130.47, 129.75, 128.45, 128.20 (d, J=3.7 Hz), 125.11 (d, J=17.5 Hz), 123.91 (d, J=3.4 Hz), 120.53, 119.49, 115.24 (d, J=21.1 Hz), 100.08, 42.87, 35.35. $^{19}$F NMR (282 MHz, DMSO-d$_6$) δ –115.23 (dt, J=11.4, 6.3 Hz). IR (diamond cell, neat) ν$_{max}$: 3295, 1627, 1560, 1504, 1397, 1318, 1223, 989, 830, 785, 756, 732, 640 cm$^{-1}$. LRMS (+ESI) m/z: 345 [(M+Na)$^+$, 100%]. MP: 287-290° C. HPLC purity: 99.37%, RT: 18.71 min.

Example 44: (4-fluorophenyl)(1-methyl-4,10-dihydrobenzo[b]pyrazolo[3,4-e][1,4]diazepin-5 (1H)-yl)methanone (TAR-B076)

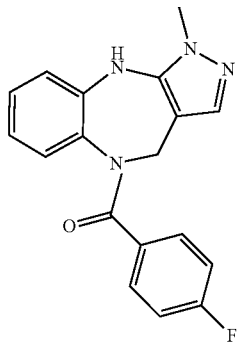

Treating diazepine 1 dihydrochloride (244 mg, 0.90 mmol) with the acid chloride derived from 4-fluorobenzoic acid (126 mg, 0.90 mmol) according to the above general procedure C followed by purification via flash column chromatography (silica. 1:99 to 1:9 v/MeOH/CH$_2$Cl$_2$ gradient elution) produced TAR-B076 (264 mg, 91%) as a white powder (R$_f$=0.30 in 1:9 v/v MeOH/CH$_2$Cl$_2$).

$^1$H NMR (300 MHz, DMSO-d$_6$): 8.67 (s. 1H), 7.31 (d, J=8.1 Hz, 1H), 7.19 (m. 3H), 7.12 (t, J=7.7 Hz, 1H), 7.00 (t, J=8.7 Hz, 2H), 6.73 (d, J=7.8 Hz, 1H), 6.64 (t, J=7.5 Hz, 1H), 5.67 (d, J=14.5 Hz, 1H), 3.92 (d, J=14.5 Hz, 1H), 3.78 (s, 3H). $^{13}$C NMR (75 MHz, DMSO-d$_6$): δ 168.27, 162.26 (d, J=247.4 Hz), 139.88, 138.81, 135.52, 132.80, 132.12, 130.40, 129.80 (d, J=8.6 Hz), 128.32, 121.20, 119.60, 114.67 (d, J=21.8 Hz), 100.39, 43.15, 35.37. $^{19}$F NMR (282 MHz, DMSO-d$_6$) δ −110.97 (td, J=8.8, 4.5 Hz). IR (diamond cell, neat) ν$_{max}$: 3281, 1624, 1558, 1503, 1390, 1318, 1233, 1164, 1140, 990, 854, 828, 755, 730 cm$^{-1}$. LRMS (+ESI) m/z: 345 [(M+Na)$^+$, 100%]. MP: 290-293° C. HPLC purity: 99.51%, RT: 19.14 min.

Example 45: (2-fluoro-5-(trifluoromethyl)phenyl)(1-methyl-4,10-dihydrobenzo[b]pyrazolo[3,4-e][1,4]diazepin-5 (1H)-yl)methanone (TAR-B077)

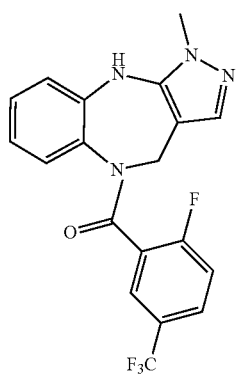

Treating diazepine 1 dihydrochloride (235 mg, 0.86 mmol) with the acid chloride derived from 2-fluoro-5-(trifluoromethyl)benzoic acid (180 mg, 0.86 mmol) according to the above general procedure C followed by purification via flash column chromatography (silica, 1:99 to 1:9 v/MeOH/CH$_2$Cl$_2$ gradient elution) produced TAR-B077 (295 mg, 81%) as a white powder (Rt=0.30 in 1:9 v/v MeOH/CH$_2$Cl$_2$).

$^1$H NMR (500 MHz, DMSO-d$_6$): 8.66 (s. 1H), 7.72-7.57 (m, 2H), 7.29 (t, J=8.9 Hz, 1H), 7.25 (dd, J=8.2, 1.4 Hz, 1H), 7.21 (s, 1H), 7.10 (ddd, J=8.2, 7.2, 1.5 Hz, 1H), 6.90 (d, J=1.5 Hz, 1H), 6.62 (td, J=7.6, 1.4 Hz, 1H), 5.63 (d, J=14.4 Hz, 1H), 4.02 (d, J=14.5 Hz, 1H), 3.77 (s, 3H). $^{13}$C NMR (125 MHz, DMSO-d$_6$): δ 162.94, 159.56 (d, J=253.3 Hz), 129.91, 129.79, 128.79, 128.43 (m), 126.17 (m),126.59, 126.00 (d, J=19.1 Hz), 124.98 (dq, J=32.6, 3.2 Hz). 124.43, 122.26, 120.57, 120.10, 119.45, 116.73 (d, J=22.9 Hz), 99.89, 43.02, 35.39. $^{19}$F NMR (282 MHz, DMSO-d$_6$) δ −60.75 (s, 3H), −109.21 (m, 1H). IR (diamond cell, neat) ν$_{max}$: 3324, 1627, 1566, 1504, 1437, 1396, 1324, 1298, 1267, 1174, 1146, 1116, 1071, 988, 902, 825, 781, 755, 664 cm$^{-1}$. LRMS (+ESI) m/z: 413 [(M+Na)$^+$, 100%], 391 [(M+H)$^+$, 10%]. MP: 257-259° C. HPLC purity: 99.91%, RT: 21.65 min.

Example 46: (2-fluoropyridin-3-yl)(1-methyl-4,10-dihydrobenzo[b]pyrazolo[3,4-e][1,4]diazepin-5 (1H)-yl)methanone (TAR-B078)

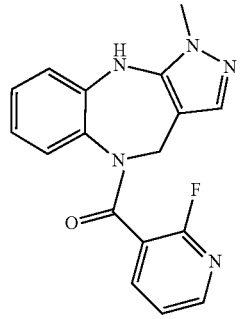

Treating diazepine 1 dihydrochloride (362 mg, 1.33 mmol) with the acid chloride derived from 2-fluoronicotinic acid (188 mg, 1.33 mmol) according to the above general procedure C followed by purification via flash column chromatography (silica, 1:99 to 1:9 v/MeOH/CH$_2$Cl$_2$ gradient elution) produced TAR-B078 (348 mg, 81%) as a white powder (R$_f$=0.30 in 1:9 v/v MeOH/CH$_2$Cl$_2$).

$^1$H NMR (300 MHz, DMSO-d$_6$): 8.60 (s, 1H), 8.14-7.97 (m, 1H), 7.78 (ddd, J=9.3, 7.3, 2.0 Hz, 1H), 7.28-7.17 (m, 3H), 7.15-7.01 (m, 1H), 6.86 (dd, J=7.9, 1.5 Hz, 1H), 6.62 (td, J=7.6, 1.4 Hz, 1H), 5.61 (d, J=14.5 Hz, 1H), 4.00 (d, J=14.5 Hz, 1H), 3.76 (s, 3H). $^{13}$C NMR (75 MHz, DMSO-d$_6$): δ 163.12, 157.67 (d, J=236.4 Hz), 148.05 (d, J=14.5 Hz). 139.75 (d, J=3.6 Hz), 139.62, 139.20, 135.64, 129.88, 128.74, 121.54 (d, J=4.3 Hz), 120.57, 120.15, 119.65 (d, J=33.6 Hz), 119.63, 119.63, 99.90, 43.02, 35.30. $^{19}$F NMR (282 MHz, DMSO-d$_6$) 5-69.04 (d, J=9.0 Hz). IR (diamond cell, neat) ν$_{max}$: 3328, 1630, 1567, 1504, 1433, 1412, 1301, 1245, 815, 772, 751, 620 cm$^{-1}$. LRMS (+ESI) m/z: 446 [(M+Na)$^+$, 100%], 324 [(M+H)$^+$, 10%]. MP: 268-271° C. HPLC purity: 99.58%, RT: 16.73 min.

Example 47: (2-fluoro-5-methoxyphenyl)(1-methyl-4,10-dihydrobenzo[b]pyrazolo[3,4-e][1,4]diazepin-5 (1H)-yl)methanone (TAR-B080)

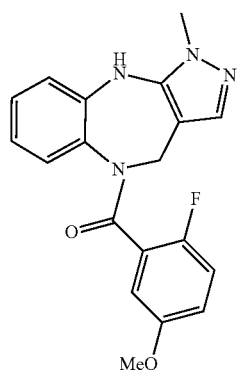

Treating diazepine 1 dihydrochloride (160 mg, 0.59 mmol) with the acid chloride derived from 2-fluoro-5-methoxybenzoic acid (100 mg, 0.59 mmol) according to the above general procedure C followed by purification via flash column chromatography (silica, 1:99 to 1:9 v/MeOH/CH₂Cl₂ gradient elution) produced TAR-B080 (208 mg, 92%) as a white powder (R$_f$=0.30 in 1:9 v/v MeOH/CH₂Cl₂).

¹H NMR (300 MHz, DMSO-d₆): 8.59 (s, 1H), 7.22 (dd, J=8.2, 1.4 Hz, 1H), 7.18 (s, 1H), 7.08 (ddd, J=8.2, 7.2, 1.6 Hz, 1H), 6.93 (t, J=9.0 Hz, 1H), 6.84 (dd, J=7.9, 1.5 Hz, 1H), 6.77 (ddd, J=9.1, 4.2, 3.2 Hz, 1H), 6.69-6.59 (m, 2H), 5.60 (d, J=14.5 Hz, 1H), 3.96 (d, J=14.5 Hz, 1H), 3.75 (s, 3H), 3.62 (s, 3H). ¹³C NMR (75 MHz, DMSO-d₆): δ 164.15, 154.65, 152.00 (d, J=239.2 Hz), 139.44 (d, J=39.2 Hz), 135.66, 130.66, 129.73, 128.55, 125.39 (d, J=19.4 Hz), 120.71, 119.46, 116.16 (d, J=6.5 Hz), 115.95 (d, J=8.6 Hz), 112.55, 99.99, 55.51. 42.85, 35.35. ¹⁹F NMR (282 MHz, DMSO-d₆) δ −126.31 (m). IR (diamond cell, neat) ν$_{max}$: 3305, 1632, 1561, 1501, 1446, 1420, 1392, 1317, 1277, 1251, 1208, 1102, 1037, 985, 870, 825, 781, 752, 728, 698, 628 cm⁻¹. LRMS (+ESI) m/z: 375 [(M+Na)⁺, 100%]. MP: 250-253° C. HPLC purity: 99.62%, RT: 19.29 min.

Example 48: (2-(2-fluoroethoxy)phenyl)(1-methyl-4,10-dihydrobenzo[b]pyrazolo[3,4-e][1,4]diazepin-5(1H)-yl)methanone (TAR-B086)

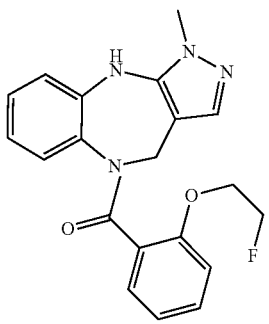

Treating diazepine 1 dihydrochloride (272 mg, 1.0 mmol) with the acid chloride derived from 2-(2-fluoroethoxy)benzoic acid (184 mg, 1.0 mmol) according to the above general procedure C followed by purification via flash column chromatography (silica, 1:99 to 1:9 v/MeOH/CH₂Cl₂ gradient elution) produced TAR-B086 (341 mg, 93%) as a white powder (R$_f$=0.30 in 1:9 v/v MeOH/CH₂Cl₂).

¹H NMR (300 MHz, DMSO-d₆): 8.61 (s, 1H), 7.27 (dd, J=8.1, 1.4 Hz, 1H), 7.18 (s, 1H), 7.15-7.00 (m, 2H), 6.86-6.78 (m. 1H), 6.78-6.71 (m. 3H), 6.64 (td, J=7.6, 1.4 Hz, 1H), 5.67 (d, J=14.5 Hz, 1H), 4.72 (dt, J=5.0, 2.5 Hz, 1H), 4.60 (dt, J=5.0, 2.5 Hz, 1H), 4.24-3.95 (m, 2H), 3.92 (d, J=14.5 Hz, 1H), 3.78 (s, 3H). ¹³C NMR (100 MHz, DMSO-d₆): δ 167.85, 157.30, 139.80, 138.96, 137.76, 135.63, 132.34, 130.29, 128.90, 128.26, 121.25, 119.86, 119.49, 115.79, 113.23, 100.21, 81.97 (d, J=166.8 Hz), 66.97 (d, J=19.1 Hz), 43.09, 35.37. ¹⁹F NMR (282 MHz, DMSO-d₆) 5-221.58 (m). IR (diamond cell, neat) vax: 3328, 1621, 1605, 1556, 1505, 1444, 1395, 1297, 1249, 1173, 1144, 1069, 1050, 991, 923, 880, 832, 761, 732, 634 cm⁻¹. LRMS (+ESI) m/z: 389 [(M+Na)⁺, 100%]. MP: 207-208° C. HPLC purity: 95.27%, RT: 18.29 min.

Example 49: (3-(2-fluoroethoxy)phenyl)(1-methyl-4,10-dihydrobenzo[b]pyrazolo[3,4-e][1,4]diazepin-5(1H)-yl)methanone (TAR-B087)

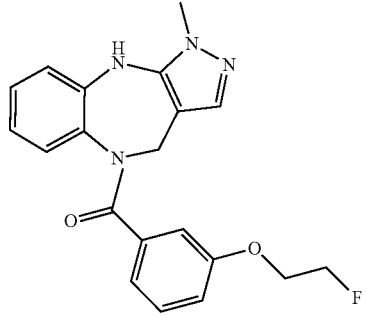

Treating diazepine 1 dihydrochloride (272 mg, 1.0 mmol) with the acid chloride derived from 3-(2-fluoroethoxy)benzoic acid (184 mg, 1.0 mmol) according to the above general procedure C followed by purification via flash column chromatography (silica, 1:99 to 1:9 v/MeOH/CH₂Cl₂ gradient elution) produced TAR-B087 (333 mg, 91%) as a white powder (R$_f$=0.30 in 1:9 v/v MeOH/CH₂Cl₂).

¹H NMR (300 MHz, DMSO-d₆): 8.61 (s, 1H), 7.27 (dd, J=8.1, 1.4 Hz, 1H), 7.18 (s, 1H), 7.14-7.04 (m, 2H), 6.86-6.79 (m, 1H), 6.78-6.70 (m. 3H), 6.64 (td, J=7.6, 1.4 Hz, 1H), 5.67 (d, J=14.5 Hz, 1H), 4.72 (dt, J=5.0, 2.5 Hz, 1H), 4.60 (dt, J=5.0, 2.5 Hz, 1H), 4.25-3.94 (m, 2H), 3.92 (d, J=14.5 Hz, 1H), 3.78 (s, 3H). ¹³C NMR (100 MHz, DMSO-d₆): δ 167.85, 157.30, 139.80, 138.96, 137.76, 135.63, 132.34, 130.29, 128.90, 128.26, 121.25, 119.86, 119.49, 115.79, 113.23, 100.21, 81.97 (d, J=166.8 Hz). 66.97 (d, J=19.1 Hz), 43.09, 35.37. ¹⁹F NMR (282 MHz, DMSO-d₆) δ −222.05 (tt, J=47.8, 30.1 Hz). IR (diamond cell, neat) ν$_{max}$: 3320, 1619, 1559, 1505, 1436, 1395, 1299, 1241, 1052, 990, 945, 881, 832, 815, 761, 693, 629 cm⁻¹. LRMS (+ESI) m/z: 389 [(M+Na)⁺, 100%]. MP: 207-208° C. HPLC purity: 99.19%, RT: 19.28 min.

Example 50: (4-(2-fluoroethoxy)phenyl)(1-methyl-4,10-dihydrobenzo[b]pyrazolo[3,4-e][1,4]diazepin-5(1H)-yl)methanone (TAR-B088)

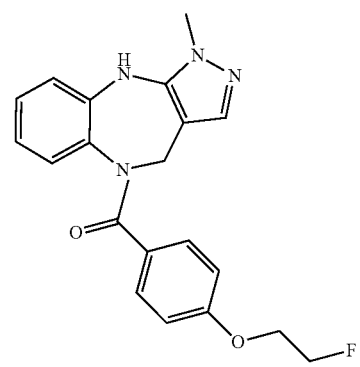

Treating diazepine 1 dihydrochloride (272 mg, 1.0 mmol) with the acid chloride derived from 4-(2-fluoroethoxy)benzoic acid (184 mg, 1.0 mmol) according to the above general procedure C followed by purification via flash column chromatography (silica, 1:99 to 1:9 v/MeOH/CH$_2$Cl$_2$ gradient elution) produced TAR-B088 (341 mg, 93%) as a white powder (R$_f$=0.30 in 1:9 v/v MeOH/CH$_2$Cl$_2$).

$^1$H NMR (300 MHz, DMSO-d$_6$): 8.58 (s, 1H), 7.30 (dd, J=8.1, 1.3 Hz, 1H), 7.21-7.01 (m, 411), 6.71 (dd, J=19.4, 9.6 Hz, 411). 5.73-5.54 (m, 111), 4.76 (t, J=3.8 Hz, 11), 4.66-4.54 (m, 1H), 4.17 (dt, J=30.0, 3.8 Hz, 2H), 3.89 (d, J=14.6 Hz, 1H), 3.77 (s, 3H)). $^{13}$C NMR (100 MHz, DMSO-d$_6$): δ 167.64, 158.85, 139.83, 138.71, 135.52, 132.63, 130.30, 129.44, 128.65, 128.04, 121.19, 119.56, 113.42, 100.42, 81.93 (d, J=166.7 Hz), 66.94 (d, J=18.9 Hz), 43.15, 35.27. $^{19}$F NMR (282 MHz, DMSO-d$_6$) δ −222.27 (tt, J=47.8, 30.0 Hz). IR (diamond cell, neat) ν$_{max}$: 3306, 1605, 1555, 1503, 1388, 1296, 1247, 1174, 1048, 990, 921, 878, 836, 759, 732, 633 cm$^{-1}$. LRMS (+ESI) m/z: 389 [(M+Na)$^+$, 100%]. MP: 193-195° C. HPLC purity: 99.36%, RT: 18.92 min.

Example 51: Cuban-1-yl)(1-methyl-4,10-dihydrobenzo[b]pyrazolo[3,4-e][1,4]diazepin-5 (1H)-yl)methanone (QB)

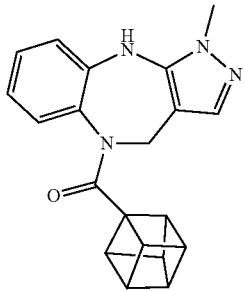 [SMILES: Cn1ncc2c1Nc1ccccc1N(C(=O)C13C4C5C6C4C1C6C53)C2]

Treating diazepine 1 dihydrochloride (154 mg, 0.56 mmol) with the acid chloride derived from cubane-1-carboxylic acid (100 mg, 0.67 mmol) according to the above general procedure C followed by purification via flash column chromatography (silica, 1:99 to 1:9 v/MeOH/CH$_2$Cl$_2$ gradient elution) produced QB (146 mg, 78%) as a white powder (R$_f$=0.50 in 1:9 v/v MeOH/CH$_2$Cl$_2$).

$^1$H NMR (300 MHz, Chloroform-d): δ 7.25-7.16 (m, 3H), 7.02-6.91 (m, 2H), 5.84 (s, 1H), 5.66 (d, J=15 Hz, 1H), 4.29 (s, 1H), 4.03 (s, 1H), 3.83 (s. 3H), 3.74 (s, 3H), 3.61 (s, 3H). IR (diamond cell, neat) ν$_{max}$: 3277, 2986, 1607, 1556, 1504, 1407, 1303, 1217, 1165, 986, 843, 761, 692, 581, 498, 445 cm$^{-1}$. LRMS (+ESI) m/z: 353 [(M+Na)$^+$, 100%]. MP: 194-203° C. HPLC purity: 95.87%. RT: 18.60 min.

Example 52: cycloheptyl(4,10-dihydrobenzo[b]pyrrolo[2,3-e][1,4]diazepin-5 (1H)-yl)methanone (CA7)

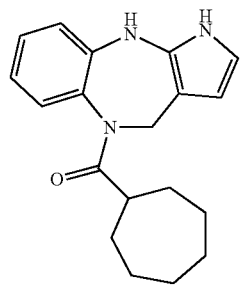 [SMILES: O=C(C1CCCCCC1)N1Cc2cc[nH]c2Nc2ccccc21]

Treating diazepine 1 dihydrochloride (152 mg, 0.59 mmol) with the acid chloride derived from cycloheptane carboxylic acid (100 mg, 0.70 mmol) according to the above general procedure C followed by purification via flash column chromatography (silica, 1:99 to 1:9 v/MeOH/CH$_2$Cl$_2$ gradient elution) produced CA7 (121 mg, 67%) as a white powder (R$_f$=0.50 in 1:9 v/v MeOH/CH$_2$Cl$_2$).

$^1$H NMR (300 MHz, Chloroform-d): δ 7.28-7.26 (m, 1H), 7.25-7.24 (m, 2H). 7.19-6.99 (m, 211). 5.98 (s, 111), 5.62 (d, J=15 Hz, 1H), 3.81 (d, J=15 Hz, 11H), 3.72 (s, 311), 2.35-2.31 (m, 1H), 1.81-1.67 (m, 4H), 1.57-1.23 (m, 8H). $^{13}$C NMR (75 MHz, Chloroform-d): δ 176.89, 139.21, 136.60, 132.40, 130.59, 129.12, 122.86, 119.78, 42.84, 42.37, 34.80, 31.54, 31.22, 28.24, 26.84, 26.70. IR (diamond cell, neat) ν$_{mx}$: 3287, 2917, 2852, 1632, 1609, 1556, 1499, 1432, 1398, 1306, 1281, 1228, 1163, 988, 819, 754, 718, 645, 582, 447 cm$^{-1}$. LRMS (+ESI) m/z: 347 [(M+Na)$^+$, 100%]. MP: 198-205° C. HPLC purity: 95.87%, RT: 20.61 min.

Example 53: methyl 4-(1-methyl-1,4,5,10-tetrahydrobenzo[b]pyrazolo[3,4-e][1,4]diazepine-5-carbonyl)bicyclo[2.2.2]octane-1-carboxylate (BcO-MC)

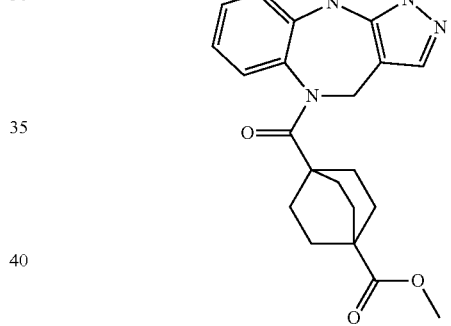

Treating diazepine 1 dihydrochloride (107 mg, 0.39 mmol) with the acid chloride derived from 4-(methoxycarbonyl)bicyclo[2.2.2]octane-1-carboxylic acid (100 mg, 0.47 mmol) according to the above general procedure C followed by purification via flash column chromatography (silica, 1:99 to 1:9 v/MeOH/CH$_2$Cl$_2$ gradient elution) produced BcO-MC (59 mg, 70%) as a white powder (R$_f$=0.50 in 1:9 v/v MeOH/CH$_2$Cl$_2$).

$^1$H NMR (300 MHz, DMSO-d$_6$): δ 8.43 (s, 1H), 7.32-7.28 (m. 2H), 7.22-7.20 (m, 1H), 7.05-6.98 (m, 2H), 5.43 (d, J=12 Hz, 1H), 3.69 (s, 3H), 3.63 (d, J=12 Hz, 1H), 3.50 (s, 3H), 1.69-1.62 (m, 3H), 1.50-1.36 (m, 9H). $^{13}$C NMR (75 MHz, DMSO-d$_6$): δ 176.90, 174.52, 140.37 139.13, 135.81, 132.96, 130.98, 128.90, 121.60, 120.18, 100.53, 51.42, 46.17, 40.82, 38.69, 37.75, 35.20, 27.50, 27.44. IR (diamond cell, neat) ν$_{max}$: 3274, 2947, 2872, 1726, 1614, 1594, 1553, 1501, 1386, 1280, 1252, 1080, 1017, 768, 593 cm$^{-1}$. LRMS (+ESI) m/z: 417 [(M+Na)$^+$, 100%]. MP: 198-211° C. HPLC purity: 98.64%, RT: 18.61 min.

Example 54: bicyclo[2.2.2]octan-1-yl(1-methyl-4, 10-dihydrobenzo[b]pyrazolo[3,4-e][1,4]diazepin-5 (1H)-yl)methanone (BcO)

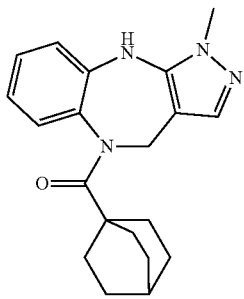 [SMILES: Cn1ncc2c1Nc1ccccc1N(C(=O)C13CCC(CC1)CC3)C2]

Treating diazepine 1 dihydrochloride (176 mg, 0.65 mmol) with the acid chloride derived from bicyclo[2.2.2]octane-1-carboxylic acid (100 mg, 0.65 mmol) according to the above general procedure C followed by purification via flash column chromatography (silica, 1:99 to 1:9 v/MeOH/CH$_2$Cl$_2$ gradient elution) produced BcO (142 mg, 65%) as a white powder (R$_f$=0.50 in 1:9 v/v MeOH/CH$_2$Cl$_2$).

$^1$H NMR (300 MHz, DMSO-d$_6$): δ 7.30 (m, 1H), 7.19 (m), 7.08 (d, J=7.6 Hz, 2H), 6.40 (s, 1H), 5.66 (d, J=14.6 Hz, 1H), 3.79 (br s, 4H), 1.82-1.23 (m, 12H), 1.00-0.76 (m, 1H). IR (diamond cell, neat) ν$_{max}$: 2940, 2921, 2863, 1685, 1409, 1292, 1270, 957, 910, 891, 748, 653, 542 cm$^{-1}$. LRMS (+ESI) m/z: 359 [(M+Na)$^+$, 100%]. HPLC purity: 96.87%, RT: 21.77 min.

Example 55: (1-methyl-4,10-dihydrobenzo[b]pyrazolo[3,4-e][1,4]diazepin-5 (1H)-yl)(naphthalen-2-yl)methanone (TRGA-81)

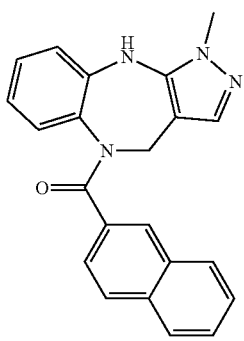 [SMILES: Cn1ncc2c1Nc1ccccc1N(C(=O)c1ccc3ccccc3c1)C2]

Treating diazepine 1 dihydrochloride (132 mg, 0.48 mmol) with the acid chloride derived from 2-naphthoic acid (100 mg, 0.58 mmol) according to the above general procedure C followed by purification via flash column chromatography (silica, 1:99 to 1:9 v/MeOH/CH$_2$Cl$_2$ gradient elution) produced TRGA-81 (139 mg, 81%) as a white powder (R$_f$=0.50 in 1:9 v/v MeOH/CH$_2$Cl$_2$).

$^1$H NMR (300 MHz, DMSO-d$_6$): δ 8.57 (s, 1H), 7.84 (d, J=6 Hz, 1H), 7.79 (d, J=18 Hz, 1H), 7.73-7.46 (m, 3H), 7.25-7.09 (m, 4H), 6.95-6.89 (m, 1H), 6.72 (d, J=9 Hz, 1H), 6.42-6.37 (m, 1H), 5.77 (d, J=15 Hz, 1H), 4.03 (d, J=15 Hz, 1H), 3.81 (s, 3H). $^{13}$C NMR (75 MHz, DMSO-d$_6$): δ 168.21, 139.73, 138.62, 135.80, 134.54, 132.62, 129.67, 129.60, 128.56, 128.27, 128.22, 128.01, 126.52, 126.07, 124.99, 124.43, 123.81, 120.54, 119.42, 100.49, 43.01, 35.38. IR (diamond cell, neat) ν$_{max}$: 3300, 1617, 1504, 1404, 1377, 1318, 833, 796, 780, 748, 725, 447 cm$^{-1}$. LRMS (+ESI) m/z: 377 [(M+Na)$^+$, 100%]. MP: 228-243° C. HPLC purity: 98.03%. RT: 19.10 min.

Example 56: (1-methyl-4,10-dihydrobenzo[b]pyrazolo[3,4-e][1,4]diazepin-5 (1H)-yl)(naphthalen-1-YI)methanone (TRGA-89)

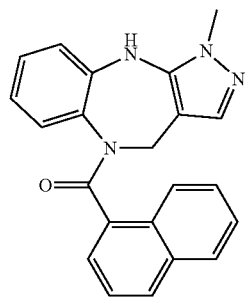 [SMILES: Cn1ncc2c1Nc1ccccc1N(C(=O)c1cccc3ccccc13)C2]

Treating diazepine 1 dihydrochloride (132 mg, 0.48 mmol) with the acid chloride derived from 1-naphthoic acid (100 mg, 0.58 mmol) according to the above general procedure C followed by purification via flash column chromatography (silica, 1:99 to 1:9 v/MeOH/CH$_2$Cl$_2$ gradient elution) produced TRGA-89 (141 mg, 82%) as a white powder (R$_f$=0.50 in 1:9 v/v MeOH/CH$_2$Cl$_2$).

$^1$H NMR (300 MHz, DMSO-d$_6$): δ 8.72 (s, 1H), 7.83 (d, 0.1=15 Hz, 3H), 7.67 (d, J=9 Hz, 1H), 7.51-7.20 (m, 5H), 7.09-7.04 (m, 1H), 6.77 (d, J=9 Hz, 1H), 6.57-6.52 (m, 1H), 5.99 (d, J=15 Hz, 1H), 4.03 (d, J=15 Hz, 1H), 3.85 (s, 3H). $^{13}$C NMR (75 MHz, DMSO-d$_4$): δ 168.18, 139.87, 138.99, 135.67, 133.91, 132.88, 132.26, 131.88, 130.47, 128.24, 128.24, 127.45, 127.45, 127.06, 126.94, 126.49, 124.34, 121.13, 119.57, 100.35, 43.21, 35.41. IR (diamond cell, neat) ν$_{am}$: 3312, 1610, 1565, 1505, 1402, 1298, 12.48, 1035, 820, 762, 728, 701, 477, 449 cm$^{-1}$. LRMS (+ESI) m/z: 377 [(M+Na)$^+$, 100%]. MP: 231-233° C. HPLC purity: 98.85%, RT: 20.51 min.

Example 57: benzo[d][1,3]dioxol-5-yl(1-methyl-4, 10-dihydrobenzo[b]pyrazolo[3,4-e][1,4]diazepin-5 (1H)-yl)methanone (TRGA-95)

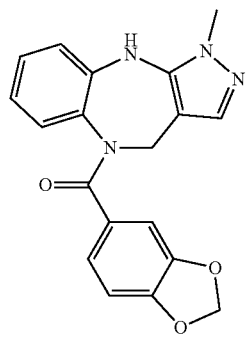 [SMILES: Cn1ncc2c1Nc1ccccc1N(C(=O)c1ccc3c(c1)OCO3)C2]

Treating diazepine 1 dihydrochloride (137 mg, 0.50 mmol) with the acid chloride derived from benzo[d][1,3]dioxole-5-carboxylic acid (100 mg, 0.60 mmol) according to the above general procedure C followed by purification via flash column chromatography (silica. 1:99 to 1:9 v/MeOH/ CH$_2$Cl$_2$ gradient elution) produced TRGA-95 (158 mg, 75%) as a white powder (R$_f$=0.50 in 1:9 v/v MeOH/ CH$_2$Cl$_2$).

$^1$H NMR (300 MHz, DMSO-d$_6$): δ 8.59 (s. 1H), 7.29 (d, J=9 Hz, 2H), 7.15 (d, J=9 Hz, 2H), 6.71 (br s, 4H), 5.96 (s, 2H), 5.66 (d, J=15 Hz, 1H), 3.89 (d, J=15 Hz, 1H), 3.76 (s, 3H). $^{13}$C NMR (75 MHz, DMSO-d$_6$): δ 167.46, 148.06, 146.52, 139.84, 138.72, 135.56, 132.67, 130.19, 129.97, 128.18, 122.16, 121.35, 119.61, 107.88, 107.45, 101.31, 100.31, 43.21, 35.32. LRMS (+ESI) m/z: 371 [(M+Na)$^+$, 100%]. HPLC purity: 99.53%, RT: 17.19 min.

Example 58: (4-ethylphenyl)(1-methyl-4,10-dihydrobenzo[b]pyrazolo[3,4-e][1,4]diazepin-5 (1H)-yl)methanone (TRGA-99)

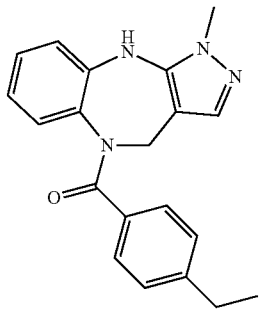 [SMILES: CCc1ccc(C(=O)N2Cc3cnn(C)c3Nc3ccccc32)cc1]

Treating diazepine 1 dihydrochloride (152 mg, 0.55 mmol) with the acid chloride derived from 4-ethylbenzoic acid (100 mg, 0.66 mmol) according to the above general procedure C followed by purification via flash column chromatography (silica, 1:99 to 1:9 v/MeOH/CH$_2$Cl$_2$ gradient elution) produced TRGA-99 (134 mg, 73%) as a white powder (R$_f$=0.50 in 1:9 v/v MeOH/CH$_2$Cl$_2$).

$^1$H NMR (300 MHz, DMSO-d$_6$): δ 8.59 (s, 1H), 7.28 (d, J=9 Hz, 1H), 7.16-6.98 (m, 6H), 6.72-6.63 (m, 2H), 5.68 (d, J=15 Hz, 1H), 3.89 (d, J=15 Hz, 1H), 3.77 (s, 3H), 2.50 (q, J=6 Hz, 2H), 1.08 (t, J=6 Hz, 3H). $^{13}$C NMR (75 MHz, DMSO-d$_6$): δ 168.10, 145.23, 139.84, 138.81, 135.60, 133.65, 132.53, 130.37, 128.15, 127.56, 126.95, 121.18, 119.54, 100.36, 43.14, 35.33, 27.78, 15.07. IR (diamond cell, neat) v$_1$: 2971, 1618, 1561, 1500, 1388, 1315, 1244, 1139, 1051, 1018, 983, 827, 757, 726, 629, 594, 489, 462 cm$^{-1}$. LRMS (+ESI) m/z: 355 [(M+Na)$^+$, 100%]. HPLC purity: 99.87%, RT: 19.63 min.

Example 59: (4-isopropylphenyl)(1-methyl-4,10-dihydrobenzo[b]pyrazolo[3,4-e][1,4]diazepin-5 (1H)-yl)methanone (TRGA-101)

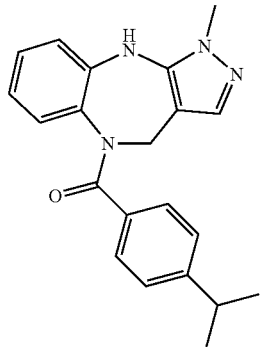 [SMILES: CC(C)c1ccc(C(=O)N2Cc3cnn(C)c3Nc3ccccc32)cc1]

Treating diazepine 1 dihydrochloride (139 mg, 0.51 mmol) with the acid chloride derived from 4-isopropylbenzoic acid (100 mg, 0.61 mmol) according to the above general procedure C followed by purification via flash column chromatography (silica, 1:99 to 1:9 v/MeOH/ CH$_2$Cl$_2$ gradient elution) produced TRGA-101 (129 mg, 73%) as a white powder (R$_f$=0.50 in 1:9 v/v MeOH/ CH$_2$Cl$_2$).

$^1$H NMR (300 MHz, DMSO-d$_6$): δ 8.59 (s, 1H), 7.30-7.01 (m, 7H), 6.73-6.61 (m, 2H), 5.68 (d, J=12 Hz, 1H), 3.89 (d, J=12 Hz, 1H), 3.77 (s, 3H), 2.78 (sep, J=6 Hz, 1H), 1.10 (d, J=6 Hz, 6H). $^{13}$C NMR (75 MHz, DMSO-d$_6$): δ 167.98, 152.92, 139.84, 138.80, 135.60, 133.71, 132.48, 130.38, 128.17, 127.65, 125.50, 121.15, 119.55, 100.38, 43.17, 35.33, 33.05, 23.60. IR (diamond cell, neat) v$_{max}$: 3283, 2958, 1601, 1556, 1502, 1392, 1317, 834, 753, 730 cm$^{-1}$. LRMS (+ESI) m/z: 369 [(M+Na)$^+$, 100%]. HPLC purity: 95.03%, RT: 20.64 min.

Example 60: (4-(tert-butyl)phenyl)(1-methyl-4,10-dihydrobenzo[b]pyrazolo[3,4-e][1,4]diazepin-5 (1H)-yl)methanone (TRGA-105)

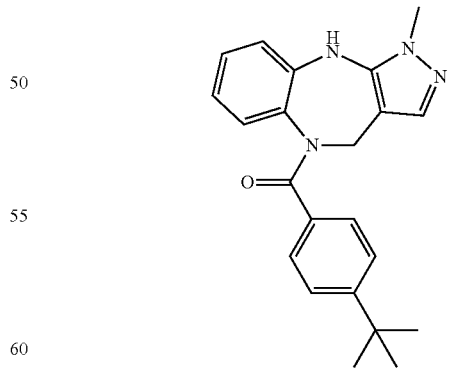

Treating diazepine 1 dihydrochloride (139 mg, 0.56 mmol) with the acid chloride derived from 4-(tert-butyl) benzoic acid (100 mg, 0.56 mmol) according to the above general procedure C followed by purification via flash column chromatography (silica, 1:99 to 1:9 v/MeOH/

CH$_2$Cl$_2$ gradient elution) produced TRGA-105 (158 mg, 78%) as a white powder (R$_f$=0.50 in 1:9 v/v MeOH/CH$_2$Cl$_2$).

$^1$H NMR (300 MHz, DMSO-d$_6$): δ 8.59 (s, 1H), 7.31-7.27 (m, 1H), 7.19-7.08 (m, 6H), 6.74-6.64 (m, 2H), 5.68 (d, J=15 Hz, 1H), 3.89 (d, J=15 Hz, 1H), 3.77 (s, 3H), 1.17 (s, 9H). $^{13}$C NMR (75 MHz, DMSO-d$_6$): δ 167.96, 152.16, 139.88, 138.80, 135.64, 133.33, 130.39, 129.17, 128.22, 127.50, 124.36, 121.18, 119.59, 100.47, 43.27, 35.35, 34.39, 30.87. IR (diamond cell, neat) v$_m$: 3313, 1607, 1556, 1504, 1392, 1294, 1143, 994, 827, 762, 749, 727, 708, 627, 601, 500, 448 cm$^{-1}$. LRMS (+ESI) m/z: 383 [(M+Na)$^+$, 100%]. HPLC purity: 99.78%, RT: 21.51 min.

Example 61: (1-methyl-4,10-dihydrobenzo[b]pyrazolo[3,4-e][1,4]diazepin-5 (1H)-yl)(2,2,3,3-tetramethylcyclopropyl)methanone (TRGA-111)

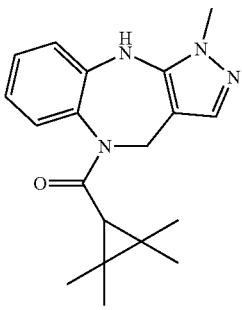 [SMILES: Cn1ncc2c1Nc1ccccc1N(C(=O)C1C(C)(C)C1(C)C)C2]

Treating diazepine 1 dihydrochloride (160 mg, 0.59 mmol) with the acid chloride derived from 2,2,3,3-tetramethylcyclopropane-1-carboxylic acid (100 mg, 0.70 mmol) according to the above general procedure C followed by purification via flash column chromatography (silica, 1:99 to 1:9 v/MeOH/CH$_2$Cl$_2$ gradient elution) produced TRGA-111 (129 mg, 68%) as a white powder (R$_f$=0.50 in 1:9 v/v MeOH/CH$_2$Cl$_2$).

$^1$H NMR (300 MHz, Chloroform-d): δ 7.26-7.18 (m, 2H), 7.12-7.09 (m, 1H), 7.04-6.95 (m, 2H), 5.95 (s, 1H), 5.66 (d, J=15 Hz, 1H), 3.80 (d, J=15 Hz, 1H), 3.73 (s, 3H), 1.67 (s, 1H), 1.23 (s, 3H), 1.19 (s. 3H), 0.94 (s, 3H), 0.81 (s, 3H). $^{13}$C NMR (75 MHz, Chloroform-d): δ 171.24, 139.07, 138.66, 136.55, 132.43, 131.40, 128.72, 122.33, 119.43, 102.29, 42.45, 36.69, 34.78, 28.48, 28.26, 23.81, 22.82, 17.63, 17.22. IR (diamond cell, neat) v$_{max}$: 3309, 2930, 1623, 1557, 1500, 1427, 1393, 1315, 1245, 986, 936, 833, 760, 723, 584 cm$^{-1}$. LRMS (+ESI) m/z: 347 [(M+Na)$^+$, 100%]. HPLC purity: 98.82%, RT: 20.46 min.

Example 62: 5-(3,4-Dimethylbenzyl)-1-methyl-1,4,5,10-tetrahydrobenzo[b]pyrazolo[3,4-e][1,4]diazepine (WJ05105)

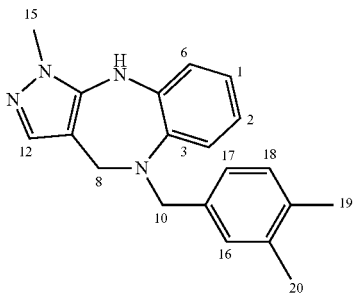 [SMILES: Cc1ccc(CN2Cc3cnn(C)c3Nc3ccccc32)cc1C]

A stirred solution of diazepine 1 (150 mg. 0.75 mmol) and 3,4 dimethylbenzaldehyde (100 mg, 0.75 mmol) in CH$_2$Cl$_2$ (10 mL) was treated portion wise with sodium triacetoxyborohydride (795 mg, 3.75 mmol) over 1 h and stirring continued for 12 h. The resultant suspension was diluted with CH$_2$Cl$_2$ (25 mL) and subsequently washed with NaHCO$_3$ (25 mL of a sat. aq. solution), brine (50 mL), dried (MgSO$_4$), filtered and concentrated under reduced pressure. The resultant oil was purified by flash column chromatography (silica. 2.5:97.5 v/v MeOH:CH$_2$Cl$_2$) and concentration of the relevant fractions (R$_f$=0.28 in a 2.5:97.5 v/v MeOH:CH$_2$Cl$_2$ solution) produced the title compound (211 mg, 88%) as a white powder.

$^1$H NMR (500 MHz, DMSO-d$_6$): 8.11 (br s, 1H, NH), 7.16 (dd, J=8.0, 1.5 Hz, 1H, 3-CH), 7.09-7.01 (m. 3H, 16/17/18-3×CH), 7.01-6.94 (m, 2H, 1/2-2×CH), 6.88 (s, 1H, 12-CH), 6.79 (ddd, J=7.9, 7.2, 1.5 Hz, 1H, 6-CH), 4.01 (s, 2H, 10-CH$_2$), 3.76 (s, 2H, 8-CH$_2$), 3.72 (s, 3H, 15-CH$_3$), 2.20-2.15 (m, 6H, 19/20-2×CH3). $^{13}$C NMR (126 MHz, DMSO-d$_6$): δ 141.2, 140.4, 139.1, 136.5, 135.7(1), 135.7(0), 134.5, 129.5, 129.2, 125.9, 125.6, 124.3, 120.9, 119.4, 100.4, 57.4, 48.5, 35.1, 19.4, 19.0. IR (diamond cell, neat) vax: 3269, 1603, 1554, 1503, 1431, 1393, 1363, 1332, 1294, 1252, 1132, 1020, 990, 856, 837, 819, 762, 714, 664, 640, 596, 556, 476, 443 cm 1. LRMS (+ESI) m/z: 319 [(M+H)$^+$, 100%]. HRMS (+ESI) Found: (M+H)$^+$, 319.1915. C$_{20}$H22N$_4$ requires (M+H)$^+$, 319.1917. MP 171-173° C. HPLC purity: 97.08%. RT: 17.48 min.

Example 63: 5-(3,5-Dimethoxybenzyl)-1,4,5,10-tetrahydrobenzo[b]pyrazolo[3,4-e][1,4]diazepine (WJ0625)

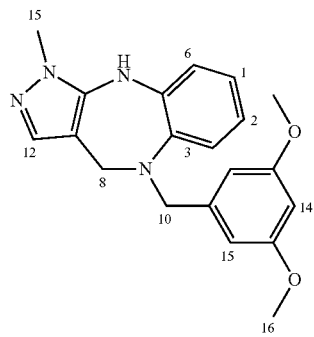 [SMILES: COc1cc(CN2Cc3cnn(C)c3Nc3ccccc32)cc(OC)c1]

A stirred solution of diazepine 1 (150 mg, 0.75 mmol) and 3,5-dimethoxybenzaldehyde (125 mg, 0.75 mmol) in CH$_2$Cl$_2$ (10 mL) was treated portion wise with sodium triacetoxyborohydride (795 mg, 3.75 mmol) over 1 h and stirring continued for 12 h. The resultant suspension was diluted with CH$_2$Cl$_2$ (25 mL) and subsequently washed with NaHCO$_3$ (25 mL of a sat. aq. solution), brine (50 mL), dried (MgSO$_4$), filtered and concentrated under reduced pressure followed by purification via flash column chromatography (silica, 2.5:97.5 v/v MeOH:CH$_2$Cl$_2$) produced the title compound (148 mg, 56%) as a white foam (R$_f$=0.1 in a 2.5:97.5 v/v MeOH:CH$_2$Cl$_2$ solution)

$^1$H NMR (500 MHz, DMSO-d$_6$): 8.14 (br s, 1H, NH), 7.17 (dd, J=8.1, 1.5 Hz, 1H, 3-CH), 7.06 (dd, J=8.0, 1.5 Hz, 1H, 6-CH), 6.97 (ddd, J=7.9, 7.2, 1.5 Hz, 1H, 2-CH), 6.92 (s, 1H, 12-CH), 6.80 (ddd, J=7.9, 7.2, 1.5 Hz, 1H, 1-CH), 6.46 (d, J=2.3 Hz, 2H, 15-2×CH), 6.33 (t, J=2.3 Hz, 1H, 14-CH), 4.07 (s, 2H, 10-CH$_2$), 3.79 (s, 2H, 8-CH$_2$). 3.73 (s, 3H, 15-CH$_3$), 3.67 (s, 6H, 16-2×CH3). $^{13}$C NMR (126 MHz, DMSO-d$_6$): δ 160.3, 141.8, 141.1, 140.5, 139.0, 135.7, 125.6, 124.3, 121.0, 119.4, 105.9, 100.5, 98.5, 57.6, 55.0, 49.0, 35.1. IR (diamond cell, neat) ν$_{max}$: 3309, 1626, 1560, 1504, 1429, 1392, 1317, 1247, 1146, 1029, 990, 827, 757, 741, 690, 636, 597, 493, 447 cm$^{-1}$. LRMS (+ESI) m/z: 351 [(M+H)$^+$, 100%]. HRMS (+ESI) Found: (M+Na)$^+$, 373.1636. C$_{20}$H$_{22}$N$_4$O$_2$ requires (M+Na)$^+$, 373.1635. MP 210-212° C. HPLC purity: 95.61%, RT: 16.93 min.

Example 64: 5-((1-Methyl-4,10-dihydrobenzo[b] pyrazolo[3,4-e][1,4]diazepin-5(1H)-yl)methyl)benzene-1,3-diol (WJ0627)

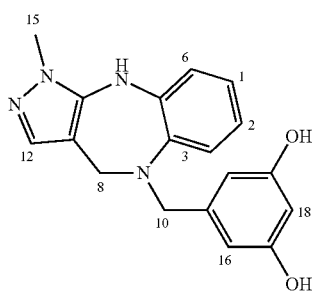 [SMILES: Cn1ncc2c1Nc1ccccc1N(Cc1cc(O)cc(O)c1)C2]

A stirred solution of diazepine 1 (150 mg, 0.75 mmol) and resorcinol (104 mg, 0.75 mmol) in CH$_2$Cl$_2$ (10 mL) was treated portion wise with sodium triacetoxyborohydride (795 mg. 3.75 mmol) over 1 h and stirring continued for 12 h. The resultant suspension was diluted with CH$_2$Cl$_2$ (25 mL) and subsequently washed with NaHCO$_3$ (25 mL of a sat. aq. solution), brine (50 mL), dried (MgSO$_4$), filtered and concentrated under reduced pressure followed by purification via flash column chromatography (silica, 2.5:97.5 v/v MeOH:CH$_2$Cl$_2$) produced the title compound (111 mg, 46%) as a white crystalline powder (R$_f$=0.04 in a 2.5:97.5 v/v MeOH:CH$_2$Cl$_2$ solution).

$^1$H NMR (400 MHz, DMSO-d$_6$): 9.09 (br d, J=2.2 Hz, 2H, 20H), 8.08 (br s, 1H, NH), 7.16 (dd, J=8.0, 1.5 Hz, 1H, 3-CH), 7.05 (dd, J=8.0, 1.5 Hz, 1H, 6-CH), 6.95 (td, J=7.6, 1.5 Hz, 1H, 2-CH), 6.90 (s. 1H, 12-CH), 6.81 (td, J=7.5, 1.5 Hz, 1H, 1-CH), 6.20 (d, J=2.1 Hz, 2H, 16-2×CH), 6.05 (t, J=2.2 Hz, 1H, 18-CH), 3.93 (s, 2H, 10-CH$_2$), 3.76 (s, 2H, 8-CH$_2$), 3.72 (s, 3H, 15-CH$_3$). $^{13}$C NMR (101 MHz, DMSO-d$_6$): δ 158.2, 141.5, 141.4, 140.5, 138.8, 135.7, 125.0, 124.1, 121.1, 119.5, 106.2, 101.2, 100.4, 57.9, 48.8, 35.1. IR (diamond cell, neat) ν$_{max}$: 3334, 1586, 1553, 1499, 1440, 1386, 1297, 1213, 1157, 1002, 956, 833, 762, 744, 688, 619, 559, 529, 439 cm$^{-1}$. LRMS (+ESI) m/z: 323 [(M+H)$^+$, 100%]. HRMS (+ESI) Found: (M+H)$^+$, 323.1503. C$_{18}$H$_{18}$N$_4$O$_2$ requires (M+H)$^+$, 323.1503. MP 236-238° C. HPLC purity: 95.51%, RT: 13.01 min.

Example 65; 5-((4-Chlorophenyl)sulfonyl)-1-methyl-1,4,5,10-tetrahydrobenzo[b]pyrazolo[3,4-e] [1,4]diazepine (WJ0633)

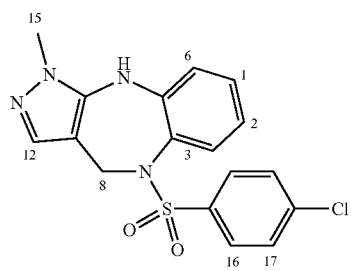

Treating diazepine 1 (200 mg, 1 mmol) with 4-chlorosulfonyl chloride (253 mg. 1.2 mmol) according to the above general procedure A (step ii) followed by purification via flash column chromatography (silica, 1:3 to 1:1 v/v EtOAc:hexanes gradient elution) produced the title compound (120 mg, 32%) as a white crystalline solid (R$_f$=0.26 in a 1:1 v/v EtOAc:hexanes solution).

$^1$H NMR (500 MHz, DMSO-d$_6$): 8.01 (s, 1H, NH), 7.36 (d, J=8.6 Hz, 2H, 16-2×CH), 7.29-7.22 (m, 2H, 2/6-2×CH), 7.10 (dd, J=8.6, 1.5 Hz, 1H, 3-CH), 7.05 (s, 1H, 12-CH), 7.02 (d, J=8.7 Hz, 2H, 17-2×CH), 6.94-6.87 (m, 1H, 1-CH), 4.97 (br s, 1H, 8-CH$_2$), 4.35 (br s, 1H, 8-CH$_2$). 3.27 (s, 3H, 15-CH$_3$). $^{13}$C NMR (126 MHz, DMSO-d$_6$): δ 139.4, 138.9, 138.0, 137.2, 135.6, 133.4, 129.5, 128.8, 128.1, 126.2, 120.2, 119.5, 100.0, 47.8, 34.6. IR (diamond cell, neat) ν$_{max}$: 3251, 1563, 1507, 1338, 1162, 1088, 1041, 997, 899, 847, 823, 762, 737, 701, 681, 616, 582, 567, 541, 474 cm$^{-1}$. LRMS (+APCI) m/z: 375 [(M+H)$^+$, 100%], 377 [(M+H)$^+$, 48%]. HRMS (+ESI) Found: (M+H)$^+$, 375.0677/377.0647. C$_{17}$H$_{15}$ClN$_4$O$_2$S requires (M+H)$^+$, 375.0677/377.0647. MP 206-208° C. HPLC purity: 95.43%, RT: 20.79 min.

Example 66: 1-Methyl-5-((4-(trifluoromethyl)phenyl)sulfonyl)-1,4,5,10-tetrahydrobenzo[b]pyrazolo [3,4-e][1,4]diazepine (WJ0639)

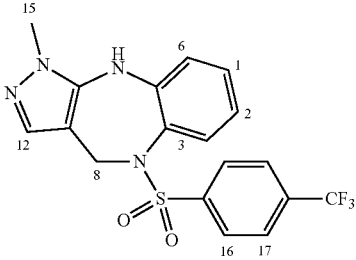

Treating diazepine 1 (200 mg, 1 mmol) with 4-trifluoromethylsulfonyl chloride (294 mg, 1.2 mmol) according to the above general procedure A (step ii) followed by purification via flash column chromatography (silica, 1.5:98.5 v/v MeOH:CH$_2$Cl$_2$) produced the title compound (210 mg, 51%) as a yellow crystalline solid (R$_f$=0.42 in a 1.5:98.5 v/v MeOH:CH$_2$Cl$_2$ solution).

$^1$H NMR (400 MHz, DMSO-d$_6$): 7.99 (s, 1H, NH), 7.67 (d, J=8.3 Hz, 2H, 17-2×CH), 7.35-7.21 (m. 4H, 2/6/16-4× CH), 7.11 (dd, J=8.6, 1.4 Hz, 1H, 3-CH), 7.06 (s, 1H, 12-CH), 6.93 (td, J=7.6, 1.4 Hz, 1H, 1-CH), 5.00 (br s, 1H, 8-CH$_2$), 4.38 (s, 1H, 8-CH$_2$), 3.16 (s, 3H, 15-CH$_3$). $^{13}$C NMR (101 MHz, DMSO-d$_6$): δ 143.1, 139.3, 138.7, 135.6, 133.4, 131.9 (q, J=32.1 Hz), 129.6, 127.9, 126.1, 125.1 (q, J=4.0 Hz), 123.5 (q, J=272.9 Hz), 120.3, 119.6, 100.1, 47.8, 34.3. $^{19}$F NMR (376 MHz, DMSO-d$_6$): δ −61.4. IR (diamond cell, neat) ν$_{max}$: 3543, 3195, 1620, 1563, 1508, 1319, 1163, 1090, 1058, 998, 900, 840, 785, 763, 710, 680, 609, 563, 540, 426 cm 1. LRMS (+APCI) m/z: 409 [(M+H)$^+$, 100%]. HRMS (+ESI) Found: (M+H)$^+$, 409.0941. C$_{18}$H$_{15}$F$_3$N$_4$O$_2$S requires (M+H)$^+$, 409.0941. MP 203-205° C. HPLC purity: 95.82%, RT: 21.26 min.

Example 67: 1-Methyl-5-tosyl-1,4,5,10-tetrahydrobenzo[b]pyrazolo[3,4-e][1,4]diazepine (WJ0641)

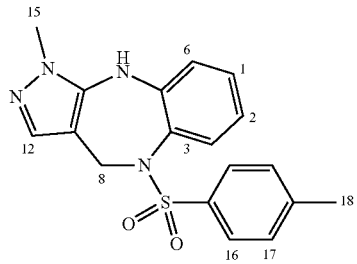

Treating diazepine 1 (200 mg, 1 mmol) with 4-methylsulfonyl chloride (228 mg. 1.2 mmol) according to the above general procedure A (step ii) followed by purification via flash column chromatography (silica, 1.5:98.5 v/v MeOH: CH$_2$Cl$_2$) produced the title compound (291 mg. 82%) as a white crystalline solid (R$_f$=0.48 in a 1.5:98.5 v/v MeOH: CH$_2$Cl$_2$ solution).

$^1$H NMR (300 MHz, DMSO-d$_6$): 7.92 (br s, 1H, NH), 7.22 (td, J=7.3, 1.5 Hz, 2H, 17-2×CH), 7.12-7.00 (m, 4H, 16/6/2-4×CH), 6.97-6.76 (m, 3H, 1/3/12-3×CH), 4.86 (br s, 1H, 8-CH$_2$), 4.40 (br s, 1H, 8-CH$_2$), 3.22 (s, 3H, 15-CH$_3$), 2.33 (s, 3H, 18-CH$_3$). $^{13}$C NMR (75 MHz, DMSO-d$_6$): δ 142.4, 139.7, 139.0, 136.3, 135.4, 133.4, 129.2, 128.4, 127.0, 126.4, 120.0, 119.3, 100.2, 47.7, 34.6, 20.9. IR (diamond cell, neat) ν$_{max}$: 3550, 3160, 1622, 1591, 1563, 1509, 1444, 1333, 1290, 1163, 1088, 1041, 996, 898, 844, 814, 754, 737, 702, 683, 659, 572, 555, 534, 500, 483 cm. LRMS (+APCI) m/z: 354 [(M+H)$^+$, 100%]. HRMS (+ESI) Found: (M+Na)$^+$, 377.1042. C$_{18}$H$_{18}$N$_4$O$_2$S requires (M+Na)$^+$, 377.1043. MP 184-186° C. HPLC purity: 97.72%, RT: 20.01 min.

Examples Testing the Selectivity of Compounds of Formula I

The following example demonstrates the selectivity of some of the compounds of Formula I for the OXTR over V1aR.

Generation of OTR and V$_{1a}$R-Expressing Human Embryonic Kidney (HEK) Cells

Human embryonic kidney cells (HEK-293) transfected to stably express untagged hOTR and V$_{1a}$R using the Flp-In™ T-REx™ system (Life Technologies, Carlsbad, Calif. USA) were established as reported in Jorgensen et al., 2016 (the entire disclosure of which is hereby incorporated by reference). Cells were subsequently maintained in 10% DMEM containing hygromycin (80 µg/ml), penicillin (100 U/ml), streptomycin (0.1 mg/ml) and blasticidine S hydrochloride (15 µg/ml).

Membrane Preparation

To induce receptor expression, cells were incubated with tetracycline (2 µg/mL) for 48 h. PBS with 5 mM EDTA (pH 7.4) was used to detach OTR and V$_{1a}$R-expressing HEK293 cells from culture flasks. Harvested cells were centrifuged at 1200 g for 5 min and were resuspended in homogenization buffer (50 mM HEPES, 5 mM EDTA, 5 mM MgCl$_2$; pH 7.4) prior to homogenization using an Ultra-Turrax homogeniser (IKA, Wilmington, N.C., USA). Homogenates were centrifuged three times for 30 min at 48.000 g, 4° C. for 30 min and membrane pellets resuspended in 50 mM Tris HCl, 5 mM MgCl$_2$ (pH 7.4). A bicinchoninic acid assay was used according to the manufacturer's protocol (Bio-Rad, Hercules. Calif., USA) to measure final protein concentration. Membranes were stored at −80° C. until use in competition radioligand binding studies.

Competition Radioligand Binding

Membranes (50□□g/well) were incubated with [Tyrosyl-2,6-$^3$H]-oxytocin (10 nM) or [Phenylalanyl-3,4,5-$^3$H]-vasopressin (8-L-arginine) (2 nM; Perkin Elmer, Waltham, Miss., USA) and logarithmically-spaced concentrations of competing compounds (1 nM-10 □M) in reaction buffer (50 mM Tris HCl, 5 mM MgCl$_2$, pH 7.4). Reactions were incubated for 90 min at 4° C. to reach equilibrium, and terminated by rapid filtration over glass fibre filters (Whatman GF/A 1.6 µM; Millipore, Darmstadt, Germany), and washing with ice-cold reaction buffer. Filters were dried, then incubated with Microscint 0 (Perkin Elmer) for 30 min before radioactivity was detected with a Microbeta2 2450 microplatereader (Perkin Elmer). Nonspecific binding was determined in the presence of 1 □M cold oxytocin or vasopressin (Sigma Aldrich), and was subtracted from total binding values to calculate specific binding values. Specific binding in the presence of compounds was expressed as a percentage of specific binding in the presence of vehicle control. A sum-of-squares F-test was used to compare the goodness of fit of one-site, two-site and sigmoidal with variable hill slope binding models, and to calculate K$_i$'s using Graphpad Prism (Graphpad Software, La Jolla, Calif., USA).

IP1 Accumulation Assays

OTR or V$_{1a}$R-expressing HEK-293 cells were seeded onto poly-L-lysine (100 µg/ml)-coated 384-well plates at a density of 8.75×10$^3$ cells per well. Cells were incubated in tetracycline (2 µg/mL) for 48 h to induce receptor expression. Intracellular IP1 levels induced by activation of the G$_q$ protein coupled to the OTR and V1aR was indexed using the HTRF IP-One kit (CisBio International, Bedford, Mass., USA), according to manufacturer's protocol. For agonist assessment, cells were incubated with logarithmically-spaced concentrations of compounds (1 nM-100 µM) for 1 h prior to the addition of Ab-Cryptate and IP1-d2 for 1 h. The contents of each well were transferred to a white-walled proxy plate (Perkin Elmer) and fluorescence read using a Pherastar Microplate reader (BMG Labtech, Cary, N.C., USA). For antagonist assessment, cells were incubated an ~EC$_{70}$ concentration of OT (30 nM) or AVP (25 nM) mixed with compounds (1 nM-100 μM) or vehicle control for 1 h. IP1 levels in the presence of compounds and OT or AVP were expressed as a percentage of levels seen with OT or AVP in the presence of vehicle control. Concentration response curves for OT and AVP were determined after 5 min incubation in drug or vehicle, and the data fitted using GraphPad PRISM to a 4-parameter logistic equation of the form y=Min+(Max−Min)/(1+10^((logEC$_{50}$−X)*n)) where X is drug concentration and n is the H-ill slope. Data represent the mean±s.d. of at least 3 independent experiments, each in duplicate.

The following compounds were assessed to determine selectivity for OXTR over V1aR, the results of which are summarised in Table 1 below:

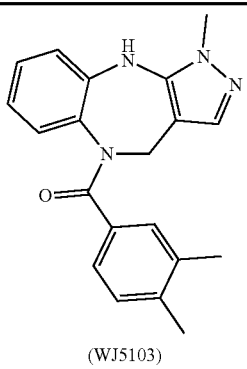

(WJ5103)

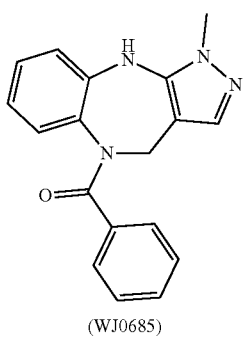 [SMILES: Cn1ncc2c1Nc1ccccc1N(C(=O)c1ccccc1)C2]

(WJ0685)

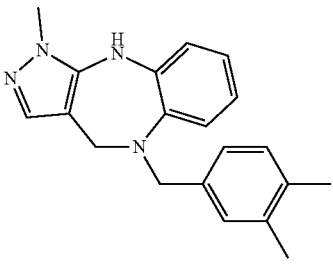

(WJ05105)

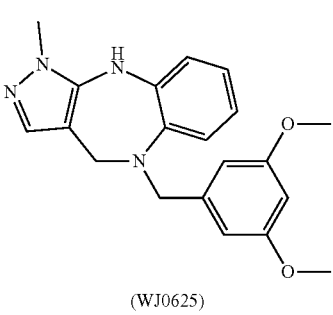 [SMILES: COc1cc(CN2Cc3cnn(C)c3Nc3ccccc32)cc(OC)c1]

(WJ0625)

-continued

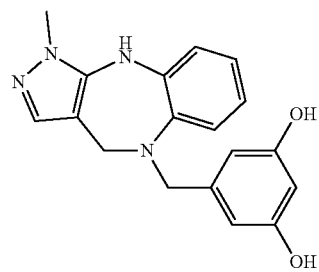

(WJ0627)

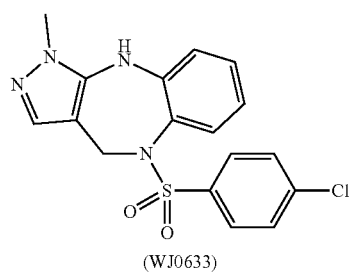 [SMILES: Cn1ncc2c1Nc1ccccc1N(S(=O)(=O)c1ccc(Cl)cc1)C2]

(WJ0633)

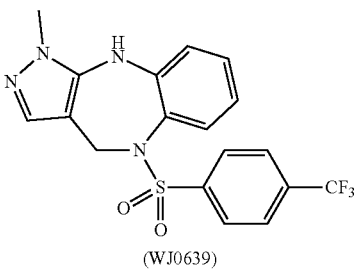 [SMILES: Cn1ncc2c1Nc1ccccc1N(S(=O)(=O)c1ccc(C(F)(F)F)cc1)C2]

(WJ0639)

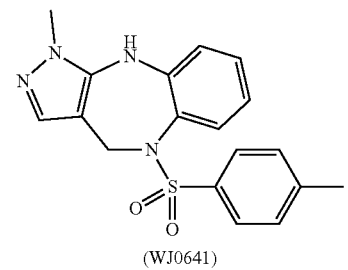

(WJ0641)

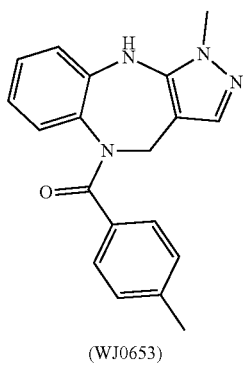 [SMILES: Cc1ccc(C(=O)N2Cc3cnn(C)c3Nc3ccccc32)cc1]

(WJ0653)

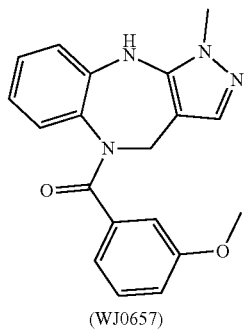 [SMILES: COc1cccc(C(=O)N2Cc3cnn(C)c3Nc3ccccc32)c1]
(WJ0657)
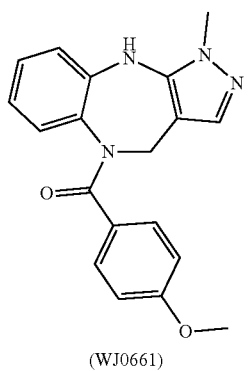 [SMILES: COc1ccc(C(=O)N2Cc3cnn(C)c3Nc3ccccc32)cc1]
(WJ0661)
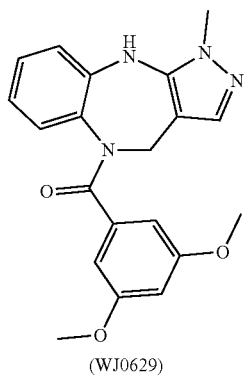 [SMILES: COc1cc(OC)cc(C(=O)N2Cc3cnn(C)c3Nc3ccccc32)c1]
(WJ0629)
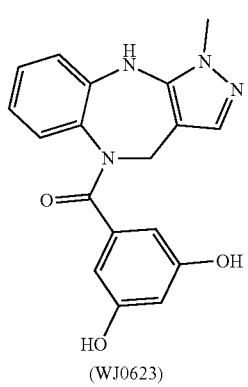 [SMILES: Cn1ncc2c1Nc1ccccc1N(C(=O)c1cc(O)cc(O)c1)C2]
(WJ0623)
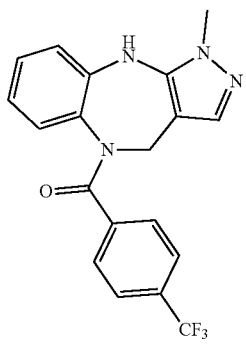
(WJ0677)
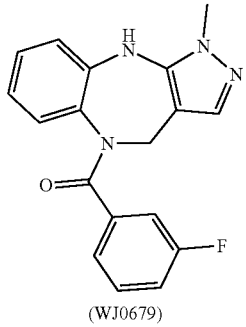 [SMILES: Cn1ncc2c1Nc1ccccc1N(C(=O)c1cccc(F)c1)C2]
(WJ0679)
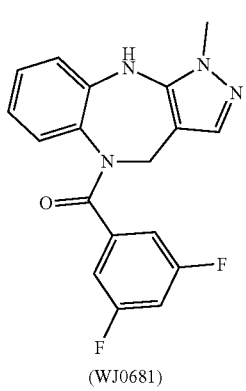 [SMILES: Cn1ncc2c1Nc1ccccc1N(C(=O)c1cc(F)cc(F)c1)C2]
(WJ0681)
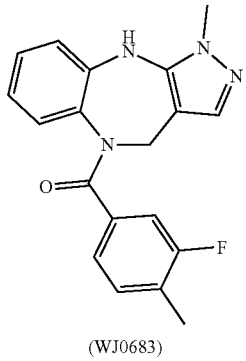 [SMILES: Cc1ccc(C(=O)N2Cc3cnn(C)c3Nc3ccccc32)cc1F]
(WJ0683)

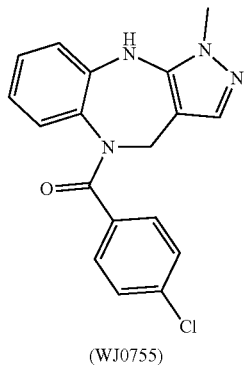 [SMILES: Cn1ncc2c1Nc1ccccc1N(C(=O)c1ccc(Cl)cc1)C2]
(WJ0755)
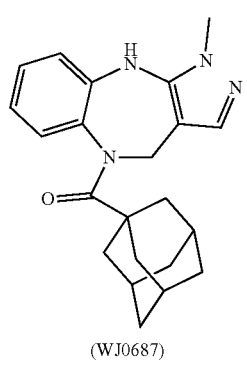 [SMILES: CNC1=C(C=N)CN(C(=O)C23CC4CC(CC(C4)C2)C3)c2ccccc2N1]
(WJ0687)
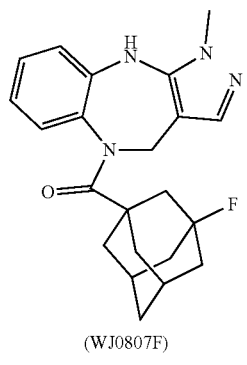 [SMILES: CNC1=C(C=N)CN(C(=O)C23CC4CC(CC(F)(C4)C2)C3)c2ccccc2N1]
(WJ0807F)
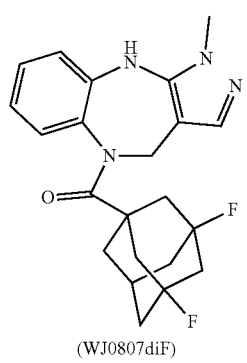 [SMILES: CNC1=C(C=N)CN(C(=O)C23CC4CC(F)(CC(F)(C4)C2)C3)c2ccccc2N1]
(WJ0807diF)
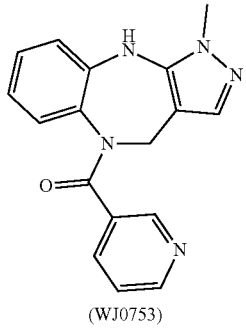
(WJ0753)
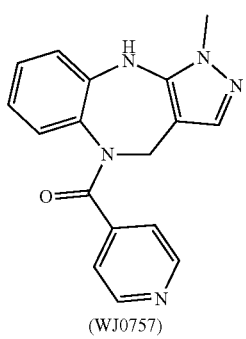 [SMILES: Cn1ncc2c1Nc1ccccc1N(C(=O)c1ccncc1)C2]
(WJ0757)
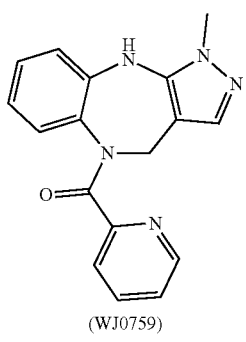
(WJ0759)
(WJ07117Me)

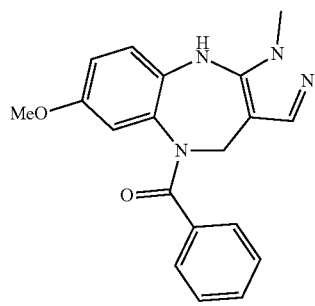
(WJ07117MeO)
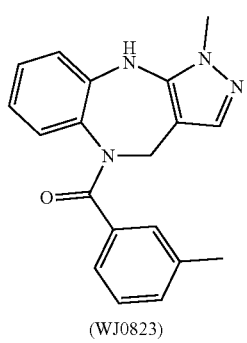 [SMILES: Cc1cccc(C(=O)N2Cc3cnn(C)c3Nc3ccccc32)c1]
(WJ0823)
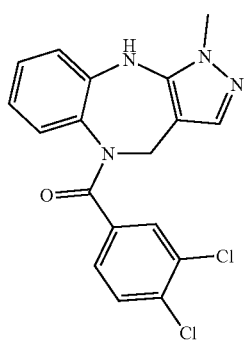
(WJ0824)
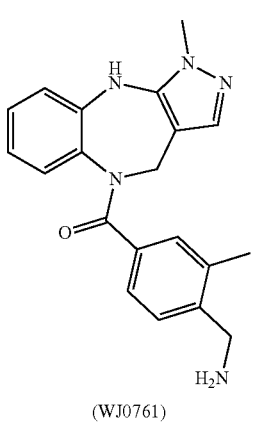 [SMILES: Cc1cc(C(=O)N2Cc3cnn(C)c3Nc3ccccc32)ccc1CN]
(WJ0761)
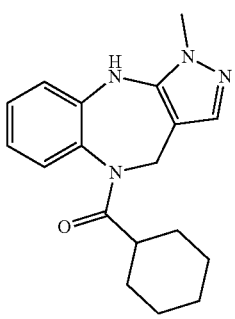
(CA6)
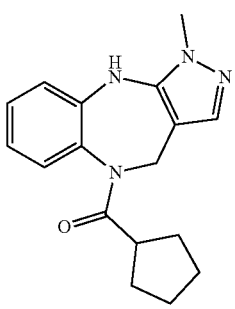
(CA5)
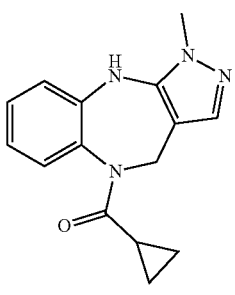
(CA3)

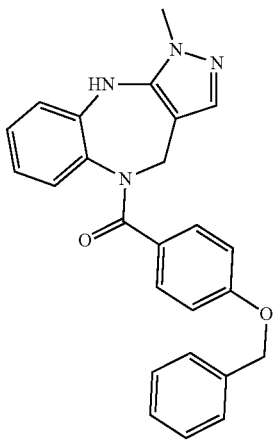

(BzE)

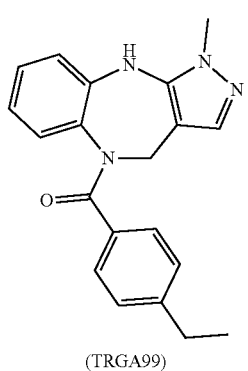 [SMILES: CCc1ccc(C(=O)N2Cc3cnn(C)c3Nc3ccccc32)cc1]

(TRGA99)

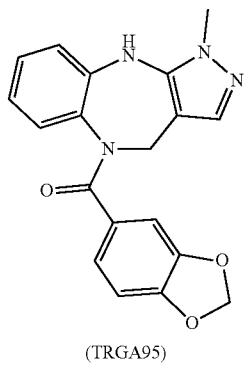 [SMILES: Cn1ncc2c1Nc1ccccc1N(C(=O)c1ccc3c(c1)OCO3)C2]

(TRGA95)

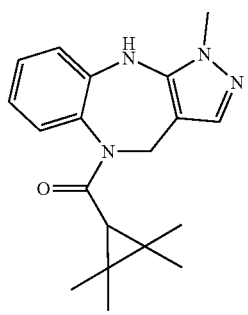

(TRGA111)

TABLE 1

| WJ-X Code | Ki OXTR (nM) | Ki V1aR (nM) | EC50 OXTR agonist (nM) | EC50 V1aR (nM) | IC50 OXTR (nM) | IC50 V1aR (nM) | OXTR Emax (nM) | OXTR Emax (% OXT) | O/V Ki | OV function |
|---|---|---|---|---|---|---|---|---|---|---|
| WAY | 230 ± 31 | 27 ± 3 | 420 ± 59 | >10,000 | n/a | 613 ± 206 | | 45 | 8.5 | 0.69 |
| WJ5103 | 117.2 ± 12.4 | 14 ± 2 | 109.3 ± 17.7 | >10,000 | n/a | 346.3 ± 90.91 | 147.0 ± 64.3 | 5.87 | 8.4 | 0.37 |
| WJ0685 | >10,000 | 81.6 ± 12.6 | 846.7 ± 244 | >10,000 | n/a | >10,000 | 297.7 ± 71.3 | 11.89 | | OT only |
| WJ05105 | >10,000 | >10,000 | >10,000 | >10,000 | >10,000 | >10,000 | | n/a | n/a | n/a |
| WJ0625 | >10,000 | >10,000 | >10,000 | >10,000 | >10,000 | >10,000 | | n/a | n/a | n/a |
| WJ0627 | >10,000 | >10,000 | >10,000 | >10,000 | >10,000 | >10,000 | | n/a | n/a | n/a |
| WJ0633 | >10,000 | >10,000 | >10,000 | >10,000 | >10,000 | >10,000 | | n/a | n/a | n/a |
| WJ0639 | >10,000 | >10,000 | >10,000 | >10,000 | >10,000 | >10,000 | | n/a | n/a | n/a |
| WJ0641 | >10,000 | >10,000 | >10,000 | >10,000 | >10,000 | >10,000 | | n/a | n/a | n/a |
| WJ0653 | 149 ± 43.4 | 12.4 ± 2.4 | 85.3 ± 26.5 | >10,000 | n/a | 710.0 ± 266.6 | 238.8 ± 38.7 | 9.54 | 12.0 | 0.12 |
| WJ0657 | 842.35 ± 288.09 | 107.7 ± 23.5 | 337.7 ± 76.5 | >10,000 | n/a | 745.7 ± 158.4 | 124.9 ± 16.8 | 4.99 | 7.8 | 0.45 |
| WJ0661 | 272.2 ± 87.6 | 24.0 ± 3.4 | 197 ± 60.3 | >10,000 | n/a | 462.2 ± 135.7 | 203.8 ± 54.8 | 8.14 | 11.3 | 0.43 |
| WJ0629 | 315.6 ± 79.2 | 12.9 ± 1.5 | >10,000 | >10,000 | 1765.7 ± 14.4 | 94.8 ± 7.7 | n/a | n/a | 24.5 | 18.63 |
| WJ0623 | 92.6 ± 10.0 | 4.6 ± 1.3 | >10,000 | >10,000 | 1760 ± 10 | 204.8 ± 57.6 | n/a | n/a | 20.1 | 8.59 |
| WJ0677 | 559.9 ± 111.2 | 96.9 ± 33.5 | 179.0 ± 37.8 | >10,000 | n/a | >10,000 | 193.3 ± 11.3 | 7.72 | 5.0 | OT only |
| WJ0679 | 422.138 ± 129.0 | 105.2 ± 10.5 | 406 ± 74 | >10,000 | n/a | 2202.67 ± 511.5 | 316 ± 108 | 12.62 | 4.0 | 0.18 |
| WJ0681 | 755.1 ± 164.0 | 47.8 ± 9.4 | 521.3 ± 35.2 | >10,000 | n/a | 2207 ± 405.7 | 272.7 ± 69.4 | 10.90 | 15.8 | 0.24 |
| WJ0683 | 102.6 ± 31 | 7.8 ± 0.9 | 96.2 ± 22.9 | >10,000 | n/a | 1137.3 ± 165 | 283.7 ± 22.4 | 11.33 | 13.1 | 0.085 |
| WJ0755 | 519.4 ± 109.7 | 173.6 ± 57.4 | 152.4 ± 47.3 | >10,000 | n/a | 1672.7 ± 298.5 | 255 ± 59.7 | 10.19 | 3.0 | 0.09 |
| WJ0687 | >10,000 | 377.0 ± 106.3 | 4881 ± 141 | >10,000 | n/a | >10,000 | 834 ± 61.1 | 33.32 | >26.5 | OT only |
| WJ0807mF | >10,000 | 1093.7 ± 58.3 | 2404.7 ± 652.2 | >10,000 | n/a | >10,000 | 632.5 ± 148 | 25.27 | >10 | OT only |
| WJ0807dF | >10,000 | 2215 | 4149 ± 1342.2 | >10,000 | n/a | >10,000 | 667.7 ± 219.4 | 26.68 | >4.5 | OT only |

TABLE 1-continued

| WJ-X Code | Ki OXTR (nM) | Ki V1aR (nM) | EC50 OXTR agonist (nM) | EC50 V1aR (nM) | IC50 OXTR (nM) | IC50 V1aR (nM) | OXTR Emax (nM) | OXTR Emax (% OXT) | O/V Ki | OV function |
|---|---|---|---|---|---|---|---|---|---|---|
| WJ0753 | >10,000 | 353 | 3534 ± 634 | >10,000 | >10,000 | >10,000 | 242.1 ± 21.7 | 9.67 | >28.3 | OT only |
| WJ0757 | >10,000 | 751.1 ± 196.5 | >10,000 | >10,000 | >10,000 | >10,000 | n/a | n/a | >13.3 | n/a |
| WJ0759 | >10,000 | 1118.0 ± 260.3 | >10,000 | >10,000 | >10,000 | >10,000 | n/a | n/a | >8.9 | n/a |
| WJ07117Me | 4071.7 ± 1219.9 | 924 | >10,000 | >10,000 | >10,000 | >10,000 | n/a | n/a | 4.4 | n/a |
| WJ07117MeO | >10,000 | 374 | >10,000 | >10,000 | >10,000 | >10,000 | n/a | n/a | >26.7 | n/a |
| WJ0823 | 552.9 ± 154.6 | | 407 ± 102 | >10,000 | n/a | >10,000 | 420 ± 37 | 16.78 | | OT only |
| WJ0824 | 1619.3 ± 243.3 | 455.0 ± 112.2 | 438 ± 126.8 | >10,000 | n/a | >10,000 | 321.8 ± 103.3 | 12.86 | 3.55 | OT only |
| WJ0761 | >10,000 | 44.7 ± 5.0 | 9191.7 ± 1615.8 | >10,000 | n/a | >10,000 | | 8 | >223.7 | <0.92 |
| CA6 (KA) | 1080 ± 323 | 236 ± 75 | 481 ± 61 | >10,000 | n/a | >10,000 | | 17 | 4.6 | <0.04 |
| CA5 (KA) | >10,000 | 553 ± 67 | 3395 ± 448 | >10,000 | n/a | >10,000 | | 10 | >18.1 | <0.33 |
| CA3 (KA) | >10,000 | 3370 ± 740 | >10,000 | >10,000 | >10,000 | >10,000 | | n/a | >3.0 | n/a |
| BzE | 176 ± 41 | 35 ± 5 | >10,000 | >10,000 | 179 ± 35 | 1591 ± 486 | | n/a | 5 | 0.11 |
| TRGA99 | 22 ± 8 | 1.8 ± 0.6 | 41 ± 15 | >10,000 | n/a | 1649 ± 75 | | 8 | 12.2 | 0.02 |
| TRGA95 | 159 ± 32 | 18 ± 1 | 91 ± 25 | >10,000 | n/a | 1530 ± 444 | | 13 | 8.8 | 0.06 |
| TRGA111 | >10,000 | >10,000 | >10,000 | >10,000 | >10,000 | >10,000 | | n/a | n/a | n/a |

Example Testing Effect of WJ0679 on Murine Social Interaction (N=46)

Species: *Mus musculus*
Strain: BALB/c
Sex: Male
Age: 6-7 weeks at testing
Vehicle: 88% isotonic saline, 10% DMSO, 2% tween 80
Compound: WJ0629
Doses: 0, 1, 5, 20 mg/kg
Route of administration: intraperitoneal (i.p.) injection Mice were placed in the arena (40×40×40 cm) in weight and treatment matched pairs of unfamiliar mice for a 10 min test session, commencing 30 min after receiving their i.p. injection. The variables of interest were the time the mice spent in close physical contact with each other and the time each mouse spent engaged in active social investigation (sniffing the other mouse).

FIG. 1 shows that all doses of WJ0679 significantly increased time spent in close physical contact, with the effect being most pronounced at the lower doses (1 and 5 mg/kg).

Figure 2:
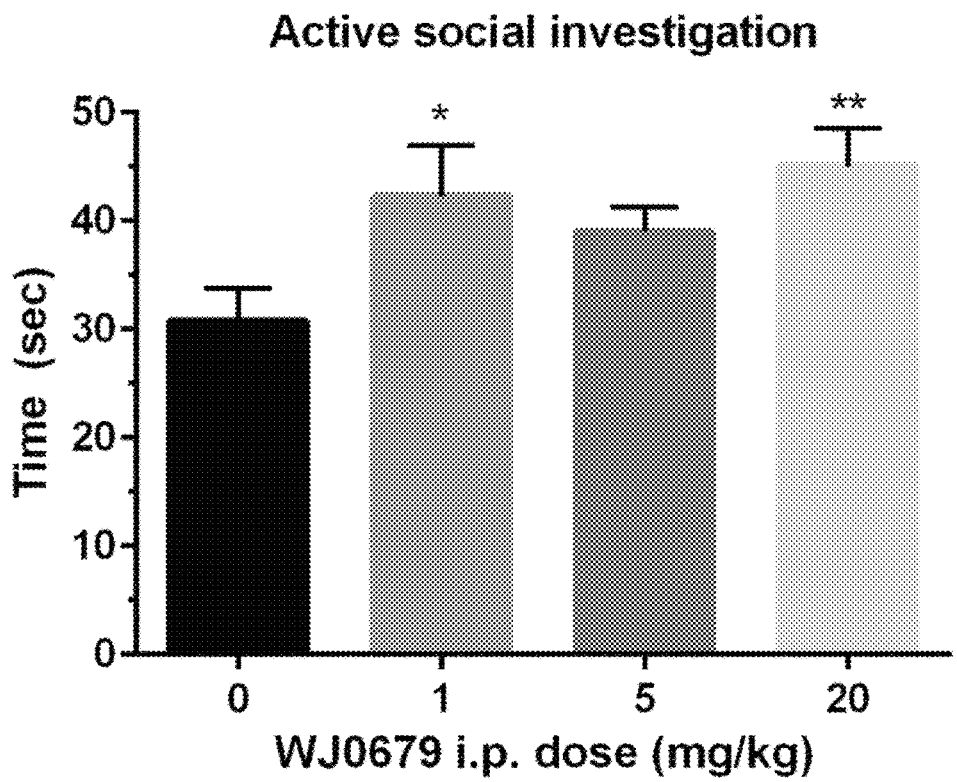
FIG. 2: Graph showing results of active social investigation time for mice treated with 0, 1, 5, and 20 mg/kg of a pharmaceutical composition including compound WJ0679.

FIG. 2 shows that doses of 1 and 20 mg/kg WJ0679 significantly increased active social investigation.

What is claimed is:

1. A pharmaceutical composition comprising: a pharmaceutically acceptable compound of Formula I and a pharmaceutically acceptable carrier, diluent, or excipient:

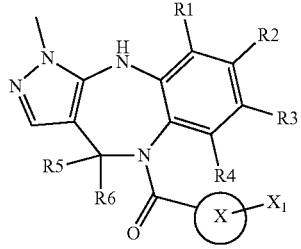

Formula I wherein R1, R3, R4, R5, and R6 are each independently selected from the group consisting of: H, F, Cl, Br, I, NH₂, NO₂, OH, ON=O, substituted or unsubstituted C$_1$-C$_4$ alkyl, substituted or unsubstituted C$_2$-C$_4$ alkenyl, substituted or unsubstituted C$_2$-C$_4$ alkynyl, substituted or unsubstituted —OC$_1$-C$_4$ alkyl, substituted or unsubstituted —OC$_2$-C$_4$ alkenyl, substituted or unsubstituted —OC$_2$-C$_4$ alkynyl, substituted or unsubstituted —NHC$_1$-C$_4$ alkyl, substituted or unsubstituted —NHC$_2$-C$_4$ alkenyl, substituted or unsubstituted —NHC$_2$-C$_4$ alkynyl, a substituted or unsubstituted aryl, and a substituted or unsubstituted heterocyclyl;

wherein R2 is selected from the group consisting of: H, F, Br, I, NH$_2$, NO$_2$, OH, ON=O, substituted methyl, substituted or unsubstituted C$_2$-C$_4$ alkyl, substituted or unsubstituted C$_2$-C$_4$ alkenyl, substituted or unsubstituted C$_2$-C$_4$ alkynyl, substituted or unsubstituted —OC$_1$-C$_4$ alkyl, substituted or unsubstituted —OC$_2$-C$_4$ alkenyl, substituted or unsubstituted —OC$_2$-C$_4$ alkynyl, substituted or unsubstituted —NHC$_1$-C$_4$ alkyl, substituted or unsubstituted —NHC$_2$-C$_4$ alkenyl, substituted or unsubstituted —NHC$_2$-C$_4$ alkynyl, a substituted or unsubstituted aryl, and a substituted or unsubstituted heterocyclyl;

wherein each R1, R2, R3, R4, R5, or R6 that is a substituted aryl or a substituted heterocyclyl includes one or more substituent(s) selected from the group consisting of F, Cl, Br, I, NH$_2$, N=O, NO$_2$, NHCH$_3$, OH, OCH$_3$, OC≡N, ON=O, SH, SCH$_3$, S(=O)$_n$OH, S(=O)$_n$CH$_3$, SC≡N, COOH, CH$_3$, CH$_m$F$_{(3-m)}$, CH$_m$Cl$_{(3-m)}$, CH$_m$Br$_{(3-m)}$, OCH$_3$, OCH$_m$F$_{(3-m)}$, OCH$_m$Cl$_{(3-m)}$, and OCH$_m$Br$_{(3-m)}$;

wherein X is a cyclic structure selected from the group consisting of: a fused or unfused aryl; a fused or unfused heterocyclyl; and a fused or unfused cycloalkyl; and wherein X1 represents one to three atoms or moieties independently selected from the group consisting of: H, F, Cl, Br, I, NH$_2$, NO$_2$, OH, ON=O, substituted or unsubstituted C$_1$-C$_4$ alkyl, substituted or unsubstituted C$_2$-C$_4$ alkenyl, substituted or unsubstituted C$_2$-C$_4$ alkynyl, substituted or unsubstituted —OC$_1$-C$_4$ alkyl, substituted or unsubstituted —OC$_2$-C$_4$ alkenyl, substituted or unsubstituted —OC$_2$-C$_4$ alkynyl, substituted or unsubstituted —NHC$_1$-C$_4$ alkyl, substituted or unsubstituted —NHC$_2$-C$_4$ alkenyl, substituted or unsubstituted —NHC$_2$-C$_4$ alkynyl, —COOH, —C$_1$ alkyl- COOH, —COOC$_1$-C$_2$ alkyl, —COOC$_1$-C$_2$ alkaryl, —C$_1$ alkyl-COOC$_1$-C$_2$ alkyl, —C$_1$-C$_2$ alkaryl, —OC$_1$-C$_2$ alkaryl, —NC$_1$-C$_2$ alkaryl, —C$_1$-C$_2$ alkyl-heterocyclyl, —OC$_1$-C$_2$ alkyl-heterocyclyl, and —NC$_1$-C$_2$ alkyl-heterocyclyl;
wherein each alkyl, alkenyl, alkynyl, alkaryl, or alkyl-heterocyclyl that is independently substituted with one or more substituent selected from the group consisting of: F, Cl, Br, I, ≡N, =NH, NH$_2$, N=O, NO$_2$, NHCH$_3$, N=C=O, N=C=S, =O, OH, OCH$_3$, OC≡N, ON=O, =S, SH, SCH$_3$, S(=O)$_n$OH, S(=O)$_n$CH$_3$, and SC≡N;
wherein each m is an integer selected from 0, 1, and 2; and each n is an integer selected from 0, 1, and 2.

2. The pharmaceutical composition of claim 1, wherein the cyclic structure is selected from the group consisting of: fused or unfused aryl groups; fused or unfused 5, 6-, or 7-membered heterocyclic groups having one or more hetero ring atoms selected from N, O, and S; and a 5, 6, 7, 8, 9, 10, 11, 12, 13, 14, 15-, or 16-membered mono-, bridged bi-, or bridged tri-cycloalkyl groups.

3. The pharmaceutical composition of claim 1, wherein: the aryl group is an unfused aryl group, the heterocyclic group is an unfused heterocyclic group having only a single hetero ring atom, and the cycloalkyl is a bridged bi- or tri-cyclic alkyl group.

4. The pharmaceutical composition of claim 1, wherein the cyclic structure is selected from the group consisting of: phenyl, pyridyl, and adamantyl.

5. The pharmaceutical composition of claim 1, wherein R1, R3, R4, R5, and R6 are each independently selected from the group consisting of: H, F, Cl, Br, I, OH, CH$_3$, CH$_m$F$_{(3-m)}$, CH$_m$Cl$_{(3-m)}$, CH$_m$Br$_{(3-m)}$, OCH$_3$, OCH$_m$F$_{(3-m)}$, OCH$_m$Cl$_{(3-m)}$, and OCH$_m$Br$_{(3-m)}$.

6. The pharmaceutical composition of claim 1, wherein R2 is independently selected from the group consisting of: H, F, Br, I, OH, CH$_m$F$_{(3-m)}$, CH$_m$Cl$_{(3-m)}$, CH$_m$Br$_{(3-m)}$, OCH$_3$, OCH$_m$F$_{(3-m)}$, OCH$_m$Cl$_{(3-m)}$, and OCH$_m$Br$_{(3-m)}$.

7. The pharmaceutical composition of claim 1, wherein the fused or unfused aryl at X is a phenyl of the form:

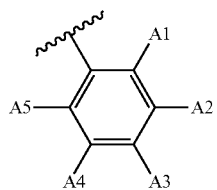

wherein each A1, A2, A3, A4, or A5 is independently selected from the group consisting of: H, F, Cl, Br, I, NH$_2$, NO$_2$, OH, ON=O, substituted or unsubstituted C$_1$-C$_4$ alkyl, substituted or unsubstituted C$_2$-C$_4$ alkenyl, substituted or unsubstituted C$_2$-C$_4$ alkynyl, substituted or unsubstituted —OC$_1$-C$_4$ alkyl, substituted or unsubstituted —OC$_2$-C$_4$ alkenyl, substituted or unsubstituted —OC$_2$-C$_4$ alkynyl, substituted or unsubstituted —NHC$_1$-C$_4$ alkyl, substituted or unsubstituted —NHC$_2$-C$_4$ alkenyl, and substituted or unsubstituted —NHC$_2$-C$_4$ alkynyl; and
wherein optionally one or more of A1 and A2, and/or A2 and A3, and/or A3 and A4, and/or A4 and A5 together form a fused ring structure.

8. The pharmaceutical composition of claim 7, wherein A1, A2, A3, A4, or A5 are each independently selected from the group consisting of: H, F, Cl, Br, I, NH$_2$, NO$_2$, OH, ON=O, substituted or unsubstituted C$_1$-C$_2$ alkyl, substituted or unsubstituted C$_2$ alkenyl, substituted or unsubstituted C$_2$ alkynyl, substituted or unsubstituted —OC$_1$-C$_2$ alkyl, substituted or unsubstituted —OC$_2$ alkenyl, substituted or unsubstituted —OC$_2$ alkynyl, substituted or unsubstituted —NHC$_1$-C$_2$ alkyl, substituted or unsubstituted —NHC$_2$ alkenyl, and substituted or unsubstituted —NHC$_2$ alkynyl.

9. The pharmaceutical composition of claim 8, wherein A1, A2, A3, A4, or A5 are each independently selected from the group consisting of: H, F, Cl, Br, I, OH, CH$_3$, CH$_m$F$_{(3-m)}$, CH$_m$Cl$_{(3-m)}$, CH$_m$Br$_{(3-m)}$, OCH$_3$, OCH$_m$F$_{(3-m)}$, OCH$_m$Cl$_{(3-m)}$, and OCH$_m$Br$_{(3-m)}$.

10. The pharmaceutical composition of claim 1, wherein the fused or unfused heterocyclyl at X is selected from the group consisting of:

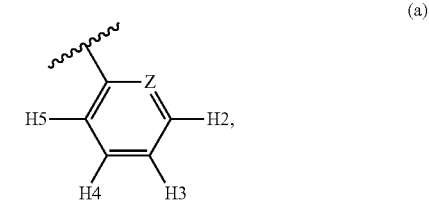

(a)

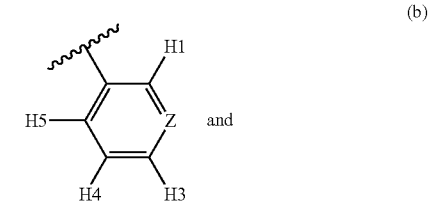

(b)

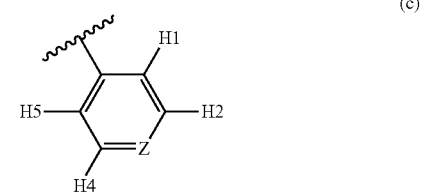

(c)

wherein:
Z is the hetero ring atom, and is selected from the group consisting of N, S, and O; and
each H1, H2, H3, H4, or H5 that is present is independently selected from the group consisting of: H, F, Cl, Br, I, NH$_2$, NO$_2$, OH, ON=O, substituted or unsubstituted C$_1$-C$_4$ alkyl, substituted or unsubstituted C$_2$-C$_4$ alkenyl, substituted or unsubstituted C$_2$-C$_4$ alkynyl, substituted or unsubstituted —OC$_1$-C$_4$ alkyl, substituted or unsubstituted —OC$_2$-C$_4$ alkenyl, substituted or unsubstituted —OC$_2$-C$_4$ alkynyl, substituted or unsubstituted —NHC$_1$-C$_4$ alkyl, substituted or unsubstituted —NHC$_2$-C$_4$ alkenyl, substituted or unsubstituted —NHC$_2$-C$_4$ alkynyl; and
wherein optionally one or more of H1 and H2, and/or H2 and H3, and/or H3 and H4, and/or H4 and H5 together form a fused ring structure.

11. The pharmaceutical composition of claim 10, wherein Z is N.

12. The pharmaceutical composition of claim 10, wherein each H1, H2, H3, H4, or H5 that is present is independently selected from the group consisting of: H, F, Cl, Br, I, NH$_2$, NO$_2$, OH, ON=O, substituted or unsubstituted C$_1$-C$_2$ alkyl, substituted or unsubstituted $C_2$ alkenyl, substituted or unsubstituted $C_2$ alkynyl, substituted or unsubstituted —$OC_1$-$C_2$ alkyl, substituted or unsubstituted —$OC_2$ alkenyl, substituted or unsubstituted —$OC_2$ alkynyl, substituted or unsubstituted —$NHC_1$-$C_2$ alkyl, substituted or unsubstituted —$NHC_2$ alkenyl, and substituted or unsubstituted —$NHC_2$ alkynyl.

13. The pharmaceutical composition of claim 12, wherein each H1, H2, H3, H4, or H5 that is present is independently selected from the group consisting of: H, F, Cl, Br, I, OH, $CH_3$, $CH_mF_{(3-m)}$, $CH_mCl_{(3-m)}$, $CH_mBr_{(3-m)}$, $OCH_3$, $OCH_mF_{(3-m)}$, $OCH_mCl_{(3-m)}$, and $OCH_mBr_{(3-m)}$.

14. The pharmaceutical composition of claim 1, wherein the compound is selected from the group consisting of:

(i)
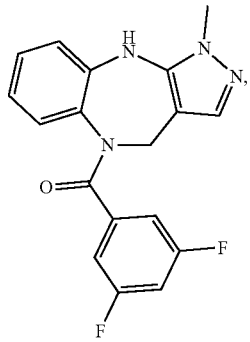

(ii)
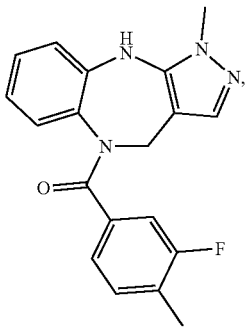

(iii)
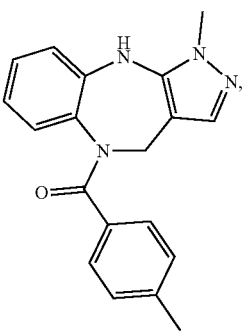

(iv)
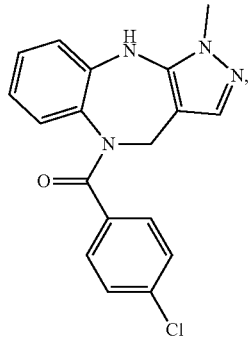

(v)
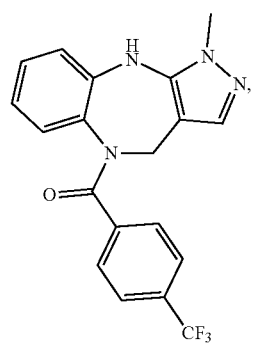

(vi)
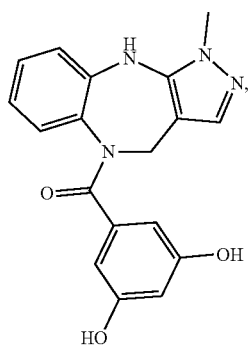

(vii)
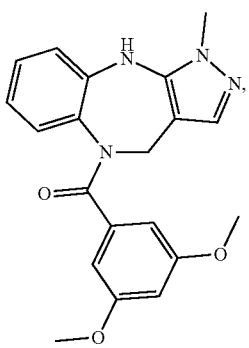

79
-continued
(viii)
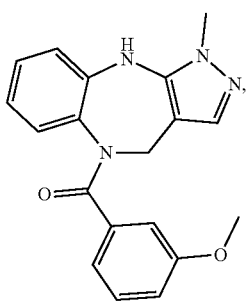
(ix)
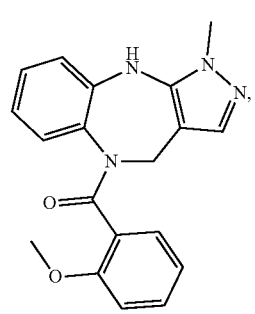
(x)
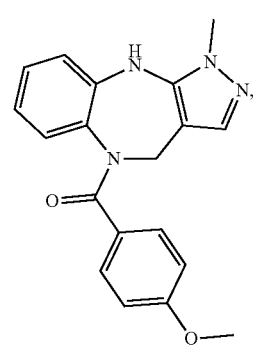
(xi)
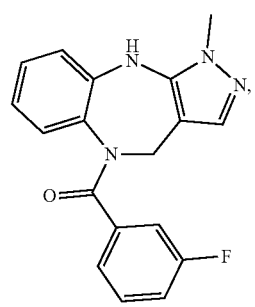
(xii)
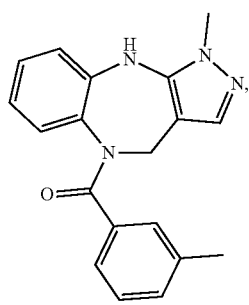
80
-continued
(xiii)
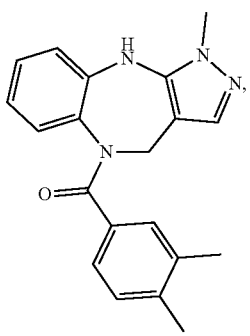
(xiv)
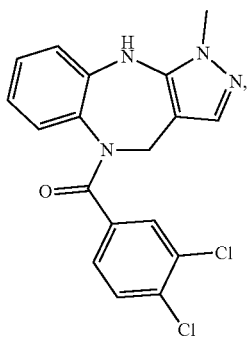
(xv)
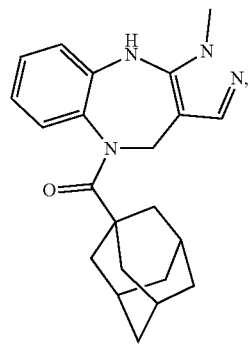
(xvi)
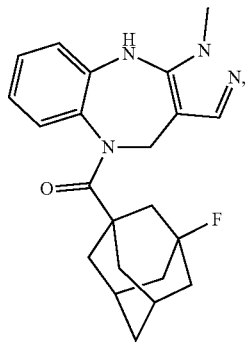

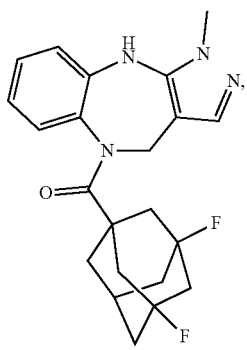
(xvii)
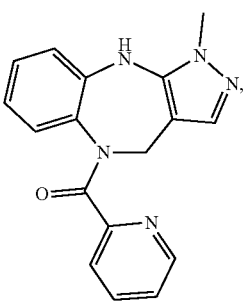
(xviii)
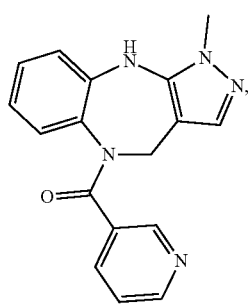
(xix)
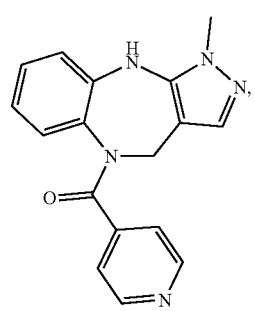
(xx)
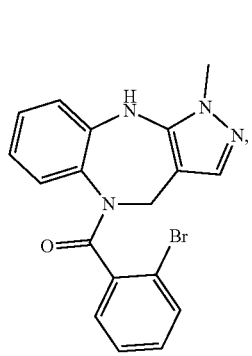
(xxi)

-continued
(xxvii)
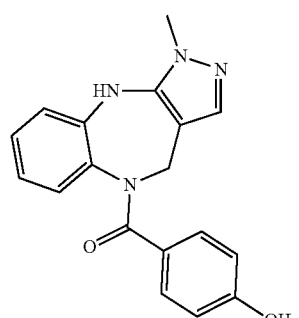
(xxviii)
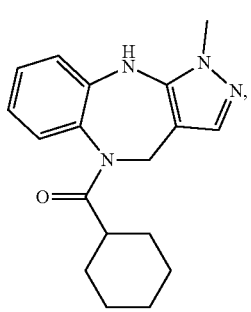
(xxix)
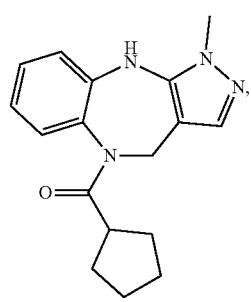
(xxx)
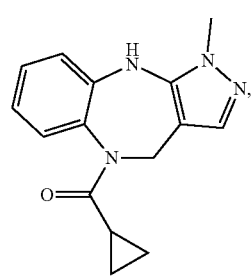
(xxxi)
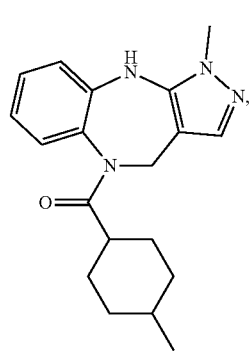
-continued
(xxxii)
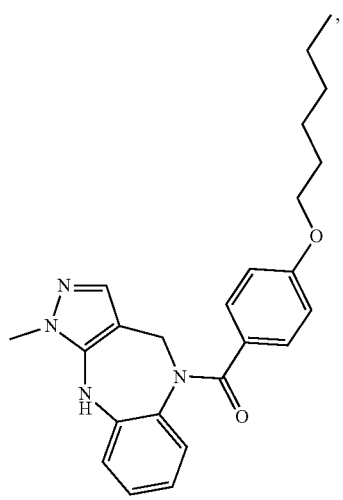
(xxxiii)
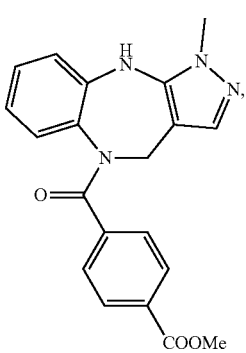
(xxxiv)
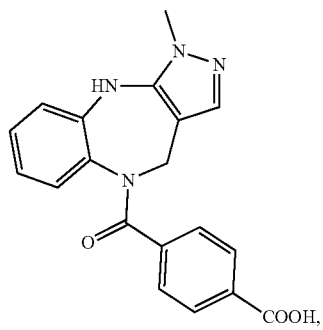
(xxxv)
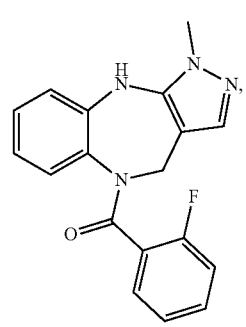

(xxxvi)
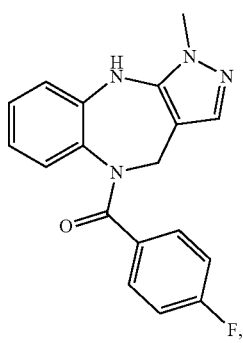
(xxxvii)
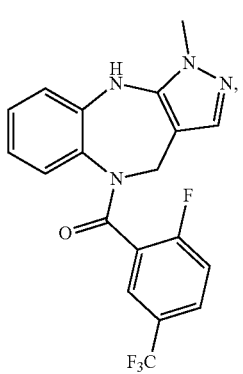
(xxxviii)
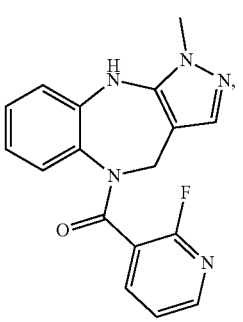
(xxxix)
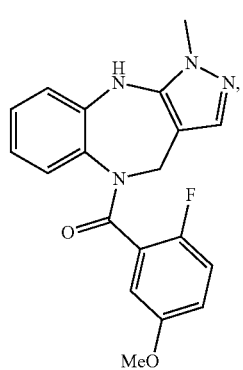
(xl)
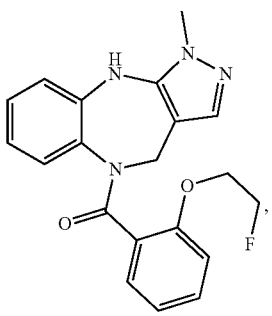
(xli)
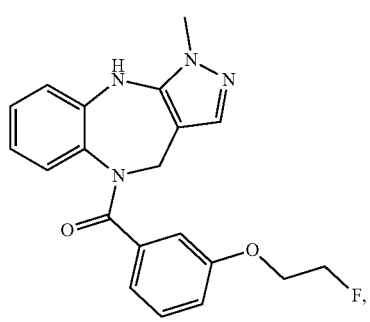
(xlii)
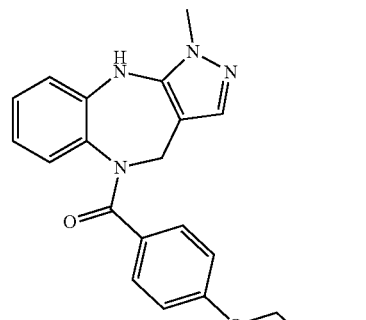
(xliii)
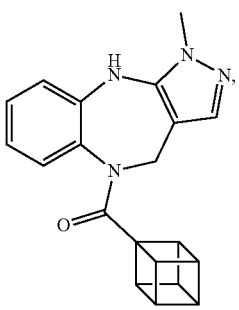
(xliv)
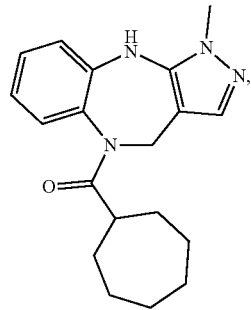

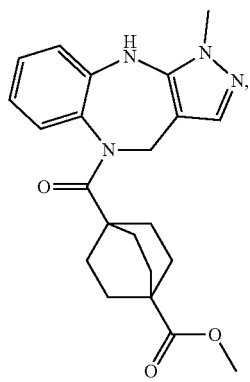 (xlv)
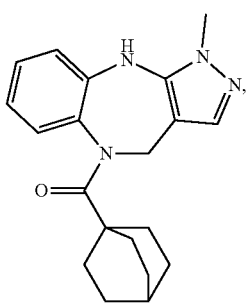 (xlvi)
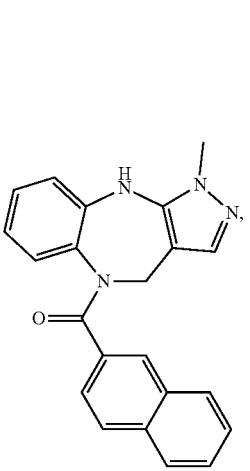 (xlvii)
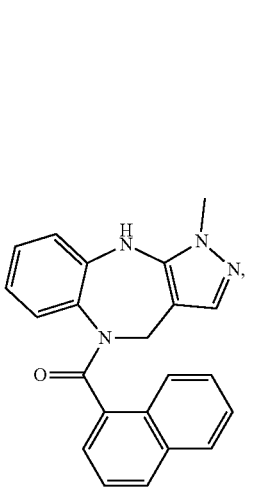 (xlviii)
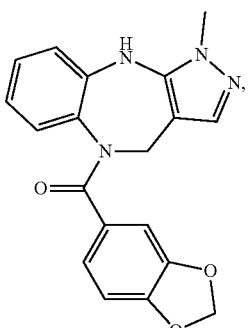 (xlix)
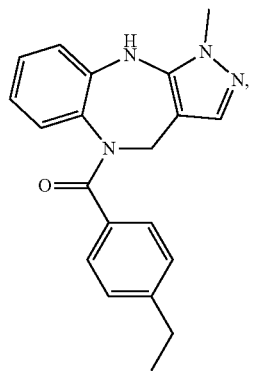 (l)
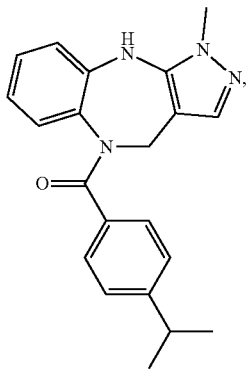 (li)
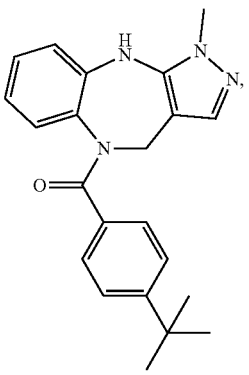 (lii)

-continued
(liv)
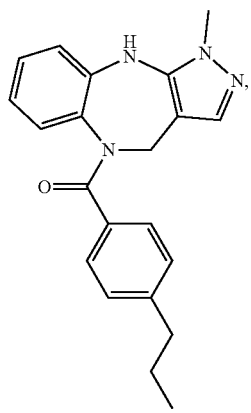
(lv)
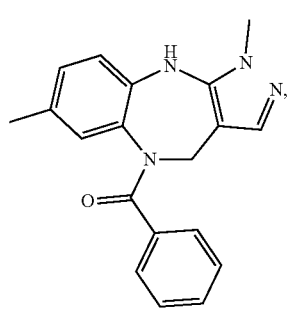
(lvi)
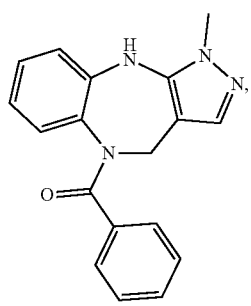
(lvii)
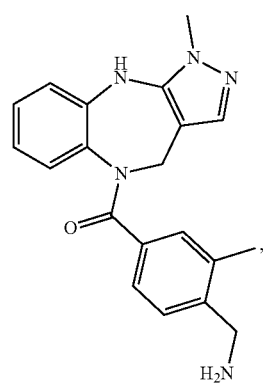
-continued
(lviii)
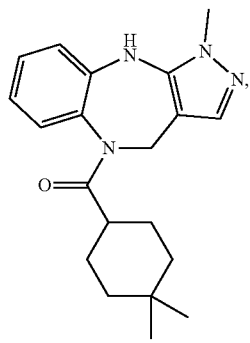
(lix)
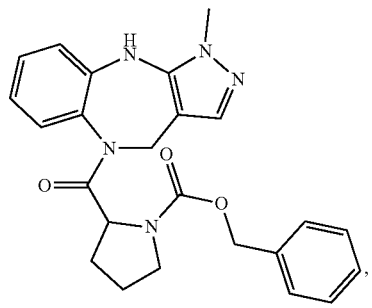
(lx)
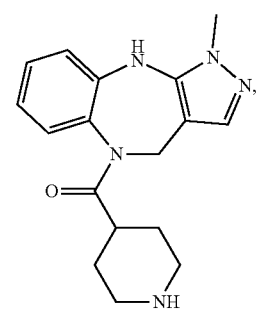
(lxi)
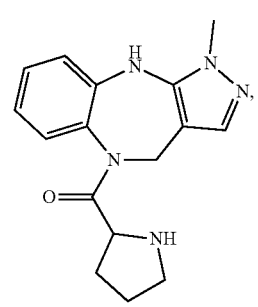
(lxii)
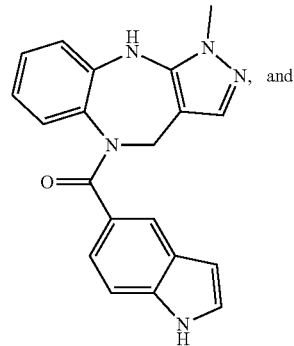
and

91

-continued (lxiii)

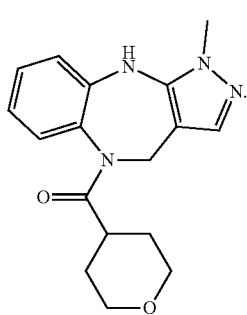

15. A compound of Formula I,

Formula I

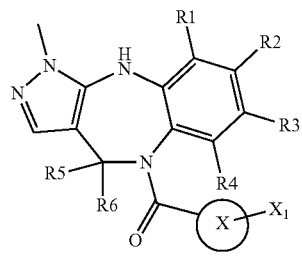

wherein R1, R3, R4, R5, an R6 are each independently selected from the group consisting of: H, F, Cl, Br, I, NH$_2$, NO$_2$, OH, ON═O, substituted or unsubstituted C$_1$-C$_4$ alkyl, substituted or unsubstituted C$_2$-C$_4$ alkenyl, substituted or unsubstituted C$_2$-C$_4$ alkynyl, substituted or unsubstituted —OC$_1$-C$_4$ alkyl, substituted or unsubstituted —OC$_2$-C$_4$ alkenyl, substituted or unsubstituted —OC$_2$-C$_4$ alkynyl, substituted or unsubstituted —NHC$_1$-C$_4$ alkyl, substituted or unsubstituted —NHC$_2$-C$_4$ alkenyl, substituted or unsubstituted —NHC$_2$-C$_4$ alkynyl, a substituted or unsubstituted aryl, and a substituted or unsubstituted heterocyclyl;

wherein R2 is selected from the group consisting of: H, F, Br, I, NH$_2$, NO$_2$, OH, ON═O, substituted methyl, substituted or unsubstituted C$_2$-C$_4$ alkyl, substituted or unsubstituted C$_2$-C$_4$ alkenyl, substituted or unsubstituted C$_2$-C$_4$ alkynyl, substituted or unsubstituted —OC$_1$-C$_4$ alkyl, substituted or unsubstituted —OC$_2$-C$_4$ alkenyl, substituted or unsubstituted —OC$_2$-C$_4$ alkynyl, substituted or unsubstituted —NHC$_1$-C$_4$ alkyl, substituted or unsubstituted —NHC$_2$-C$_4$ alkenyl, substituted or unsubstituted —NHC$_2$-C$_4$ alkynyl, a substituted or unsubstituted aryl, and a substituted or unsubstituted heterocyclyl;

wherein each R1, R2, R3, R4, R5, or R6 that is a substituted aryl or a substituted heterocyclyl includes one or more substituents selected from the group consisting of F, Cl, Br, I, NH$_2$, N═O, NO$_2$, NHCH$_3$, OH, OCH$_3$, OC≡N, ON═O, SH, SCH$_3$, S(═O)$_n$OH, S(═O)$_n$CH$_3$, SC≡N, COOH, CH$_3$, CH$_m$F$_{(3-m)}$, CH$_m$Cl$_{(3-m)}$, CH$_m$Br$_{(3-m)}$, OCH$_3$, OCH$_m$F$_{(3-m)}$, OCH$_m$Cl$_{(3-m)}$, and OCH$_m$Br$_{(3-m)}$;

wherein X is a cyclic structure selected from the group consisting of: a fused or unfused aryl; a fused or unfused heterocyclyl; and a fused or unfused cycloalkyl; and

92 wherein X1 represents one to three atoms or moieties independently selected from the group consisting of: H, F, Cl, Br, I, OH, ON═O, substituted or unsubstituted C$_1$-C$_4$ alkyl, substituted or unsubstituted C$_2$-C$_4$ alkenyl, substituted or unsubstituted C$_2$-C$_4$ alkynyl, substituted or unsubstituted —OC$_1$-C$_4$ alkyl, substituted or unsubstituted —OC$_2$-C$_4$ alkenyl, substituted or unsubstituted —OC$_2$-C$_4$ alkynyl, substituted or unsubstituted —NHC$_1$-C$_4$ alkyl, substituted or unsubstituted —NHC$_2$-C$_4$ alkenyl, substituted or unsubstituted —NHC$_2$-C$_4$ alkynyl, —COOH, —C$_1$ alkyl-COOH, —COOC$_1$-C$_2$ alkyl, —COOC$_1$-C$_2$ alkaryl, —C$_1$ alkyl-COOC$_1$-C$_2$ alkyl, —C$_1$-C$_2$ alkaryl, —OC$_1$-C$_2$ alkaryl, —NC$_1$-C$_2$ alkaryl, —C$_1$-C$_2$ alkyl-heterocyclyl, —OC$_1$-C$_2$ alkyl-heterocyclyl, and —NC$_1$-C$_2$ alkyl-heterocyclyl;

wherein each alkyl, alkenyl, or alkynyl that is independently substituted with one or more substituent selected from the group consisting of: F, Cl, Br, I, ═NH, N═O, NO$_2$, NHCH$_3$, N═C═O, N═C═S, ═O, OH, OCH$_3$, OC≡N, ON═O, ═S, SH, SCH$_3$, S(═O)$_n$OH, S(═O)$_n$CH$_3$, and SC≡N;

wherein each m is an integer selected from 0, 1, and 2; and each n is an integer selected from 0, 1, and 2; and wherein the compound is not selected from the group consisting of:

i)

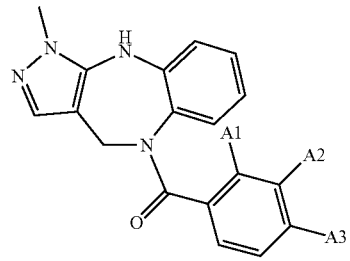

when A1 is H; A2 is CH$_3$; and A3 is any one of CH$_2$CH$_2$COOH, CH═CHCOOH, OCH$_2$CH$_2$CH$_2$COOH, CH$_2$CH$_2$C(═O)NHCH$_3$, NH$_2$, or NO$_2$; or ii)

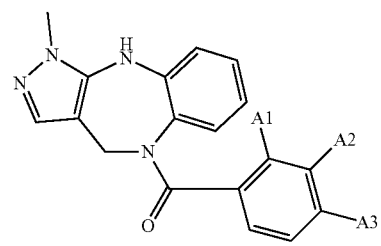

when A1 is H; A2 is H; and A3 is OH; or iii) a compound wherein the substituted or unsubstituted cycloalkyl is a substituted cyclohexane group.

16. A compound selected from the group consisting of:
(i)
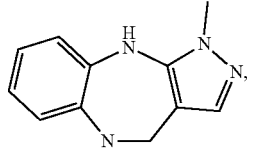
(ii)
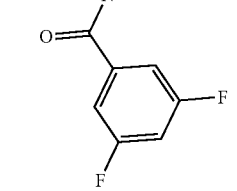
(iii)
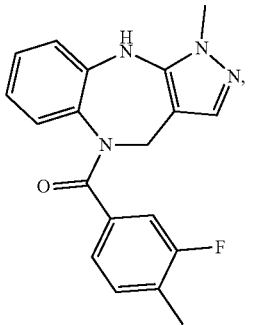
(iv)
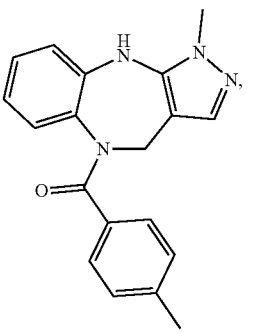
(v)
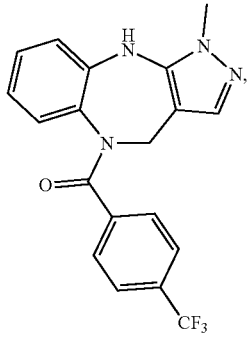
(vi)
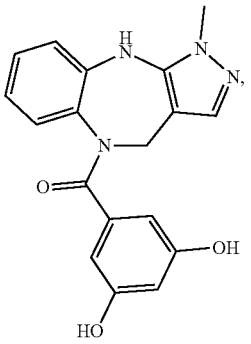
(vii)
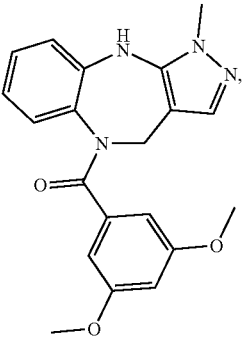
(viii)
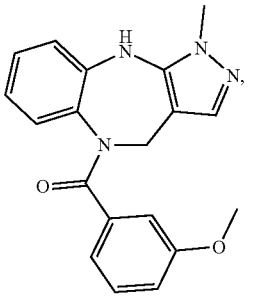
(ix)
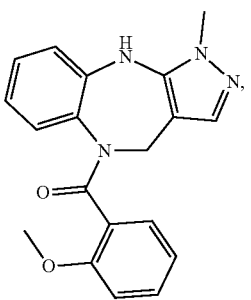

(x)
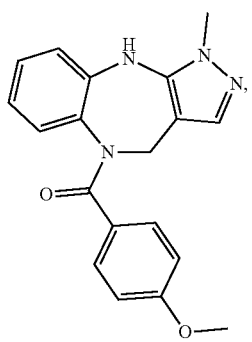
(xi)
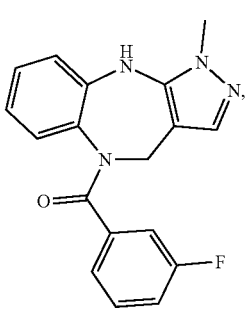
(xii)
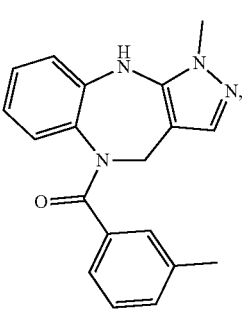
(xiii)
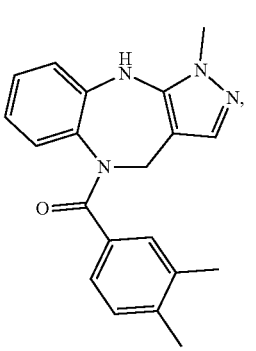
(xiv)
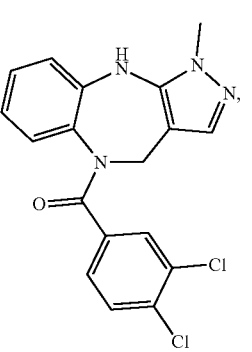
(xv)
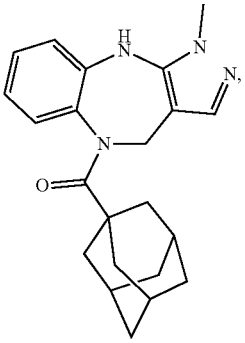
(xvi)
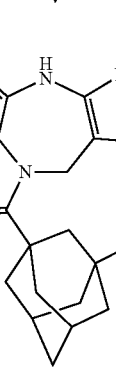
(xvii)
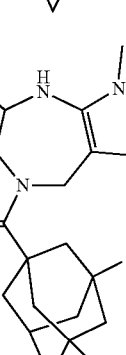
(xviii)
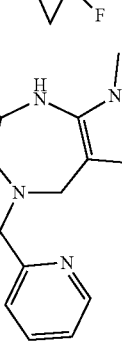
(xix)
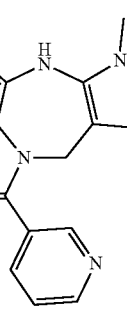

-continued
(xx)
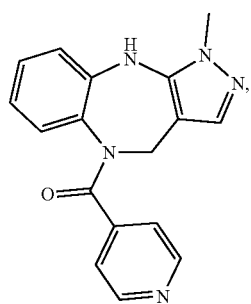
(xxi)
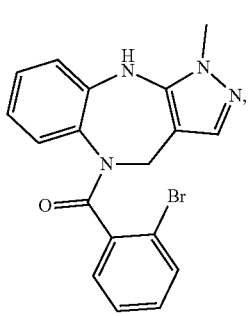
(xxii)
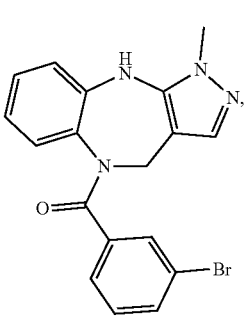
(xxiii)
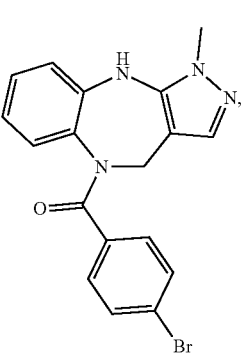
(xxiv)
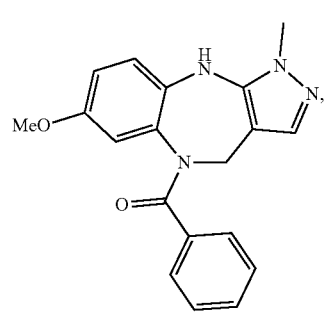
-continued
(xxv)
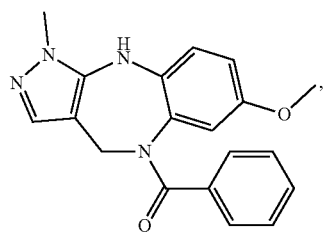
(xxvi)
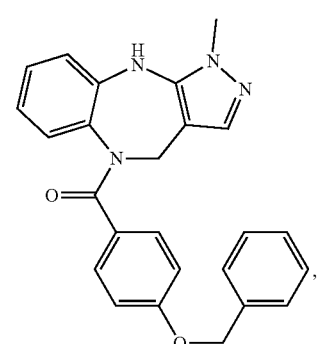
(xxviii)
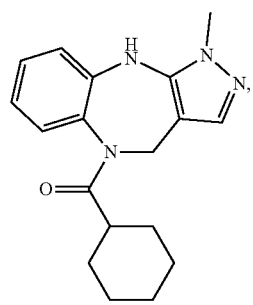
(xxix)
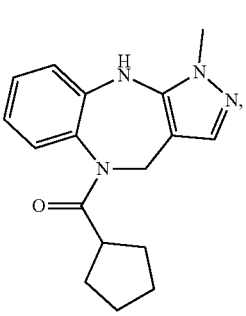
(xxx)
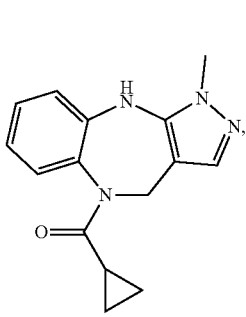

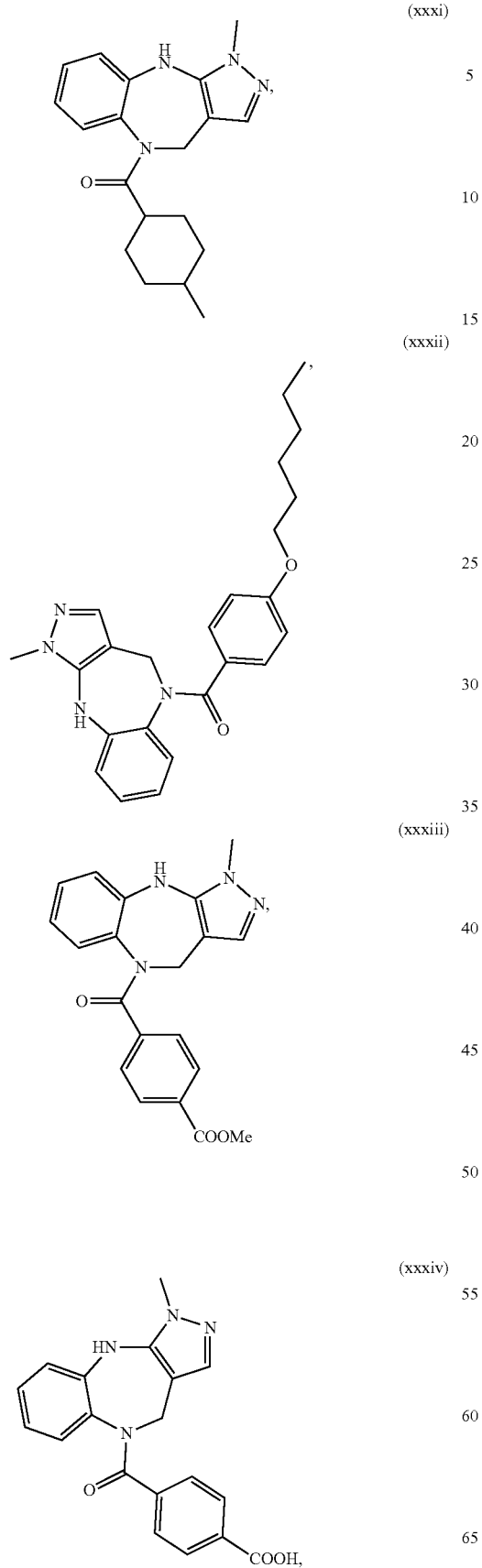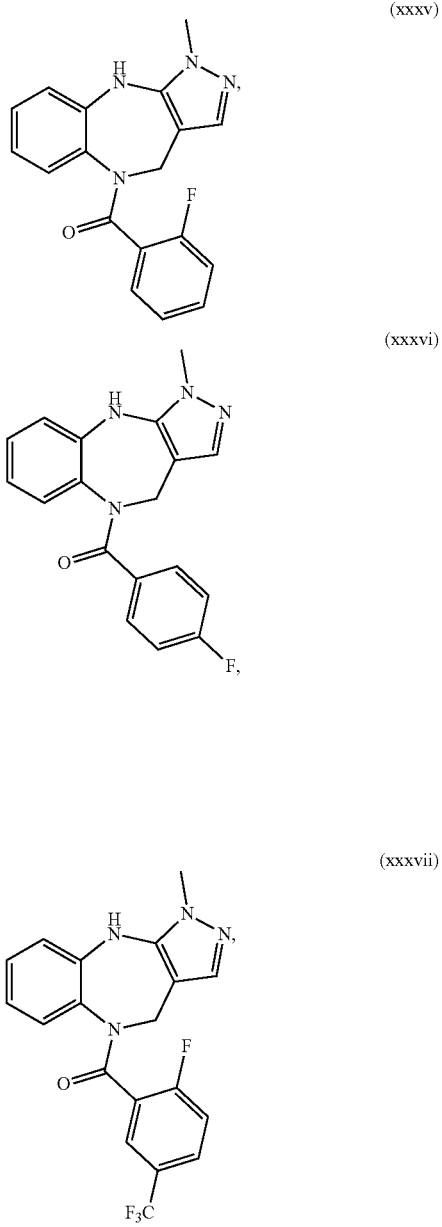

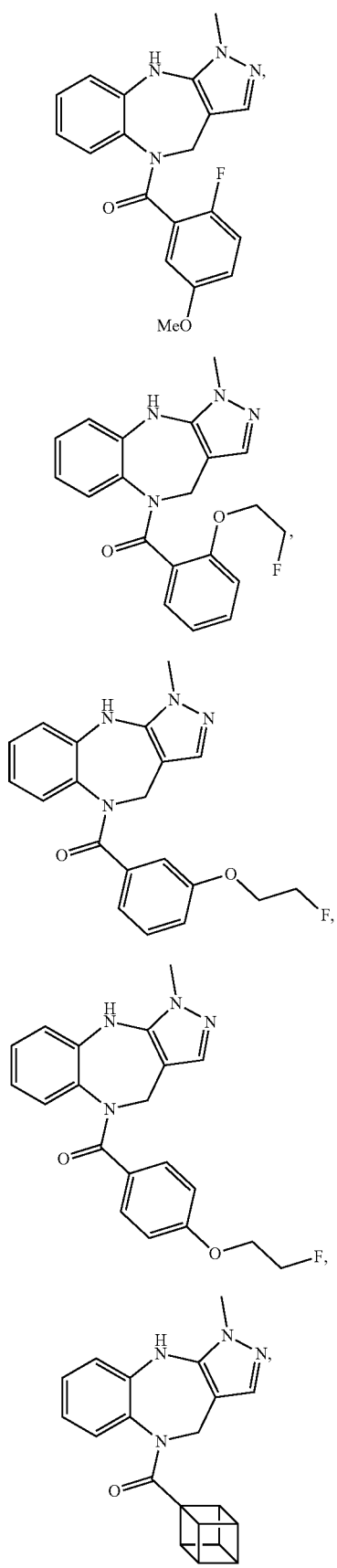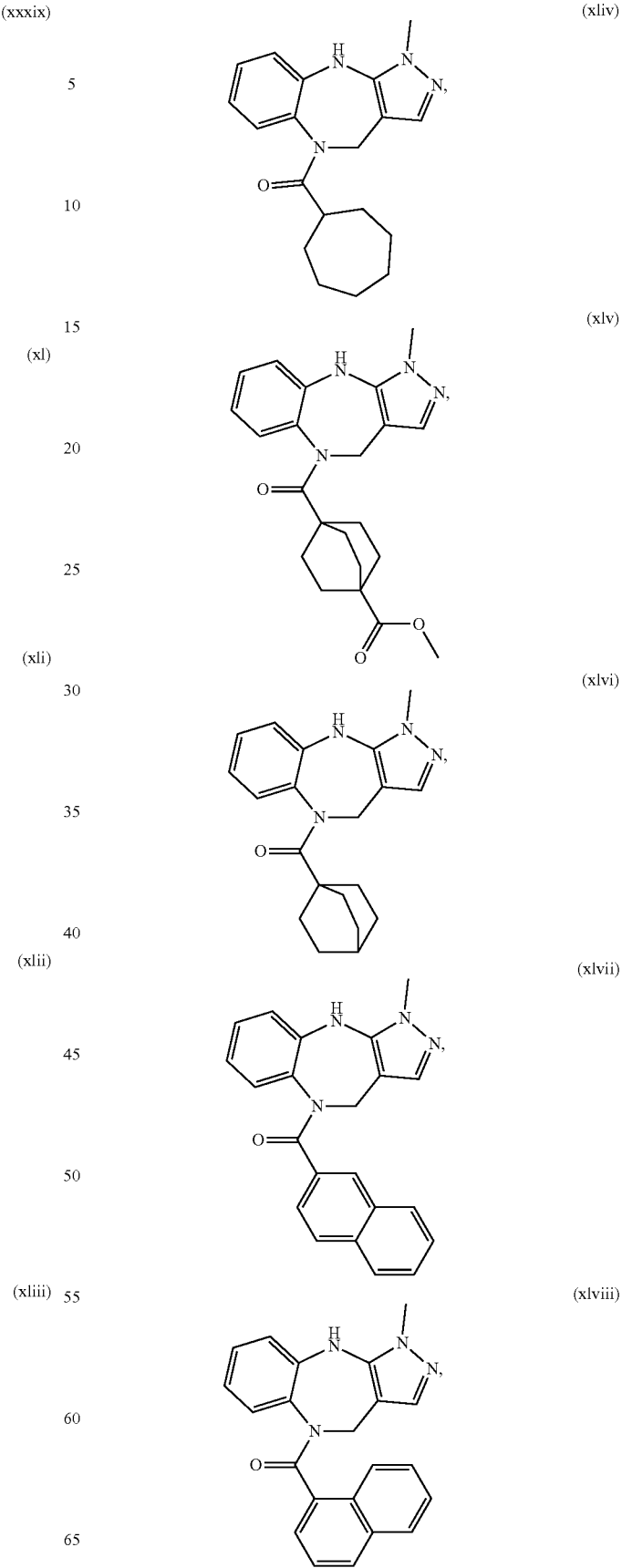

(xlix)
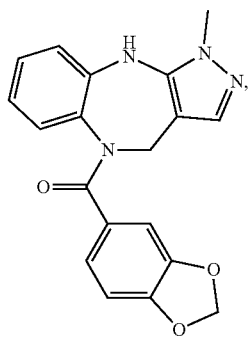
(l)
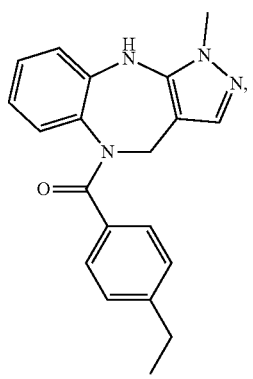
(li)
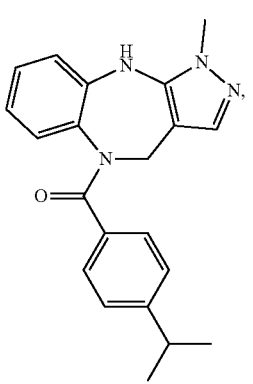
(lii)
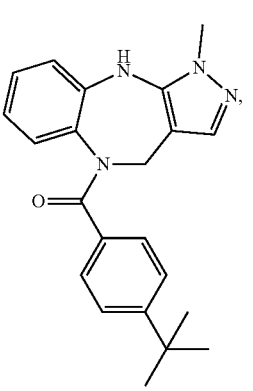
(liv)
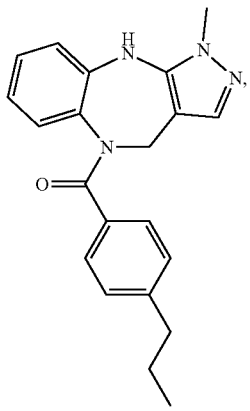
(lv)
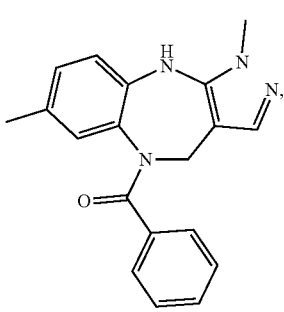
(lvi)
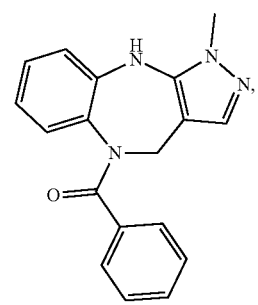

105
-continued
(lviii)
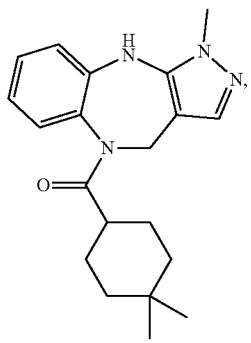
(lix)
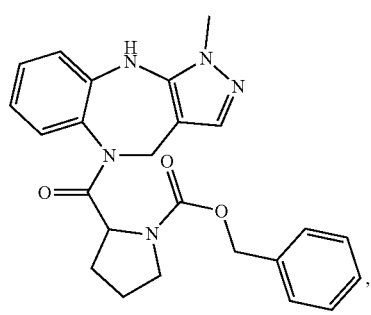
(lx)
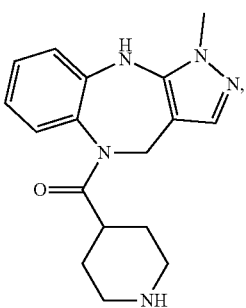
106
-continued
(lxi)
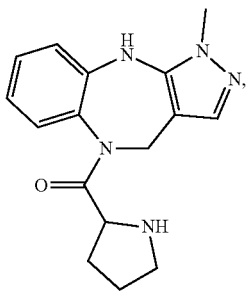
(lxii)
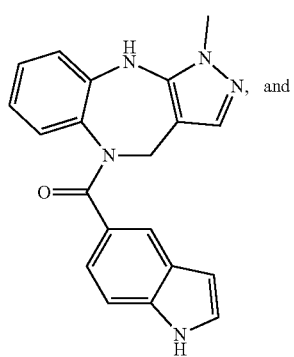
and
(lxiii)
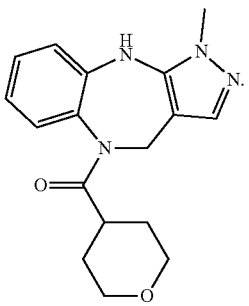
* * * * *

UNITED STATES PATENT AND TRADEMARK OFFICE
CERTIFICATE OF CORRECTION

| | | |
|---|---|---|
| PATENT NO. | : 11,491,165 B2 | Page 1 of 1 |
| APPLICATION NO. | : 16/439570 | |
| DATED | : November 8, 2022 | |
| INVENTOR(S) | : Kassiou et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 187 days.

Signed and Sealed this
Fourteenth Day of January, 2025

Derrick Brent
*Acting Director of the United States Patent and Trademark Office*